US006841717B2

(12) United States Patent
Boronat et al.

(10) Patent No.: US 6,841,717 B2
(45) Date of Patent: Jan. 11, 2005

(54) METHYL-D-ERYTHRITOL PHOSPHATE PATHWAY GENES

(75) Inventors: Albert Boronat, Barcelona (ES); Narciso Campos, Barcelona (ES); Manual Rodriguez-Concepcion, Barcelona (ES); Michel Rohmer, Strasbourg (FR); Myriam Seemann, Rixheim (FR); Henry E. Valentin, Chesterfield, MO (US); Tyamagondlu V. Venkatesh, St. Louis, MO (US); Mylavarapu Venkatramesh, Ballwin, MO (US)

(73) Assignee: Monsanto Technology, L.L.C., St. Louis, MO (US)

( * ) Notice: Subject to any disclaimer, the term of this patent is extended or adjusted under 35 U.S.C. 154(b) by 0 days.

(21) Appl. No.: 09/921,992

(22) Filed: Aug. 6, 2001

(65) Prior Publication Data

US 2002/0069426 A1 Jun. 6, 2002

Related U.S. Application Data

(60) Provisional application No. 60/223,483, filed on Aug. 7, 2000.

(51) Int. Cl.$^7$ .......................... C12N 15/82; C12N 5/04; A01H 5/00; A01H 5/10
(52) U.S. Cl. ...................... 800/278; 800/298; 800/287; 536/23.6; 536/24.1; 435/468; 435/419
(58) Field of Search .............................. 536/23.1, 23.6; 800/278, 287, 290, 298; 435/468, 419

(56) References Cited

U.S. PATENT DOCUMENTS

| | | | |
|---|---|---|---|
| 4,727,219 | A | 2/1988 | Brar et al. |
| 5,304,478 | A | 4/1994 | Bird et al. |
| 5,429,939 | A | 7/1995 | Misawa et al. |
| 5,432,069 | A | 7/1995 | Grüninger et al. |
| 5,545,816 | A | 8/1996 | Ausich et al. |
| 5,618,988 | A | 4/1997 | Hauptmann et al. |
| 5,684,238 | A | 11/1997 | Ausich et al. |
| 5,693,507 | A | 12/1997 | Daniell et al. |
| 5,750,865 | A | 5/1998 | Bird et al. |
| 5,792,903 | A | 8/1998 | Hirschberg et al. |
| 5,876,964 | A | 3/1999 | Croteau et al. |
| 5,908,940 | A | 6/1999 | Lane et al. |
| 6,281,017 | B1 | 8/2001 | Croteau et al. |
| 6,303,365 | B1 | 10/2001 | Martin et al. |
| 6,541,259 | B1 | 4/2003 | Lassner et al. |
| 2002/0069426 | A1 | 6/2002 | Boronat et al. |
| 2002/0108148 | A1 | 8/2002 | Boronat et al. |
| 2003/0148300 | A1 | 8/2003 | Valentin et al. |
| 2003/0150015 | A1 | 8/2003 | Norris et al. |
| 2003/0154513 | A1 | 8/2003 | van Eenennaam et al. |
| 2003/0166205 | A1 | 9/2003 | van Eenennaam et al. |
| 2003/0170833 | A1 | 9/2003 | Lassner et al. |
| 2003/0176675 | A1 | 9/2003 | Valentin et al. |
| 2003/0213017 | A1 | 11/2003 | Valentin et al. |
| 2004/0018602 | A1 | 1/2004 | Lassner et al. |
| 2004/0045051 | A1 | 3/2004 | Norris et al. |

FOREIGN PATENT DOCUMENTS

| | | |
|---|---|---|
| CA | 2372332 | 11/2000 |
| DE | 198 35 219 | 2/2000 |
| EP | 0 531 639 A2 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 A2 A3 | 11/1996 |
| WO | WO 96/38567 | 12/1996 |
| WO | WO 97/17447 | 5/1997 |
| WO | WO 97/27285 | 7/1997 |
| WO | WO 97/49816 | 12/1997 |
| WO | WO 98/04685 | 2/1998 |
| WO | WO 98/06862 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |

(List continued on next page.)

OTHER PUBLICATIONS

Fourgoux–Nicol et al (1999, Plant Molecular Biology 40 : 857–872).*
Bowie et al (1990, Science 247:1306–10).*
McConnell et al (2001, Nature 411 (6838):709–713).*
Baker et al (1993, NCBI Accession No. X64451).*

(List continued on next page.)

Primary Examiner—Amy J. Nelson
Assistant Examiner—Stuart F. Baum
(74) Attorney, Agent, or Firm—Fulbright & Jaworski L.L.P.

(57) ABSTRACT

The present invention provides and includes nucleic acids, proteins and antibodies associated with novel genes in the MEP pathway. The invention further encompasses methods utilizing such molecules, for example in gene isolation, gene analysis and the production of transgenic plants. The present invention also includes transgenic plants modified to express proteins associated with the MEP pathway.

6 Claims, 4 Drawing Sheets

FOREIGN PATENT DOCUMENTS

| | | |
|---|---|---|
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99 58649 | 11/1999 |
| WO | WO 00/01650 | 1/2000 |
| WO | WO 00 08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WO 00 17233 | 3/2000 |
| WO | WO 00/22150 A3 | 4/2000 |
| WO | WO 00/28005 | 5/2000 |
| WO | WO 00/34448 | 6/2000 |
| WO | WO 00/32757 A2 A3 | 6/2000 |
| WO | WO 00/42205 A2 A3 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/68393 | 11/2000 |
| WO | WO 00/65036 A2 A3 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 A3 | 11/2001 |
| WO | WO 02/00901 A1 | 1/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Hecht et al., "Studies on the nonmevalonate pathway to terpenes: the role of the GcpE (IspG) protein," *Proc. Natl. Acad. Sci. USA*, National Academy of Science, Washington, US, 98: 14837–14842, 2001.

Quero et al., "Functional analysis of the *Arabidopsis thaliana* GCPE protein involved in plastid isoprenoid biosynthesis," *FEBS Letters*, Elsevier Science Publishers, 514:343–346, 2002.

Database accession No. AQ690643; XP002221177; 93% Identity to SEQ ID No. 2, Abstract, Jul. 2, 1999.

Database accession No. AB005246; XP00220622; 81% Ungapped Identity to SEQ ID No. 4, abstract & Sato et al., Structural analysis of arabidopsis thaliana chromosome 5.I. Sequence features of the 1.6 MB regions covered by twenty physically assigned P1 clones, DNA Research, 4:215–230, 1997.

Sato et al., Database EMBL, Accession No.: AB005246 (Jul. 18, 1997).

Wing et al, Datebase EMBL, Accession No. AQ690643 (XP–002221177) Jul. 2, 1999.

Baker et al., "Sequence and characterization of the gcpE gene of *Escherichia coli*", Fems Microbiology Letters. 94: 175–180 (1992).

Hecht et al., "Studies of the nonmevalonate pathway to terpenes: The role of the GcpE (IspG) protein," PNAS vol 98, No. 26 14837–14842, Dec. 18, 2001.

Querol et al., "Functional Analysis od the *Arabidopsis thaliana* GCPE protein involved in plastid isoprenoid biosynthesis," FEBS Letters 514 (2002) 343–346.

Bevan, "Binary Agrobacterium vectors for plant transformation", *Nucleic Acids Research* 12:8711–8720 (1984).

Duvold et al., "Incorporation of 2–C–Methyl–D–erythritol, a Putative Isoprenoid Precursor in the Mevalonate–Independent Pathway, into Ubiquinone and Menaquinone of *Escherichia coli*", *Tetrahedron Letters* 38:6181–6184 (1997).

Eisenreich et al., "The deoxyxylulose phosphate pathway of terpenoid biosynthesis in plants and microorganisms" *Chem. Bio.* 5:R221–233 (1998).

Elliott, "A Method for Constructing Single–Copy lac Fusions in *Salmonella typhimiurium* and Its Application to the hemA–prfA Operon" *J. Bacteriol.* 174:245–253 (1992).

Herz et al., "Biosynthesis of terpenoids: YgbB protein converts 4–diphosphocytidyl–2C–methyl–D–erythritol 2–phosphate to 2C–methyl–D–erythritol 2, 4–cyclodiphosphate," *PNAS* 97(6):2485–2490(2000).

Rather et al., "aarC, an Essential Gene Involved in Density–Dependent Regulation of the 2'–N–Acetyltransferase in Providencia stuartii," *J. Bacteriol.* 179:2267–2273 (1997).

Rohmer et al., "Isoprenoid biosynthesis in bacteria: a novel pathway for the early steps leading to isopentenyl diphosphate," *Biochem. J*. 295:517–524 (1993).

Rohmer, "Isoprenoid biosynthesis via the mevalonate–independent route, a novel target for antibacterial drugs?", *Prog. Drug. Res.* 50:135–154 (1998).

Rohmer, "The mevalonate–independent methylerythritol 4–phosphate (MEP) pathway for isoprenoid biosynthesis, including carotenoids," *Pure Appl. Chem.* 71 No. 12:2279–2284 (1999).

Simons et al., "Improved single and multicopy lac–based cloning vectors for protein and operon fusions," *Gene* 53:85–96 (1987).

Addlesee et al., "Cloning, sequencing and functional assignment of the chlorophyll biosyntheses gene, chlP, of Synechocystis sp. PCC 6803", FEBS Letters 389 (1996) 126–130.

Arango et al., "Tocopherol synthesis from homogentisate in *Capsicum anuum* L. (yellow pepper) chromoplast membranes: evidence for tocopherol cyclase", Biochem J., 336:531–533 (1998).

Arigoni et al., "Terpenoid biosynthesis from 1–deoxy–D–xylulose in higher plants by intramolecular skeletal rearrangement", Proc. Natl. Acad. Sci. USA, 94:10600–10605 (1997).

Bayley et al., "Engineering 2,4–D resistance into cotton," Theor Appl Genet, 83:645–649 (1992).

Bentley, R., "The Shikimate Pathway—A Metabolic Tree with Many Branches," Critical Reviews ™ in Biochemistry and Molecular Biology; vol. 25, Issue 5, 307–384 (1990).

Bevan, M., "Binary Agrobacterium vectors for plant transformation", Nucleic Acids Research, 12:8711–8721 (1984).

Beyer et al., "Phytoene–forming activities in wild–type and transformed rice endosperm," IRRN 21:2–3, p 44–45 (Aug.–Dec. 1996).

Bork, et al., "Go hunting in sequence database but watch for the traps", TIG 12, 10:425–427 (Oct. 1996).

Bouvier et al., "Dedicated Roles of Plastid Transketolases furing the Early Onset of Isoprenoid Biogenesis in Pepper Fruits", Plant Physiol., 117:1423–1431 (1998).

Bramley et al., "Biochemical characterization of transgenic tomato plants in which carotenoid synthesis has been inhibited through the expression of antisense RNA to pTOM5," The Plant Journal, 2,(3), 343–349 (1992).

Breitenbach et al., "Expression in *Escherichia coli* and properties of the carotene ketolase from *Haematococcus pluvialis*," FEMS Microbiology Letters 140, 241–246 (1996).

Broun et al., "Catalytic Plasticity of Fatty Acid Modification Enzymes Underlying Chemical Diversity of Plant Lipids," Science, 282:1315–1317 (1998).

Buckner et al., "The y1 Gene of Maize Codes for Phytoene Synthase," Genetics 143:479–488 (May 1996).

Burkhardt et al., "Genetic engineering of provitamin A biosynthesis in rice endosperm," Experientia, 818–821.

Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis" The Plant Journal, 11(5), 1071–1078 (1997).

Cahoon et al., "Production of Fatty Acid Components of Meadowfoam Oil in Somatic Soybean Embryos," Plant Physiology, 124:243–251 (2000).

Chaudhuri et al., "The purification of shikimate dehydrogenase from *Escherichia coli*" Biochem. J., 226:217–223 (1985).

Cheng et al., "Highly Divergent Methyltransferases Catalyze a Conserved Reaction in Tocopherol and Plastoquinone Synthesis in Cyanobacteria and Photosynthetic Eukaryotes", The Plant Cell, 15:2343–2356 (2003).

Collakova et al., "Isolation and Functional Analysis of Homogentisate Phytyltransferase from Synechocystis sp. PCC 6803 and Arabidopsis", Plant Physiology, 127:1113–1124 (2001).

Collakova et al., "Homogentisate Phytyltransferase Activity is Limiting for Tocopherol Biosynthesis in Arabidopsis", Plant Physiology, 131:632–642 (Feb. 2003).

Collakova et al., "Isolation and Characterization of Tocopherol Prenyl Transferase From Synechocystis and Arabidopsis", Poster Abstract see REN–01–026.

Cook et al., "Nuclear Mutations affecting plastoquinone accumulation in maize", Photosynthesis Research, 31:99–111 (1992).

Cunillera et al., "Characterization of dehydrodolichyl diphosphate synthase of *Arabidopsis thaliana*, a key enzyme in dolichol biosynthesis", FEBS Letters, 477:170–174 (2000).

d'Amato et al., "Subcellular localization of chorismate–mutase isoenzymes in protoplasts from mesophyll and suspension–cultured cells of *Nicotiana silvestris*," Planta, 162:104–106 (1984).

Doerks et al., "Protein annotation: detective work for function prediction", TIG, 14:248–250 (1998).

d'Harlingue et al., "Plastid Enzymes of Terpenoid Biosynthesis, Purification and Characerization of $_\gamma$–Tocopherol Methyltransferase from Capsicum Chromoplasts," The Journal of Biological Chemistry, vol. 260, No. 28, pp. 15200–15203, Dec. 5, 1985.

De Luca, Vincenzo, "Molecular characterization of secondary metabolic pathway", AgBiotech News and Information, 5(6):225N–229N (1993).

Duncan et al., "The overexpression and complete amino acid sequence of *Escherichia coli* 3–dehydroquinase", Biochem. J., 238:475–483 (1986).

Duvold et al., "Incorporation of 2–C–Methyl–D–erythritol, a Putative Isoprenoid Precursor in the Mevalonate–Independent Pathway, into Ubiquinone and Menaquinone of *Escherichia coli*", Tetrahedron Letters, 38(35):6181–6184 (1997).

Elliott, Thomas, "A Method for Constructing Single–Copy lac Fusions in *Salmonella typhimurium* and Its Application to the hemA–prfA Operon", Journal of Bacteriology, 174:245–253 (1992).

Ericson et al., "Analysis of the promoter region of napin genes from *Brassica napus* demonstrates binding of nuclear protein in vitro to a conserved sequence motif", Eur. J. Biochem., 197:741–746 (1991).

Estévez et al., "1–Deoxy–D–xylulose–5–phosphate Synthase, a Limiting Enzyme for Plastidic Isoprenoid Biosynthesis in Plants", The Journal of Biological Chemistry, 276(25):22901–22909 (2001).

Fellermeier et al., "Cell–free conversion of 1–deoxy–D–xylulose 5–phosphate and 2–C–methyl–D–erythritol 4–phosphate into $\gamma$–carotene in higher plants and its inhibition by fosmidomycin", Tetrahedron Letters, 40:2743–2746 (1999).

Fiedler et al., "The formation of homogentisate in the biosynthesis of tocopherol and plastoquinone in spinach chloroplasts", Planta, 155:511–515 (1982).

Fourgoux–Nicol et al., "Isolation of rapeseed genes expressed early and specifically during development of the male gametophyte", Plant Molecular Biology, 40:857–872 (1999).

Fraser et al., "Enzymic confirmation of reactions involved in routes to astaxanthin formation, elucidated using a direct substrate in vitro assay", Eur. J. Biochem., 252:229–236 (1998).

Fraser et al., "In Vitro Characterization of Astaxanthin Biosynthetic Enzymes", The Journal of Biological Chemistry, 272(10) 6128–6135 (1997).

Fray et al., "Constitutive expression of a fruit phytoene synthease gene in transgenic tomatoes causes dwarfism by redirecting metabolites from the gibberelin pathway", The Plant Journal, 8(5):693–701 (1995).

Fray et al., "Identification and genetic analysis of normal and mutant phytoene synthase genes of tomato by sequencing, complementation and co–suppression", Plant Molecular Biology, 22:589–602 (1993).

Fuqua et al., "Characterization of melA: a gene encoding melanin biosynthesis from the marine bacterium *Shewanella colwelliana*", Gene, 109:131–136 (1991).

Furuya et al., "Production of Tocopherols by Cell Culture of Safflower", Phytochemistry, 26(10):2741–2747 (1987).

Garcia et al., "Subcellular localization and purification of a p–hydroxyphenylpuryvate dioxygenase from cultured carrot cells and characterization of the corresponding cDNA", Biochem. J., 325:761–769 (1997).

Gaubier et al., "A chlorophyll synthetase gene from *Arabidopsis thaliana*,", Mol. Gen. Genet., 249:58–64 (1995).

Goers et al., "Separation and characterization of two chorismate–mutase isoenzymes from *Nicotiana silverstris*", Planta, 162:109–116 (1984).

Grabse et al., "Loss of α–tocopherol in tobacco plants with decreased geranylgeranyl reductase activity does not modify photosynthesis in optimal growth conditions but increases sensitivity to high–light stress", Planta, 213:620–628 (2001).

Harker et al., "Biosynthesis of kelocarotenoids in transgenic cyanobacteria expressing the algal gene for β–C–4 oxygenase, crtO", FEBS Letters, 404:129–134 (1997).

Harker et al., "Expression of prokaryotic 1–deoxy–D–xylulose–5–phosphatases in *Escherichia coli* increases carotenoid and ubiquinone biosynthesis", FEBS Letters, 448:115–119 (1999).

Herrmann, K.M., "The Shikimate Pathway as an Entry to Aromatic Secondary Metabolism", Plan Physiol., 107:7–12 (1995).

Herz et al., "Biosynthesis of terpenoids: YgbB protein converts 4–diphosphocytidyl–2C–methyl–D–erythritol 2–phosphate to 2C–methyl–D–erythritol 2,4–cyclodiphosphate", Proc. Natl. Acad. Sci. USA, 97(6):2486–2490 (2000).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343–352 (1995).

Kaneko et al., "Complete Genomic Sequence of the Filamentous Nitrogen–fixing Cyanobacterium Anabeaena sp. Strain PCC 7120", DNA Research, 8(5):205–213 (2001).

Keegstra, K., "Transport and Routing of Proteins into Chloroplasts", Cell, 56(2):247–253 (1989).

Keller et al., "Metabolic compartmentation of plastid prenyllipid biosynthesis Evidence for the involvement of a multifunctional geranylgeranyl reductase", Eur. J. Biochem., 251:413–417 (1998).

Kishore et al., "Amino Acid Biosynthesis Inhibitors as Herbicides", Ann. Rev. Biochem., 57:627–663 (1988).

Koziel et al., "Optimizing expression of transgenes with an emphasis on post–transcriptional events", Plant Molecular Biology, 32:393–405 (1996).

Kumagal et al., "Cytoplasmic inhibition of carotenoid biosynthesis with virus–derived RNA", Proc. Natl. Acad. Sci. USA 92:1679–1683 (1995).

Kuntz et al., "Identification of a cDNA for the plastid–located geranylgeranyl pyrophosphate synthase from *Capsicum annuum*: correlative increase in enzyme activity and transcript level during fruit ripening", The Plant Journal, 2(1):25–34 (1992).

Lange et al., "A Family of transketolases that directs isoprenoid biosynthesis via a mevalonate–independent pathway", Proc. Natl. Acad. Sci. USA, 95:2100–2104 (1998).

Lange et al., "Isoprenoid Biosyntheis via a Mevalonate–Independent Pathway in Plants: Cloning and Heterologous Expression of 1–Deoxy–D–xylulose–5–phosphate Reductoisomerase from Peppermint", Archives of Biochemistry and Biophysics, 365(1):170–174 (1999).

Li et al., "Identification of a maize endosperm–specific cDNA encoding famesyle pyrophosphate synthetase", Gene, 171:193–196 (1996).

Linthorst et al., "Constitutive Expression of Pathogenesis–Related Proteins PR–1,GRP, and PR–S in Tobacco Has No Effect on Virus Infection", The Plant Cell, 1:285–291 (1989).

Lois et al., "Cloning and characterization of a gene from *Escherichia coli* encoding a transketolase–like enzyme that catalyzes the synthesis of D–1–deoxyxylulose 5–phosphate, a common precursor for isoprenoid, thiamin, and pyridoxol biosynthesis", Proc. Natl. Acad. Sci. USA, 95(5):2105–2110 (1998).

Lopez et al., "Sequence of the bchG Gene from *Chloroflexus aurantiacus*: Relationship between Chlorophyll Synthase and other Polyprenyltransferases", Journal of Bacteriology, 178(11):3369–3373 (1996).

Lotan et al., "Cloning and expression in *Escherichia coli* of the gene encoding β–C–4–oxygenase, that converts β–carotene to the ketocarotenoid canthaxanthin in *Haemotococcus pluvialis*", FEBS Letters, 364:125–128 (1995).

Mahmoud et al., "Metabolic engineering of essential oil yield and composition in mint by altering expression of deoxyxylulose phosphate reductoisomerase and menthofuran synthase", PNAS, 98(15):8915–8920 (2001).

Mandel et al., "CLA1, a novel gene required for chloroplast development, is highly conserved in evolution", The Plant Journal, 9(5):649–658 (1996).

Marshall et al., "Biosynthesis of Tocopherols: A Re–Examination of the Biosynthesis and Metabolism of 2–Methyl–6–Phytyl–1,4–Benzoquinol", Phytochemistry, 24(8):1705–1711 (1985).

Misawa et al., "Expression of an Erwinia phytoene desaturase gene not only confers multiple resistance to herbicides interfering with carotenoid biosynthesis but also alters xanthophyll metabolism in transgenic plants", The Plant Journal, 6(4):481–489 (1994).

Misawa et al., "Elucidation of the *Erwinia uredovora* Carotenoid Biosynthetic Pathway by Functional Analysis of Gene Products Expressed in *Escherichia coli*," Journal of Bacteriology 172(12):6704–6712 (1990).

Misawa et al., "Functional expression of the *Erwinia uredovora* carotenoid biosynthesis gene crtI in transgenic plants showing an increase of β–carotene biosynthesis activity and resistance to the bleaching herbicide norfluorazon", The Plant Journal, 4(5):833–840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575–6584 (1995).

Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401–414 (1997).

Nawrath et al., "Targeting of the polyhydroxybutyrate biosynthetic pathway to the plastids of *Arabidopsis thaliana* results in high levels of polymer accumulation", Proc. Natl. Acad. Sci. USA, 91:12760–12764 (1994).

Norris et al., "Genetic Dissection of Carotenoid Synthesis in Arabidopsis Defines Plastoquinone as an Essential Component of Phytoene Desaturation", The Plant Cell, 7:2139–2149 (1995).

Norris et al., "Complementation of the Arabidopsis pds1 Mutation with the Gene Encoding p–Hydroxyphenylpyruvate Dioxygenase", Plant Physiol., 117:1317–1323 (1998).

Oh et al., "Molecular Cloning, Expression, and Functional Analysis of a cis–Prenyltransferase from *Arabidopsis thaliana*", The Journal of Biological Chemistry, 275(24):18482–18488 (2000).

Okada et al., "Five Geranylgeranyl Diphosphate Synthases Expressed in Different Organs Are Localized into Three Subcellular Compartments in Arabidopsis", Plant Physiology, 122:1045–1056 (2000).

Oommen et al., "The Elicitro–Inducible Alfalfa Isoflavone Reductase Promoter Confers Different Patterns of Developmental Expression in Homologous and Heterologous Transgenic Plants ", The Plant Cell, 6:1789–1803 (1994).

Oster et al., "The G4 Gene of *Arabidopsis thaliana* Encodes a Chlorophyll Synthase of Etiolated Plants", Bot. Acta, 110:420–423 (1997).

Peisker et al., "Phytol and the Breakdown of Chlorophyll in Senescent Leaves", J. Plant Physiol., 135:428–432 (1989).

Pompliano et al., "Probing Lethal Metabolic Perturbations in Plants with Chemical Inhibition of Dehydroquinate Synthase", J. Am. Chem. Soc., 111:1866–1871 (1989).

Porfirova et al., "Isolation of an Arabidopsis mutant lacking vitamin E and identification of a cyclase essential for all tocopherol biosynthesis", PNAS, 99(19):12495–12500 (2002).

Rippert et al., "Molecular and Biochemical characterization of an *Arabidopsis thaliana* arogenate dehydrogenase with two highly similar and active protein domains", Plant Mol. Biol., 48:361–368 (2002).

Rippert et al., "Engineering Plant Shikimate Pathway for Production of Tocotrienol and Improving Herbicide Resistance", Plant Physiology, 134:92–100 (2004).

Rodriquez–Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079–1089 (2002).

Rodriquez–Concepción et al., "1–Deoxy–D–xylulose 5–phosphate reductoisomerase and plastid isoprenoid biosynthesis during tomato fruit ripening", The Plant Journal, 27(3):213–222 (2001).

Rohdich et al., "Cytidine 5'–triphosphate–dependent biosynthesis of isoprenoids: YgbP protein of *Escherichia coli* catalyzes the formation of 4–diphosphocytidyl–2–C–methylerythritol", Proc. Natl. Acad. Sci. USA, 96(21):11758–11763 (1999).

Rohmer et al., "Glyceraldehyde 3–Phosphate and Pyruvate as Precursors of Isoprenic Units in an Alternative Non–mevalonate Pathway for Terpenoid Biosynthesis", J. Am. Chem. Soc., 118:2564–2566 (1996).

Rohmer et al., "Isoprenoid biosynthesis in bacteria: a novel pathway for the early steps leading to isopentenyl diphosphate", Biochem. J., 295:517–524 (1993).

Rohmer, M., "A Mevalonate–independent Route to Isopentenyl Diphosphate", Comprehensive Natural Products Chemistry, 2:45–67 (1999).

Rohmer, M., "Isoprenoid biosynthesis via the mevalonate–independent route, a novel target for antibacterial drugs?", Progress in Drug Research, 50:136–154 (1998).

Römer et al., "Expression of the Genes Encoding the Early Carotenoid Biosynthetic Enzymes in *Capsicum annuum*", Biochemical and Biophysical Research Communications, 196(3):1414–1421 (1993).

Ruzafa et al., "The protein encoded by the *Shewanella colwelliana melA* gene is a p–hydroxyphenylpyruvate dioxygenase", FEMS Microbiology Letters, 124:179–184 (1994).

Saint–Guily et al., "Complementary DNA Sequence of an Adenylate Translocator from *Arabidopsis thaliana*", Plant Physiol., 100(2):1069–1071 (1992).

Sandmann et al., "New functional assignment of the carotenogenic genes crtB and crtE with constructs of these genes from Erwinia species", FEMS Microbiology Letters, 90:253–258 (1992).

Sato et al., "Structural Analysis of *Arabidopsis thaliana* Chromosome 5. X. Sequence Features of the Region of 3,076,755 bp Covered by Sixty P1 and TAC Clones", DNA Research, 7(1):31–63 (2000).

Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41–54 (1998).

Savidge et al., "Isolation and Characterization of Homogentisate Phytyltransferase Genes from Synechocystis sp. PCC 6803 and Arabidopsis", Plant Physiology, 129:321–332 (2002).

Schwender et al., "Cloning and heterologous expression of a cDNA encoding 1–deoxy–D–xylulose–5–phosphate reductoisomerase of *Arabidopsis thaliana*", FEBS Letters, 455:140–144 (1999).

Scolnik et al., "Nucleotide Sequence of an Arabidopsis cDNA for Geranylgeranyl Pyrophosphate Synthase", Plant Physiol., 104(4):1469–1470 (1994).

Shewmaker et al., "Seed–specific overexpression of phytoene synthase: increase in carotenoids and other metabolic effects", The Plant Journal, 20(4):401–412 (1999).

Shigeoka et al., "Isolation and properties of γ–tocopherol methyltransferase in *Euglena gracilis*", Biochimica et Biophysica Acta, 1128: 220–226 (1992).

Shintani et al., "Elevating the Vitamin E Content of Plants Through Metabolic Engineering", Science, 282:2098–2100 (1998).

Singh et al., "Chorismate Mutase Isoenzymes from *Sorghum bicolor*: Purification and Properties", Archives of Biochemistry and Biophysics, 243(2):374–384 (1985).

Smith, F.W. et al., "The cloning of two Arabidopsis genes belonging to a phosphate transporter family", Plant Journal, 11(1):83–92 (1997).

Smith, C.J.S. et al., "Antisense RNA Inhibition of polygalacturonase gene expression in transgenic tomatoes", Nature, 334:724–726 (1998).

Smith, T.F. et al., "The challenges of genome sequence annotation or the devil is in the details", Nature Biotechnology, 15:1222–1223 (1997).

Soll et al., "Hydrogenation of Geranylgeraniol", Plant Physiol., 71:849–854 (1983).

Soll et al., "Tocopherol and Plastoquinone Synthesis in Spinach Chloroplasts Subfractions", Archives of Biochemistry and Biophysics, 204(2):544–550 (1980).

Soll et al., "2–Methyl–6–Phytylquinol and 2,3–Dimethyl–5–Phytylquinol as Precursors of Tocopherol Synthesis in Spinach Chloroplasts", Phytochemistry, 19:215–218 (1980).

Sprenger et al., "Identification of a thiamin–dependent synthase in *Escherichia coli* required for the formation of the 1–deoxy–D–xylulose 5–phosphate precursor to isoprenoids, thiamin, and pyridoxol", Proc. Natl. Acad. Sci. USA, 94:12857–12862 (1997).

Spurgeon et al., "Biosynthesis of Isoprenoid Compounds", 1:1–45 (1981).

Stam et al., "The Silence of Genes in Transgenic Plants", Annals of Botany, 79:3–12 (1997).

Stocker et al., "Identification of the Tocopherol–Cyclase in the Blue–Green Algae *Anabaena variabilis* Kützing (Cyanobacteria)", Helvetica Chimica Acta, 76:1729–1738 (1993).

Stocker et al., "The Substrate Specificity of Tocopherol Cyclase", Bioorganic & Medicinal Chemistry, 4(7):1129–1134 (1996).

Sun et al., "Cloning and Functional Analysis of the β–Carotene Hydroxylase of *Arabidopsis thaliana*", The Journal of Biological Chemistry, 271(40):24349–24352 (1996).

Suzich et al., "3–Deoxy–D–arabino–Heptulosonate 7–Phosphate Synthase from Carrot Root (*Daucus carota*) is a Hysteretic Enzyme", Plant Physiol., 79:765–770 (1985).

Svab et al., "High–frequency plastid transformation in tobacco by selection for a chimeric aadA gene", Proc. Natl. Acad. Sci. USA, 90:913–917 (1993).

Svab et al., "Stable transformation of plastids in higher plants", Proc. Natl. Acad. Sci. USA, 87:8526–8530 (1990).

Takahashi et al., "A 1–deoxy–D–xylulose 5–phosphate reductoisomerase catalyzing the formation of 2–C–methyl–D–erythritol 4–phosphate in an alternative nonmevalonate pathway for terpenoid biosynthesis", Proc. Natl. Acad. Sci. USA, 95:9879–9884 (1998).

Takatsuji, H., "Zinc–finger transcription factors in plants", CMLS Cell. Mol. Life Sci., Birkhauser Verlag Basel CH, 54(6):582–596 (1996).

Tjaden et al., "Altered plastidic ATP/ADP–transporter activity influences potato (*Solanum tubersomum* L.) tuber morphology, yield and composition of tuber starch", The Plant Journal, 16(5):531–540 (1998).

Town et al., "Whole genome shotgun sequencing of *Brassica oleracea*, BOGKS71TR BOGK *Brassica oleradea* genomic clone BOGKS71, DNA sequence", Database EMBL Accession No. BH534089 (Dec. 2001).

Town et al, "Whole genome shotgun sequencing of *Brassica oleracea*, BOGAU46TR BOGA *Brassica oleracea* genomic clone BOGAU46, DNA sequence", Database EMBL Accession No. BH248880 (Nov. 2001).

Verwoert et al., "Developmental specific expression and organelle targeting of the *Escherichia coli fabD* gene, encoding malonyl coenzyme A–acyl carrier protein transacylase in transgenic rape and tobacco seeds", Plant Molecular Biology, 26:189–202 (1994).

Xia et al., "A monofunctional prephenate dehydrogenase created by cleavage of the 5' 109 bp of the tyrA gene from *Erwinia herbicola*", Journal of General Microbiology, 138(7):1309–1316 (1992).

Xia et al., "The pheA / tyrA / aroF Region from *Erwinia herbicola*: An Emerging Comparative Basis for Analysis of Gene Organization and Regulation in Enteric Bacteria", Database GenBank on STN, GenBank Acc. No. (GBN): M74133, J. Mol. Evol., 36(2):107–120 Abstract (1993).

Yamamoto, E., "Purification and Metal Requirements of 3–Dehydroquinate Synthase from *Phaseolus mungo* Seedlings", Phytochemistry, 19:779–781 (1980).

Zaka et al., "Changes in Carotenoids and Tocopherols During Maturation of Cassia Seeds", Pakistan J. Sci. Ind. Res., 30(11): 812–814 (1987).

Zeidler et al., "Inhibition of the Non–Mevalonate 1–Deoxy–D–xylulose–5–phosphate Pathway of Plant Isoprenoid Biosynthesis by Fosmidomycin", A Journal of Biosciences, Zeitschrift fuer Naturforschung, Section C, 53(11/12):980–986 (Nov./Dec. 1998).

Zhu et al., "Geranylgeranyl pyrophosphate synthase encoded by the newly isolated gene GGPS6 from *Arabidopsis thaliana* is localized in mitochondria", Plant Molecular Biology, 35:331–341 (1997).

Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357–361 (1997).

Kaneko et al., NCBI General Identifier No. 1653572, Accession No. BAA18485 (Jul. 2001).

Kaneko et al., NCBI General Identifier No. 1001725, Accession No. BAA10562 (Feb. 2003).

Alcala et al., Genbank Accession No. AI 897027 (Jul. 1999).

Bevan et al., Database EMBL, Accession No. AL035394 (Feb. 1999).

Bevan et al., TREMBL Database Accession No. O65524 (Aug. 1998).

Campos et al., NCBI General Identifier BAA 18485, Database EMBL, Accession No.: AF148852, (2000).

Chen et al., EMBL Sequence Database Accession No. AI995392 (Sep. 1999).

Desprez et al., Database EMBL, Accession No. Z34566 (Jun. 1994).

Fedenko et al., Abstract: RU 2005353, Derwent Accession No.: 1994–253787.

Gaubier et al., Database EMBL, Accession No. Q38833 (Nov. 1996).

Kaneko et al., Database EMBL, Accession No. P73726 (Feb. 1997).

Kaneko et al., Databae EMBL, Accession No. P73962 (Jul., 1998).

Kaneko et al., EMBL Sequence Database Accession No. D90909 (Oct. 1996).

Kaneko et al., TREMBL Database Accession No. P73727 (Feb. 1997).

Lange et al., "Mentha × Piperita 1–deoxy–D–xylulose–5–phosphate Reductoisomerase (DXR) mRNA", complete cds, Entrez Report, Accession No. AF116825 (Apr. 1999).

Lin et al., Database EMBL, Accession No. AC003672 (Dec. 1997).

Lin et al., Database EMBL, Accession No. AC003673 (Dec. 1997).

Lin et al., Database EMBL, Accession No. AC004077 (Feb. 1998).

Malakhov et al., Database TREMBL, Accession No. Q55207 (Nov. 1996).

Murata et al., EMBL Sequence Database Accession No. D13960 (Mar. 1996).

Nakamura et al., Database EMBL, Accession No.: AB009053, Abstract (Dec. 1997) (1998)(2000).

Newman et al., Database EMBL, Accession No.: AA586087, Abstract (Sep. 1997).

Newman et al., Database EMBL, Accession No. R30625 (Aug. 1995).

Newman et al., Database EMBL, Accession No. T44803 (Feb. 1995).

Newman et al., DEBEST ID: 1262303, Entrez Report, Accession No.: AA586087 (Sep. 1997).

Oster et al., Database Biosis, Accession No. PREV199800047824 (Oct. 1997).

Ouyang et al., Database EMBL, Accession No. AF381248 (Jan. 2003).

Rounsley et al., Database EMBL, Accession No. B24116 (Oct. 1997).

Rounsley et al., Database EMBL, Accession No. B29398 (Oct. 1997).

Rounsley et al., Database TREMBL, Accession No. 064684 (Aug. 1998).

Schwender et al., *Arabidopsis thaliana* mRNA for Partial 1–deoxy–d–xylulose–5–phosphate Reductiosomerase (dxr gene ), Entrez Report, Accession No.: AJ242588 (Aug. 1999).

Scolnik et al., Database EMBL, Accession No. L40577 (Apr. 1995).

Shintani et al., Database NCBI, Accession No. AF104220 (Jan. 1999).

Shoemaker et al., Database EMBL, Accession No. AI748688 (Jun. 1999).

Shoemaker et al., Database EMBL, Accession No. AI9385569 (Aug. 1999).

Shoemaker et al., Database EMBL, Accession No. AI988542 (Sep. 1999).

Shoemaker et al., Database EMBL, Accession No. AW306617 (Jan. 2000).

Tabata et al., Database EMBL, Accession No. D64001 (Sep. 1995).

Tabata et al., Database EMBL, Accession No. D64006 (Sep. 1995).

Tabata et al., Database EMBL, Accession No. D90909 (Oct. 1996).

Tabata et al., Database EMBL, Accession No. D90911 (Oct. 1996).

Tabata et al., Database EMBL, Accession No. Q55145 (Nov. 1996).

Tabata et al., Database EMBL, Accession No. Q55500 (Nov. 1996).

Walbot, V., Database EMBL, Accession No. AI795655 (Jul. 1999).

Xia et al., Database EMBL, Accession No. M74133 (Jun. 1993).

Bowie et al., "Deciphering the Message in Protein Sequences: Tolerance to Amino Acid Substitutions", Science, 247:1306–1310 (1990).

McConnell et al., "Role of Phabulosa and Phavoluta in determining radial patterning in shoots", Nature, 411(6838): 709–713 (2001).

Baker et al., NCBI Accession No. X64451 (Dec. 1993).

* cited by examiner

```
EcgcpE : .........................................................MHNQAPIQRRKSTRIYVGNVPIGDG   :  25
AtgcpE : MATGVLPAPVSGIKIPDSKVGFGKSMNLVRICDVRSLRSARRRVSVIRNSNQGSDLAELQPASEGSPLLVPRQKYCESLHKTVRRKTRTVMVGNVALGSE : 100

EcgcpE : APIAVQSMVNIRITDVEATVNQIKAIERVGADIVRVSVPTMDAREAF......KLEKQQVNVPLVADIHFDYRIALKVAEYGVDCLRINPGNIG..... : 114
AtgcpE : HPIRIQIMVTTSDIJKDITGIVDEVMRIADKGADIVRHIVQGKKEADACFEIKDKLVQLNYNIPLVADIHFAPTVALFDKERVNPGNFADRRAQFE   : 199

EcgcpE : .........EERIRMVDCARDKNIPIRIGVNAGSIEKDICEKVGEPICALLESMRHVDHLDRLNEDQFKVSVRASDVFLAVESVRLIAKQ         : 198
AtgcpE : TIDYTEDEYQKELQHIEQVFTPIVEKCKKYGRAMRIGTNHGSISDRMMSYIGDISPRGMVESAFFEFARICRKLDVIHNFVFSMKASNPVIHMVQAVRLIVAE : 298

EcgcpE : I.....DQPLHLGITEAGGARSGAVKSAIGFELLISEGIGDIIRVSLAADFVEEIK                                           : 249
AtgcpE : MYVHGWDYPLHLGVTEAGEGEDGRMKSAIGIGTLIQDGCGDIIRVSLITEPEEEIDPCRRLANLGTKAAKLQQGAPFEEKHRHYFDFQRRTGLPVQKEG : 398

EcgcpE : ........................................................................                        :   -
AtgcpE : EEVDYRNVLHRDGSVLMSISLDQLKAPELLYRSLATKJVVGMPFKDLATVDSILLRELPPVDDQVARIALKRLIDVSMGVIAPLSEQLTKPLPNAMVLVN : 493

EcgcpE : ........................................................................                        :   -
AtgcpE : LKELSGGAYKLLPEGTRLVVSLRGDEPYEELEILKNIDATMILHDVPFTEDKVSRVHAARRLFEFLSENSVNFPVIHHINFPTGIHRDELVIHAGTYAGG : 598

EcgcpE : ...............VGFDILKSLRIRSRGINWACIICSRQEFDMIGTVNAEEQRLEDEIITPMDWSIIGGVVNGPGBALVSTLGVTGCNK         : 325
AtgcpE : LLVDGLGDGVMLEAPDQDFLRNTSFMLIQGCRMRNTKTEKVSCFSCGRTLFPIQEISAEIREKTSHEIPG.VSIAIMGGIVNGPGEMADADFGYVGGSP : 697

EcgcpE : .KSGINEDG.VRKDRIEDNNEMIDQLIEERIRAKASQLDEARIDVQQVEK : 372
AtgcpE : GKIDIRIVGKTVVKRGIAMTEATDAIIGLLIKEHG......RWDPPVADE : 740
```

Figure 4 pZL1 (135H1):

```
...[SalI]aaaaatcg(...)gaaaaATGGCGACTGGAGTATTGCCAGCTCCGGTTTCTGGGATCAAG
                          M  A  T  G  V  L  P  A  P  V  S  G  I  K
ATACCGGATTCGAAAGTCGGGTTTGGTAAAAGCATGAATCTTGTGAGAATTTGTGATGTTAGGAGTCTA
 I  P  D  S  K  V  G  F  G  K  S  M  N  L  V  R  I  C  D  V  R  S  L
BglII
|
AGATCTGCT(...)GATGAGTAGatttc(...)ataaaagt[NcoI][XbaI][BamHI][HindIII][SphI]...
 R  S  A (...) D  E  *
|
``` pQE30:

```
                                                              BamHI
SphI                                                            |
...[prom. T5][2x operator lac][RBS]ATGAGAGGATCG[6xHis]GGATCCGCATGC...
                                    M  R  G  S HHHHHH  G  S  ...
``` pQE-AGH:

```
                    BamHI/BglII                                SphI
                        |                                        |
...[RBS]ATGAGAGGATCG[6xHis]GGATCTGCT(...)GATGAGTAGatttc(...)...GCATGC..
        M  R  G  S HHHHHH  G  S  A (...) D  E  *
```

Figure 5

SEQUENCE LISTING

```
<160> NUMBER OF SEQ ID NOS: 85

<210> SEQ ID NO 1
<211> LENGTH: 2520
<212> TYPE: DNA
<213> ORGANISM: Arabidopsis thaliana
<220> FEATURE:
<221> NAME/KEY: CDS
<222> LOCATION: (154)..(2376)

<400> SEQUENCE: 1
aaaaatcgtc aatccctctc aaactcttct caccactaat ttcttcctct ggaacattct         60
cttctctatt attttgattc ccttggcctc aacactggtt tctcaattgc atgatcttgg        120
ctcgtcttca gttactttga ttcactgaga aaa atg gcg act gga gta ttg cca        174
                                    Met Ala Thr Gly Val Leu Pro
                                      1               5 gct ccg gtt tct ggg atc aag ata ccg gat tcg aaa gtc ggg ttt ggt         222
Ala Pro Val Ser Gly Ile Lys Ile Pro Asp Ser Lys Val Gly Phe Gly
        10                  15                  20 aaa agc atg aat ctt gtg aga att tgt gat gtt agg agt cta aga tct         270
Lys Ser Met Asn Leu Val Arg Ile Cys Asp Val Arg Ser Leu Arg Ser
 25                  30                  35 gct agg aga aga gtt tcg gtt atc cgg aat tca aac caa ggc tct gat         318
Ala Arg Arg Arg Val Ser Val Ile Arg Asn Ser Asn Gln Gly Ser Asp
 40                  45                  50                  55 tta gct gag ctt caa cct gca tcc gaa gga agc cct ctc tta gtg cca         366
Leu Ala Glu Leu Gln Pro Ala Ser Glu Gly Ser Pro Leu Leu Val Pro
             60                  65                  70 aga cag aaa tat tgt gaa tca ttg cat aag acg gtg aga agg aag act         414
Arg Gln Lys Tyr Cys Glu Ser Leu His Lys Thr Val Arg Arg Lys Thr
         75                  80                  85 cgt act gtt atg gtt gga aat gtc gcc ctt gga agc gaa cat ccg ata         462
Arg Thr Val Met Val Gly Asn Val Ala Leu Gly Ser Glu His Pro Ile
     90                  95                 100 agg att caa acg atg act act tcg gat aca aaa gat att act gga act         510
Arg Ile Gln Thr Met Thr Thr Ser Asp Thr Lys Asp Ile Thr Gly Thr
105                 110                 115 gtt gat gag gtt atg aga ata gcg gat aaa gga gct gat att gta agg         558
Val Asp Glu Val Met Arg Ile Ala Asp Lys Gly Ala Asp Ile Val Arg
120                 125                 130                 135 ata act gtt caa ggg aag aaa gag gcg gat gcg tgc ttt gaa ata aaa         606
Ile Thr Val Gln Gly Lys Lys Glu Ala Asp Ala Cys Phe Glu Ile Lys
                140                 145                 150 gat aaa ctc gtt cag ctt aat tac aat ata ccg ctg gtt gca gat att         654
Asp Lys Leu Val Gln Leu Asn Tyr Asn Ile Pro Leu Val Ala Asp Ile
            155                 160                 165 cat ttt gcc cct act gta gcc tta cga gtc gct gaa tgc ttt gac aag         702
His Phe Ala Pro Thr Val Ala Leu Arg Val Ala Glu Cys Phe Asp Lys
        170                 175                 180 atc cgt gtc aac cca gga aat ttt gcg gac agg cgg gcc cag ttt gag         750
Ile Arg Val Asn Pro Gly Asn Phe Ala Asp Arg Arg Ala Gln Phe Glu
    185                 190                 195
```

```
                                                                -continued acg ata gat tat aca gaa gat gaa tat cag aaa gaa ctc cag cat atc    798
Thr Ile Asp Tyr Thr Glu Asp Glu Tyr Gln Lys Glu Leu Gln His Ile
200                 205                 210                 215 gag cag gtc ttc act cct ttg gtt gag aaa tgc aaa aag tac ggg aga    846
Glu Gln Val Phe Thr Pro Leu Val Glu Lys Cys Lys Lys Tyr Gly Arg
                220                 225                 230 gca atg cgt att ggg aca aat cat gga agt ctt tct gac cgt atc atg    894
Ala Met Arg Ile Gly Thr Asn His Gly Ser Leu Ser Asp Arg Ile Met
            235                 240                 245 agc tat tac ggg gat tct ccc cga gga atg gtt gaa tct gcg ttt gag    942
Ser Tyr Tyr Gly Asp Ser Pro Arg Gly Met Val Glu Ser Ala Phe Glu
        250                 255                 260 ttt gca aga ata tgt cgg aaa tta gac tat cac aac ttt gtt ttc tca    990
Phe Ala Arg Ile Cys Arg Lys Leu Asp Tyr His Asn Phe Val Phe Ser
265                 270                 275 atg aaa gcg agc aac cca gtg atc atg gtc cag gcg tac cgt tta ctt   1038
Met Lys Ala Ser Asn Pro Val Ile Met Val Gln Ala Tyr Arg Leu Leu
280                 285                 290                 295 gtg gct gag atg tat gtt cat gga tgg gat tat cct ttg cat ttg gga   1086
Val Ala Glu Met Tyr Val His Gly Trp Asp Tyr Pro Leu His Leu Gly
                300                 305                 310 gtt act gag gca gga gaa ggc gaa gat gga cgg atg aaa tct gcg att   1134
Val Thr Glu Ala Gly Glu Gly Glu Asp Gly Arg Met Lys Ser Ala Ile
            315                 320                 325 gga att ggg acg ctt ctt cag gac ggg ctc ggt gac aca ata aga gtt   1182
Gly Ile Gly Thr Leu Leu Gln Asp Gly Leu Gly Asp Thr Ile Arg Val
        330                 335                 340 tca ctg acg gag cca cca gaa gag gag ata gat ccc tgc agg cga ttg   1230
Ser Leu Thr Glu Pro Pro Glu Glu Glu Ile Asp Pro Cys Arg Arg Leu
345                 350                 355 gct aac ctc ggg aca aaa gct gcc aaa ctt caa caa ggc gca ccg ttt   1278
Ala Asn Leu Gly Thr Lys Ala Ala Lys Leu Gln Gln Gly Ala Pro Phe
360                 365                 370                 375 gaa gaa aag cat agg cat tac ttt gat ttt cag cgt cgg acg ggt gat   1326
Glu Glu Lys His Arg His Tyr Phe Asp Phe Gln Arg Arg Thr Gly Asp
                380                 385                 390 cta cct gta caa aaa gag gga gaa gag gtt gat tac aga aat gtc ctt   1374
Leu Pro Val Gln Lys Glu Gly Glu Glu Val Asp Tyr Arg Asn Val Leu
            395                 400                 405 cac cgt gat ggt tct gtt ctg atg tcg att tct ctg gat caa cta aag   1422
His Arg Asp Gly Ser Val Leu Met Ser Ile Ser Leu Asp Gln Leu Lys
        410                 415                 420 gca cct gaa ctc ctc tac aga tca ctc gct aca aag ctt gtc gtg ggt   1470
Ala Pro Glu Leu Leu Tyr Arg Ser Leu Ala Thr Lys Leu Val Val Gly
425                 430                 435 atg cca ttc aag gat ctg gca act gtt gat tca atc tta tta aga gag   1518
Met Pro Phe Lys Asp Leu Ala Thr Val Asp Ser Ile Leu Leu Arg Glu
440                 445                 450                 455 cta ccg cct gta gat gat caa gtg gct cgt ttg gct cta aaa cgg ttg   1566
Leu Pro Pro Val Asp Asp Gln Val Ala Arg Leu Ala Leu Lys Arg Leu
                460                 465                 470 att gat gtc agt atg gga gtt ata gca cct tta tca gag caa cta aca   1614
Ile Asp Val Ser Met Gly Val Ile Ala Pro Leu Ser Glu Gln Leu Thr
            475                 480                 485 aag cca ttg ccc aat gcc atg gtt ctt gtc aac ctc aag gaa cta tct   1662
Lys Pro Leu Pro Asn Ala Met Val Leu Val Asn Leu Lys Glu Leu Ser
        490                 495                 500 ggt ggc gct tac aag ctt ctc cct gaa ggt aca cgc ttg gtt gtc tct   1710
Gly Gly Ala Tyr Lys Leu Leu Pro Glu Gly Thr Arg Leu Val Val Ser
505                 510                 515
```

-continued

| | | |
|---|---|---|
| cta cga ggc gat gag cct tac gag gag ctt gaa ata ctc aaa aac att<br>Leu Arg Gly Asp Glu Pro Tyr Glu Glu Leu Glu Ile Leu Lys Asn Ile<br>520                        525                      530                      535 | 1758 |
| gat gct act atg att ctc cat gat gta cct ttc act gaa gac aaa gtt<br>Asp Ala Thr Met Ile Leu His Asp Val Pro Phe Thr Glu Asp Lys Val<br>                    540                      545                      550 | 1806 |
| agc aga gta cat gca gct cgg agg cta ttc gag ttc tta tcc gag aat<br>Ser Arg Val His Ala Ala Arg Arg Leu Phe Glu Phe Leu Ser Glu Asn<br>                555                      560                      565 | 1854 |
| tca gtt aac ttt cct gtt att cat cac ata aac ttc cca acc gga atc<br>Ser Val Asn Phe Pro Val Ile His His Ile Asn Phe Pro Thr Gly Ile<br>570                        575                      580 | 1902 |
| cac aga gac gaa ttg gtg att cat gca ggg aca tat gct gga ggc ctt<br>His Arg Asp Glu Leu Val Ile His Ala Gly Thr Tyr Ala Gly Gly Leu<br>                585                      590                      595 | 1950 |
| ctt gtg gat gga cta ggt gat ggc gta atg ctc gaa gca cct gac caa<br>Leu Val Asp Gly Leu Gly Asp Gly Val Met Leu Glu Ala Pro Asp Gln<br>600                        605                      610                      615 | 1998 |
| gat ttt gat ttt ctt agg aat act tcc ttc aac tta tta caa gga tgc<br>Asp Phe Asp Phe Leu Arg Asn Thr Ser Phe Asn Leu Leu Gln Gly Cys<br>                    620                      625                      630 | 2046 |
| aga atg cgt aac act aag acg gaa tat gta tcg tgc ccg tct tgt gga<br>Arg Met Arg Asn Thr Lys Thr Glu Tyr Val Ser Cys Pro Ser Cys Gly<br>                635                      640                      645 | 2094 |
| aga acg ctt ttc gac ttg caa gaa atc agc gcc gag atc cga gaa aag<br>Arg Thr Leu Phe Asp Leu Gln Glu Ile Ser Ala Glu Ile Arg Glu Lys<br>                    650                      655                      660 | 2142 |
| act tcc cat tta cct ggc gtt tcg atc gca atc atg gga tgc att gtg<br>Thr Ser His Leu Pro Gly Val Ser Ile Ala Ile Met Gly Cys Ile Val<br>665                        670                      675 | 2190 |
| aat gga cca gga gaa atg gca gat gct gat ttc gga tat gta ggt ggt<br>Asn Gly Pro Gly Glu Met Ala Asp Ala Asp Phe Gly Tyr Val Gly Gly<br>680                        685                      690                      695 | 2238 |
| tct ccc gga aaa atc gac ctt tat gtc gga aag acg gtg gtg aag cgt<br>Ser Pro Gly Lys Ile Asp Leu Tyr Val Gly Lys Thr Val Val Lys Arg<br>                    700                      705                      710 | 2286 |
| ggg ata gct atg acg gag gca aca gat gct ctg atc ggt ctg atc aaa<br>Gly Ile Ala Met Thr Glu Ala Thr Asp Ala Leu Ile Gly Leu Ile Lys<br>                715                      720                      725 | 2334 |
| gaa cat ggt cgt tgg gtc gac ccg ccc gtg gct gat gag tag<br>Glu His Gly Arg Trp Val Asp Pro Pro Val Ala Asp Glu<br>730                        735                      740 | 2376 |
| atttcaaaac ggagaaagat gggtgggcca ttctttgaaa actgtgagag aagatatata | 2436 |
| tatttgtgtg tgtatatcat ctgtttgttg tgtattgcat catcattttg aacaaatgtc | 2496 |
| caaatctctt aagttgataa aagt | 2520 |

<210> SEQ ID NO 2
<211> LENGTH: 33675
<212> TYPE: DNA
<213> ORGANISM: Oryza sativa
<220> FEATURE:
<221> NAME/KEY: CDS
<222> LOCATION: (6924)..(7019),(7163)..(7269),(7344)..(7444),(7525)..
    (7634),
<222> LOCATION: (7694)..(7813),(7923)..(8153),(8253)..(8369),(8515)..
    (8589),
<222> LOCATION: (9012)..(9071),(9163)..(9225),(9328)..(9472),(9589)..
    (9730),
<222> LOCATION: (9951)..(10028),(10134)..(10293),(10694)..(10798),
<222> LOCATION: (11028)..(11129)
<221> NAME/KEY: unsure -continued
<222> LOCATION: (1..33675)
<223> OTHER INFORMATION: unsure at all n locations

<400> SEQUENCE: 2

```
cttaaccctc gccgactgcc tggagattcg tgccgatcga tacacgtggc agcgcctaac      60
gcgtaacccc tccctcactt ggagattcgt gcaagcaact cgattaatgc attaatgctg     120
tcgcgtaggt ttccctacgg aagagctgag tttcgtaacg aaaaaaaccg gccacgtttc     180
gcatcgagcc tactttaatt agcgtgggaa ataattcaa  agtagcgacc tgtaccctgt     240
ggcaacctag cgcgcgcggc catggctctt gttccgctcg tgacagtgct cctgttcgcc     300
ggctcatgcc tcggatcagc gccgccgacg acatcgccgg cggcgtcggc ggcgtccacg     360
gcgacacgta cggtagtagt cgacggcatt acggccatct acaaacctcg gcgactcgct     420
gtcggacacc gcaacctcgc caggcaaggc gccaccggcg ggctgctccg gtacaccacg     480
aggcttccct acggcgtcac cgtcggccgc gccaccggcc ggtgctccga cggctacctc     540
atcatcgact tcctcggtga cgtcatcagt ttaatttctc tctctcttcc gtctgaaaaa     600
tggaagaaac aatattatat tacgttatat atatatgcgt ttttgtttcg gattaaattg     660
tggatatgat cgatcgatgt gcagctagag atcttggcct ccctctgctc aacccgtacc     720
tcgacgaggg cgcggacttc gcccacggct caacttcgc  cgtcgccggc gccaccgcgc     780
tcaacacgac ggcgctcgcc gccaggcgga tcaccgtccc ccacaccaac agcccctcg     840
acgtgcagct cagattttt  ttgttttaga agggtatt   ttttacccgg cctctacatc     900
caaccggata tatacggcta ttgaagtagg gaacttaacc ctgtaaacaa tccatccata     960
gaggatatga acctaagacc ttgaggtact acttcaaccg gatatatacg tgcagctcag    1020
atggttcaag gaattcatga actccacaac tagttctcct caaggtgaac gaacaaactg    1080
aaacgcattt cagcttaatt tcgaccggtg cctgatcagt gccagtcagc aatgctgtat    1140
ctcacaaata attaagctaa tgtacagctt ttcagtgcta gaatgacttt catatagaga    1200
aatcttgtgt tatatatata tactttttt  tgaaagaaaa aagttctttt gtgtgagcat    1260
tgcattgcag agatccgtga aaagctgtcg aagtcactgg ttatgctggg agagatcgga    1320
ggaaacgact acaactacgc cttcctccag acctggccga tggacggtgg atacagcctc    1380
ggcaacgtca cacgcatgat cgaaagcgtt gccacggccg tcgatcttgt accggaagtc    1440
gtgcagtcca tagccagcgc agccaaggta cacaccattc ttttccatta attttggga     1500
ccttattttt aaaataataa tcctggctac aaagtaatta attaagaact aaattaattt    1560
ttgtgggttt tgtgacacag gaggtgctcg acatgggcgc gacgcgggtg gtgatcccgg    1620
gcaacctccc gctgggttgc gtgccgagct acatgagcgc ggtgaacgcg acggaccggg    1680
cggcgtacga cgcccgcgga tgcctcgtcg cgctcaacct cttcgcggcg ctgcacaacg    1740
cgtggctgcg ccgcgccgtc ggggagctgc ggcgcgcgta ccgggcgcc  gcggtggtcg    1800
cgtacgcgga ctactccgcc gcgtacgccg cgacgctgga cggggcagcg cgctcggct     1860
tcgacgagcg gcgcgtgttc agggcgtgct gcggcaaggg cggcggggc  gcgtacgggt    1920
tcgacgtgcg cgcgatgtgc ggcgcgccgg ggacggcggc gtgcgcggac ccggggaggt    1980
acgtgagctg ggacggcgtc cacctgacgc agcgcgcgta cggcgtcatg gccgagctgc    2040
tgttccgccg tggcctcgtg cacccgcctc cgataaattt cacgaacagc gcgcgcgcgt    2100
gaggcggtgt tgcatggctt gcgcgttttt tctgatcaaa actactcaag tttgagccgt    2160
tttgatttat aaataaaacc atatgcgatt ttgctaaacg tttgtcgcgt gatttctctt    2220
```

```
cggaagaaaa aatctcaccc gagtgatgca taggcggtcc caaccatatg tgccctgacc    2280
tttctctgct tccttcgcgt cgtgcactga caacctcaca gtatgttttt ggtatgggcg    2340
cttgcggccc aactcaatct gtaatacatt gggctgtcgt attgggtttg ttggacttca    2400
tagactggat cggagaaagt tgggtaattg acttttcat ttttgctata aaatgattaa     2460
ttaaacagtc taggataatt actgtagact ctaataatat tgtttggtta agtattatta    2520
tacattcctg tatttgacac tctaagagca tggccaagag ttgcctgaaa gtctcttcct    2580
aaatctgcct ttcattctct aatgagaatt taaggattaa aaatatactt attttcaata    2640
gacagcataa atttaattcc ctagaataaa aaaatgcccc cctaacaaca gaaattagat    2700
tcctctaccc gcacctcatc agatcgctcg atttaagatc acgccatctg acaccgccct    2760
cccgctcgct cttctctagt gtgggagtct cgcgctcaag agacggaaat cgggaacaag    2820
aatgattcct agcttagcga gaatgaaggg gaagacatat gtcataccta cacccacata    2880
agtatgccct agcacaaggg atgaaaacgg atcgaaaacg gatggaaact agctttatca    2940
tattcgtttt catttttttt tcggaatcgg attcgaaatc gaaaactcgg atacggaaat    3000
aaaattgaat attatcgaat acagatacgg agcgaatata agatgaacg  aatacagtag    3060 cgaatattta ccggtatata aaaaacccct caaattgagt ttcttgatta agaaagagat    3120
atcgcttatt attttagtta aatatctcca acatttatat cgtcaatttt atagacggtt    3180
ccacaatcgt atgtgaaaat cgattttcat ggttgttcct ctaagagatc catatgcaaa    3240
tatgattatc attttctatt ccaagacctt ttactagatg tataacttat ttaccattgc    3300
ataaattgga gatgttattt attttacttc acatcttcga aacttgtaat gtatgtatta    3360
tactttaaat gctttcaagt acaaatgtta taaactacaa agtggtagat cccgttgagc    3420
tctacaactt tgatatggaa cacatctcca tcagatgtcg tttgaattgt agatctgaga    3480
ttttgtaaaa tttaatatgg tatattataa tgaatattta gacccttaaa tgaccttaaa    3540
taataaaata gtcaataata aagttgtaga tctcatcgag ctctataatg ttgatatgaa    3600
gtttgtcttc atctgattcc gtatgaaaaa gttatgtata tacatgtt    tttttataaa    3660 atttgctcaa tatctgcgga tatccgaaaa aaatttcgga tagttttttaa ccgttttcg    3720 attccgatgg atagtatcct tactgtattc gttttcgttt ccgagaaaaa atatccaaat    3780
tcgtttccga atccgagaat ttttggataa ttccgacaga aactatccga atccgaaaaa    3840
tggttcggac ggacggaaac tatccaaacc agtttcatcc cggctagcac gcatttaaat    3900
tcacatgagg ttgcacattt atctgaggta aaaagattgg aaacggttac tggttcgtca    3960
agaattttcc gtatttatca gtataactat tcaatgacga catcaacata acagaaaatt    4020
aaaacaacat gagtcgattt tatatataac tagaaacgaa aacagtataa ctgttacgaa    4080
aacactagat tgatgggtcg aaaatttcca ccacggtttt tatgcctacc tttcaacgct    4140
cccaaagttc ccacgaccca aaacatgtgt gggagaactt ccgcccacat ggagacggtt    4200
gtctcaggga aacgtgccat ctgctttgct ccaggtcaac acatgtggtg tgactgaact    4260
ggccatcgtc tcaatattgt catctacccg tcataccatg ccaccggacc agaaggtgat    4320
tatggtcttc ggcggccgtc gcgcgcggat gccttgctcc acaacaagtc agccgctcaa    4380
accacactcc cctttggcat tgaacatgag gtttgacgac gatgtgtgtg tatgtttggg    4440
caggtagctt tgtttcaagc tgcactagct aattaagatc gatctccttg tcaaagtcac    4500
gatcaaacat cgaaagtaca tgcatggaag aaatgttgaa atgtaatgaa ctaaatgatg    4560
tccttttctc cccttattaa acaacatcaa gtttctttta tttctaaaga atgttaatat    4620
```

-continued

```
cctttttatt tcttcaataa atagtactgc actccctatg gttttttgttg tttagcatct    4680
tgactttcgg gcatacgttt tatgatttat cttattacaa aatataatta tcatttattt    4740
tatcattaca aatactttaa aaataacatt atcagctgat tttgaattaa aactaaaatt    4800
acaccttaat tacaatatac ttcacatagc aattataata taactatata caacttacac    4860
tataagttat gttcaaaata tttttcctac aaaaactatc accagattct tagacagtcc    4920
cattccacca cctcagctgc cgtgaaagaa ctttgggtct taaataagtc caaatttatc    4980
tttttgtttt ctcaataaaa tattcgaatt atccaacaaa tcaaggaaaa aacatccttc    5040
gatgacccat gaatattcgt gaagtttctc ctctagccag taacaatacg gaacaatcag    5100
acaattttat ctggctcaag caccatctct cgcaccagat taaactattt tttttttcatg   5160
gtacaataca atcccatgcc ggccacgaaa acaaatggc agaaataata aacgaacaaa     5220
acagcctctc tccatcgtga actaataaaa aataaaataa aaacaaaaca aaatgataat    5280
ggaattacga agcgcatggg aaaacgacgg gcacgattaa atcatggcgg ggagagcccg    5340
gaaccccact tccacacctc caaccccacg ccgtcagcct tcccctccca tgcacccggt    5400
ccaccaacac ctcatctctt ggaccccaca cgcagccact gcccacggca acgcggtgct    5460
cgtgcaccga gtccacacga cgcgccgcgc ggtgcggggg cgccggcctc tggggataaa    5520
tgggctaatc cggtagaaag cccaccactc gctcgccagt tcgtcgtcct cttcgccgag    5580
ctcgcgagct ctcgcactct gtctccatcc ccgcatcgca tcgcctcgcc gctgctgatc    5640
tcgtcgcggt cgccggaggg gagctacgag gttggggagc cttatctcta cttcctgaga    5700
tttctagtag ctttgtgtat gtgtgtgtgt ttgtgtgttg gggggacgcc gatcgggtgg    5760
atcctcctgt ggtggttggt tgggcgcaat tcgtgcttgg tttatttgct ggaattctag    5820
cgggggagct ggcgttgtcg gtgctaattg ctgcggggga gctgctggaa ttcgtgcttc    5880
tgcttgggaa ttagaaggtt tgggttttta tgattcagag ggctgtagag ctcttgagat    5940
tggctgcgaa aattcgggat ttgatcaact tagagagcat tatctttgga ttaggaggga   6000
tttttttcttaa ttttttcttag ttttttttga gctatcaaga gttcatgcca tcttatttct 6060
cccctttgttc ttagccggaa ggatacacga atcagttttt tttttttaaa aaaaatattt  6120
atctcaattt tctgcaagca tgttcaattt ctaagtggaa atgctattta aaagaccagg   6180
cttattgatt ggtgctatac tttgattttc tttggaattg tagtagaagc atcagtttct   6240
tcatgctgtc ctaccaacct ctcttattat tagcaaagta aagttattaa atttgctaat   6300
tgttgatatg tcagtatttt gtacgaattg tgaaatagtt aattttcaat aactacacac   6360
catggttgtc ctgttgttgg actggaagca ataagggaat attccatttc tgtccattaa   6420
aacccacaaa gatgaccctg tgctcatctc taccattgcc atgcacctgt tgtaggatt    6480
gcctaaccca gaagttggtg cttcgagata gccatggcca ccggagtggc accagcgccg   6540
ctcccacatg tcagggtccg tgatggtggc atcggcttca cgaggagcgt cgactttgct   6600
aagatcttgt cggttcctgc tactctaagg gtgggctcat caagaggcag ggtgcttgtg   6660
gccaagagct caagtaccgg ttctgatacc atggagctcg agccatcttc agaaggaagc   6720
ccacttttag gtataactcg ccggctgttg ttcaccttgc atgtatattc gtgttagttg   6780
ttcttagtgc ttttaactga atgaacattt tttctgtaaa gaatctgaca gcatgtctt    6840
tgcccttttg ttattctttta gttcccaggc aaaagtattg tgaatctata tatgagacaa   6900
ggaggagaaa aacccgcact gtg atg gtt ggg aat gtg cca ctt ggc agt gat   6953
               Met Val Gly Asn Val Pro Leu Gly Ser Asp
```

```
                    1                   5                      10
cat ccc att agg att cag act atg acc acc tcg gat acc aag gat gtt     7001
His Pro Ile Arg Ile Gln Thr Met Thr Thr Ser Asp Thr Lys Asp Val
             15                  20                  25 gct aaa acc gta gag gag gtacactcct atttgaagtt ctatgtttta            7049
Ala Lys Thr Val Glu Glu
             30 gttttaatt ctatgcttga ataattgaat gctgggcatg cattaatcat gtgttctttt    7109
agatgttcta tgtttcatga ctagtgaaat aacgaagtat agcactggtc cag gtt      7165
                                                         Val atg agg ata gca gat aaa ggg gct gat ttt gtt aga ata aca gtc cag     7213
Met Arg Ile Ala Asp Lys Gly Ala Asp Phe Val Arg Ile Thr Val Gln
     35                  40                  45 ggt aga aag gaa gct gat gcc tgc ttt gag att aag aac act ctt gtt     7261
Gly Arg Lys Glu Ala Asp Ala Cys Phe Glu Ile Lys Asn Thr Leu Val
50                  55                  60                  65 cag aag aa  gtaagagtca tcattttcc agattcagtg agttttcatg              7309
Gln Lys Asn aatgaattct catcttgctt ttgcatttca acag t tac aac atc ccc cta gtg     7362
                                       Tyr Asn Ile Pro Leu Val
                                                       70 gct gat att cat ttt gcc ccg aca gtt gct tta aga gtg gct gaa tgc     7410
Ala Asp Ile His Phe Ala Pro Thr Val Ala Leu Arg Val Ala Glu Cys
75                  80                  85                  90 ttt gac aaa att cgt gtc aac cca ggg aat ttt g gtgagtgaaa            7454
Phe Asp Lys Ile Arg Val Asn Pro Gly Asn Phe
            95                  100 taatgatgtg tatcatttta gtgtcaatat cttatcaact ctgtgcatat gctgagaact   7514
ctacttgcag ct gat cgc cgt gcc caa ttt gag cag ctt gaa tat act       7562
              Ala Asp Arg Arg Ala Gln Phe Glu Gln Leu Glu Tyr Thr
                                105                 110 gaa gat gat tat caa aaa gag ctt gag cat atc gag aag gtt cca aat     7610
Glu Asp Asp Tyr Gln Lys Glu Leu Glu His Ile Glu Lys Val Pro Asn
115                 120                 125                 130 atc tca ctc ttt agt gtt aat tta gtcagtaaga atgtgcagta tgtttcctta    7664
Ile Ser Leu Phe Ser Val Asn Leu
                135 cttgcatagc cacttccata tcatttcag gtc ttc tcc ccg ttg gtt gag aaa     7717
                                 Val Phe Ser Pro Leu Val Glu Lys
                                         140                 145 tgc aag cag tat gga aga gca atg cgt ata gga aca aat cat gga agt     7765
Cys Lys Gln Tyr Gly Arg Ala Met Arg Ile Gly Thr Asn His Gly Ser
         150                 155                 160 ctg tct gac cgc ata atg agt tac tat ggt gat tct cca cgc gga atg     7813
Leu Ser Asp Arg Ile Met Ser Tyr Tyr Gly Asp Ser Pro Arg Gly Met
             165                 170                 175 gtattatttc ctttctgggg atttcattca ataactttt cgtttcatgg atgtcttcaa    7873
ttaatgatcg ttttgataga tgaatgacat gttctacaaa aatttcag gtt gag tct    7931
                                                     Val Glu Ser
                                                             180 gct ttg gaa ttt gcc agg atc tgt cgg aag ctg gac ttc cat aac ttt     7979
Ala Leu Glu Phe Ala Arg Ile Cys Arg Lys Leu Asp Phe His Asn Phe
                 185                 190                 195 gtg ttt tca atg aaa gca agt aac cct gtt atc atg gtc caa gca tat     8027
Val Phe Ser Met Lys Ala Ser Asn Pro Val Ile Met Val Gln Ala Tyr
             200                 205                 210 cgc ttg ctt gta gca gaa atg tat aac cta ggg tgg gat tat cct ttg     8075
```

```
                                                            -continued

Arg Leu Leu Val Ala Glu Met Tyr Asn Leu Gly Trp Asp Tyr Pro Leu
    215                 220                 225 cac ttg gga gtt aca gaa gct gga gag ggt gaa gat ggg agg atg aag        8123
His Leu Gly Val Thr Glu Ala Gly Glu Gly Glu Asp Gly Arg Met Lys
230                 235                 240                 245 tct gcc att ggc att gga aca ctt ctg atg gtaattgcat ttttactttg          8173
Ser Ala Ile Gly Ile Gly Thr Leu Leu Met
                250                 255 tgtattatat tgcatatatc atatctttcc atctgcaaag ggtaagcatg ccttatgtct      8233 tcctttttgtt gtcttacag gat ggc ttg ggc gat aca atc cgt gtc tcc ctc      8285
                      Asp Gly Leu Gly Asp Thr Ile Arg Val Ser Leu
                                      260                 265 acg gaa cca cct gaa gaa gag att gat cct tgc cgg aga ttg gca aat        8333
Thr Glu Pro Pro Glu Glu Glu Ile Asp Pro Cys Arg Arg Leu Ala Asn
            270                 275                 280 ctt ggc aca cat gcc gca gac ctt caa ata gga gtg gtaacgattt             8379
Leu Gly Thr His Ala Ala Asp Leu Gln Ile Gly Val
        285                 290 attaccttc tctagtttta cacttttctc ttgtttagct gccaatgcca cacattaatt       8439
ttgactattt ttagtagtgt tttgttctat tgttcttttt aagaatttct atttatatac      8499
attatatgtt ctcag gct cct ttt gaa gaa aag cac agg cgc tat ttt gat       8550
              Ala Pro Phe Glu Glu Lys His Arg Arg Tyr Phe Asp
                  295                 300                 305 ttc cag cgt aga agt ggt cag ttg cct tta caa aag gag gttagttcaa         8599
Phe Gln Arg Arg Ser Gly Gln Leu Pro Leu Gln Lys Glu
                310                 315 ataactcct atagtccata gttatcataa aaacaatagt gctagatttc ttattagttg       8659 cactatgac agggtgagga agtagactac agagggtct tgcaccgtga tggctctgtt        8719
ttgatgtcag tttccttgga tcagttgaag gtaactcaca tatttgttac ccttttgtgc      8779
aatgtgttga tcttgtgtaa ctttaccaaa atatatttca agacaatagt ctattttgta      8839
atatacaatt ctacaacatg atattttcag tagccatgtt ccatgcattc tatgcatagt      8899
tcatagtaca tagtgagaat agcaatagca aaaagaaggc attgattttt ttctatctga      8959
atcaaatcaa ttgatgcatt ttgtaatgat ggaaggctct cttattttc ag gct cct       9017
                                                         Ala Pro
                                                         320 gag ctc ctt tat agg tct ctt gct gca aag ctt gtg gtt ggc atg cct        9065
Glu Leu Leu Tyr Arg Ser Leu Ala Ala Lys Leu Val Val Gly Met Pro
        325                 330                 335 ttc aag gtctgatcct tatagctgta cattctagca aacaactaaa ctttattggt        9121
Phe Lys acttcagtct aaactgatgt taattttct atgaatatca g gat ctg gca act gta      9177
                                              Asp Leu Ala Thr Val
                                                      340 gat tct att ctt ttg aag gag ctc cca cct gta gaa gat gct caa gct       9225
Asp Ser Ile Leu Leu Lys Glu Leu Pro Pro Val Glu Asp Ala Gln Ala
345                 350                 355                 360 gtgagttcct tcaacattat ttgttctttt cacaaatcac aagcttatat taacattcta     9285
ttcctttaaa attttttgtgt tgaaatctgt aaaatggtac ag agg ctt gca ctc       9339
                                                 Arg Leu Ala Leu aaa aga tta gtt gac atc agc atg ggt gtg ttg act ccc tta tca gag       9387
Lys Arg Leu Val Asp Ile Ser Met Gly Val Leu Thr Pro Leu Ser Glu
365                 370                 375                 380 caa ctg aca aag cca ctc cca cat gca att gct ctt gtc aat gtg gat       9435
Gln Leu Thr Lys Pro Leu Pro His Ala Ile Ala Leu Val Asn Val Asp
```

```
                    385              390              395
gaa ctg tca agc ggt gca cac aaa ctt ttg cca gaa g gtagacattt        9482
Glu Leu Ser Ser Gly Ala His Lys Leu Leu Pro Glu
            400              405 gaatttgata atgatctttg ttgttttgtg aattgtgttt atgtcatttt ctgtattta    9542 acatttgct tagtctgttt tattgatgaa tcttttttt atgtag  gc act aga        9596
                                                  Gly Thr Arg
                                                        410 ttg gct gtc acc ctt cgt gga gat gaa tca tat gaa cag cta gat ctt    9644
Leu Ala Val Thr Leu Arg Gly Asp Glu Ser Tyr Glu Gln Leu Asp Leu
            415              420              425 ctt aag ggt gtt gat gat ata aca atg tta ctg cac agt gtt cct tat    9692
Leu Lys Gly Val Asp Asp Ile Thr Met Leu Leu His Ser Val Pro Tyr
            430              435              440 ggt gaa gag aag act ggc aga gta cac gct gct agg ag gtaagtgaac      9740
Gly Glu Glu Lys Thr Gly Arg Val His Ala Ala Arg Arg
            445              450              455 acagtaggcc agttaatacc actccctcca ttattaccat ttgttgggat gaaccgatag  9800
tcaattctaa gttacacatt aagcatgaaa atgaaaatg gatttgactc tgcagaaaac   9860
tgacatacag accaatgttt ccacctggtt ttccattgtt ctgtacttct ctttacctaa  9920
aattttattt tttttaataa tgttttgcag g tta ttt gag tac tta gaa acc     9972
                                  Leu Phe Glu Tyr Leu Glu Thr
                                                        460 aac ggt ttg aac ttc cct gta atc cac cac ata gaa ttc ccc aaa agc    10020
Asn Gly Leu Asn Phe Pro Val Ile His His Ile Glu Phe Pro Lys Ser
            465              470              475 gtg aac ag gtactatgaa gtgcttatta agagatgcat tgaccgccca             10068
Val Asn Arg
480 tccttacccc ttgaaattac tgtaccttta ttctcttgtg cttatttgag ttaaattata  10128 tgcag a gat gac ctt gtt att ggt gct ggg gca aat gtt ggt gct ctt   10176
        Asp Asp Leu Val Ile Gly Ala Gly Ala Asn Val Gly Ala Leu
                    485              490              495 cta gtt gat ggt ctt ggt gat ggt gta ctt ctt gaa gct gct gac cag    10224
Leu Val Asp Gly Leu Gly Asp Gly Val Leu Leu Glu Ala Ala Asp Gln
            500              505              510 gaa ttt gag ttt ttg agg gac aca tcc ttc aac ttg tta cag ggc tgc    10272
Glu Phe Glu Phe Leu Arg Asp Thr Ser Phe Asn Leu Leu Gln Gly Cys
            515              520              525 agg atg cgc aac aca aaa acg gtaagctgat gaattcttct ctgttagact       10323
Arg Met Arg Asn Thr Lys Thr
            530              535 gtagatccca tgaacaacgt caacctttaa ctcgtgagat atcatgaaga agtgcaaaat  10383 tgcacttta acagtaaatg aaccttatag cctaccgaag aggataaata actttaggca   10443
attctctctt gtgaagcaga acattctttt ggcgatttct gaccgttaat taatgctgca  10503
ggaatatgtc tcttgtcctt cttgtgggcg acactctttt gacctccaag aagtcagtgc  10563
tcagattaga gagaagacct ctcatctgcc aggcgtctct gtaaactctc ttacagacct  10623
tctgcctccc ttgttttcaa tcgcatatta gctagcctga tggctaatca tgtctacatt  10683
tgcctggcag att gct atc atg ggt tgc att gtc aat ggg cca ggg gag    10732
            Ile Ala Ile Met Gly Cys Ile Val Asn Gly Pro Gly Glu
                            540              545 atg gcc gat gct gat ttc gga tac gtt gga ggt gct cct ggg aag atc    10780
Met Ala Asp Ala Asp Phe Gly Tyr Val Gly Gly Ala Pro Gly Lys Ile
            550              555              560
```

```
gac ctt tat gtt ggc aag gtaacctttt cctatacttg tggaagttga         10828
Asp Leu Tyr Val Gly Lys
565                 570 atcatatcaa atggaataat ggaaatcacg gtatatcgtt gaacatagct gcaagtcaat 10888 atttgtacat gatcatgcaa acacaatcaa cagtagggat gttaactgca tggcatatat 10948 atgctctttg agctgaaaca aaaacttaga gctgccattt tccttccatt aacacaagtt 11008 ctacttgttt tgggtgcag acc gtc gtg caa cgg ggc att gca atg gag ggg   11060
              Thr Val Val Gln Arg Gly Ile Ala Met Glu Gly
                                575                 580 gcc act gac gcc ttg att cag tta atc aag gac cat ggc cgt tgg gtg   11108
Ala Thr Asp Ala Leu Ile Gln Leu Ile Lys Asp His Gly Arg Trp Val
            585                 590                 595 gat cct cct gtt gag gag tag gccgtagcat gtagttcata tatgtactcc     11159
Asp Pro Pro Val Glu Glu
            600 tccataaaca atgttgtagc tgaggcacat tgtattgtat ccacggagta cataaataca 11219 cgttctgtac atcagtttag aaataaagta ggaatagggg tggctgcaac tttgtaacac 11279 cctcgtgaag catcggcaaa tccaaattag aagcgtcctg aaatcagtga aaagaattg  11339 atactgctat tttttgtacc aattgaaaaa aaaaaggaat acatgatatg actaaatcat 11399 gggttacatc ttcgtcaaaa aatgtcacag cttacattat tttcactact tgcaaatacc 11459 agacgatcta ctggtgcggg aacttgacgg gtgcaggaga cgcgaagccc ttgtggtaga 11519 gaagctcggc catgacgctg tacgcgcgct gagtcaggtg gacgccacgc catcccagct 11579 gatctgctcc atctcgaagt tgtacttccc gccgcagcac gccttggtca gcgccacgcc 11639 gtcgaacccc gtgtcgcgcg cgccctccag catccgcacg tacgcgccgg agtagtcggc 11699 gtacgcgatc gtggcctccg gttatgaccg cctcagctcc cggatcccct gctgcagcag 11759 cacgttgtgc atctgcgcga acaggttgag acccacgagg cacccgttcc cgtcgtacgc 11819 cgcgcgctcc gtctcgtcca ccgccgccag gtagctcggc gcgcaaccca gcgggaagtt 11879 gcccgggatc accaccgcg tcgcgctcat ctcgagcacc tccctcgccg cgctcaccac  11939 gcgaccgcac cacctctggt acgagcacca ccgactccac cacgccggtc atcatgcgcc 11999 cgacgtccgc gcggcgctac gacctcctgt tcgcggcctg ttcgcggcga tctctcccac 12059 catcaccagc aagctcgcgc cagcttctct tgctcgagaa ttttcagaat atgccaccga 12119 atatgcaccg ttttcaggat agaccactca attcgcacta ctttcataat atggcatttg 12179 gacgcgatat tttcttcgtt ccgtgacact ctcatccttc caccgtcagc gccagtaatt 12239 ccgttcgcac accaacagct ctctctgagc gtccagctcc agtgggggag ttgttggtgc 12299 gcggcgcggt aacaccgatc ctcgcgaggg ccgccgcgtc gagggcggtg gcgccggtga 12359 cggcgaaagt tgacaccgta ggagaagtcg gcgcctttgt cgatgtacgg gttgagcagc 12419 ggcagcccta ggtcgttggc gaggtagtcg atcatgaggt acccgtcgtc ggagcactgc 12479 cccgtggcgc tgccgatggc cgcgccgtac gtagggaggc gccacggtgt gctccatcaa 12539 ggcgaggaag ttgccggtgt ccgagatgga gtccccgaag ttgtagatgt ccgtgatgcc 12599 gtccaccacc gccccctcg ccgccgatga caacgacgac gacgcggcct tccccggagc  12659 cggccttgcc tggcaagtgc cgacgaggag cagcgccaag aacgcgacga ggattggatg 12719 aaccggccta ctcgccatgg cgctcggtgc aagtgcaagt gggtgcgacg cagcagttgt 12779 tgtggcatgg cgcgcgcgcg gtgtggaatt cgattggaaa cgatttaagc tgagacatag 12839
```

```
tccaactccg aaacccaaat taaccataca tacagtgata caggtgaatc gacgagatga   12899
tcatgcacta cttaaaaaaa accgtcaaaa cacattttg taggcggtca aatactctat   12959
gtacttaaag gcctgcgaaa ataacgcccc aaaagtcgtt tcttagtagt gatgcatacg   13019
caattgctgc aataacttaa aaagggtgat ttttattgca tcaacgtaac acgtacactg   13079
cattagtcct cctacattga aagcacaaat taaaccagta tggttgcaac ttgagacaca   13139
caaaggtgat cgatcgagaa ggttagctat aaacagcacc ccaaatggca cgaattaata   13199
atgtagttct ttctgcatgc tgaccaaaat ttcattttct ttttctctcc cctcgtcatt   13259
aaaaaaaagg tttaaagaca gaattacaag ctaattaatc atcagtggat cgagaattaa   13319
ttaagggatc acaatggctg caccccgcta tttcggagta gctagctcca tgcactcact   13379
catgcatgca ggcatgcata tacatgtccc ttgccatgtc ctatctaaca atttacacat   13439
ttcgacaaaa tgctcacggt cgatttggat tgtgtcactg acattaattg gttcatgcat   13499
ccacgcatgc gttactctca aggaaatatg aaagtatcat ccgtaatcag ggttccaaac   13559
taaggataga tacctttcan nnnnnnnnnn nnnnnnnnnn nnnnnnnnag gcctgctgca   13619
gcaagtgcac ttctcctgct catgcttcag agcctgcacg cagaaagacg acacaaaatt   13679
caaaagttta tatcgcttct gttttggagc ctcggctaaa aaatgaaaat atgaacaacc   13739
aaaaaaggca acacgtacga gttctaacca agtatataac cattataatg gcaaatgtga   13799
tctatacttt tgtagacgaa gacaattaat gatagtacca gtgaatatgc tagctatata   13859
cttttatcaa ctacttatcc gatcaatatg cttcagcatt acaaactagt tcttatatat   13919
atatttcttc tatcttattt catctctaaa atacaaagtt tatagtgtaa agagatcccc   13979
agggatgaat atatcttcta acacacctcg tagttaattt gttccaaaca atactagcat   14039
gcatataatt tgtagttatt tgtagcaaag cacggctatt tcgctaacaa atctaaatag   14099
aaaatatgtt atctctcagc cttgagaggt gtattaatta ccagcccata catcacttga   14159
gagggaaaag atttaaataa gacaaattga ttagaacaaa agggaatgat agacaatgtc   14219
ggtttttttt cgtttcttcc tttccttcgc ataggctcgt ctagctggtt gcgttatgta   14279
acaaaacctc ttttcctttt aatatattga tgggcgcgcc ttttgcgcat tcacgaaaaa   14339
aaatgtaaat gtgaattttc aatcttatcc cctacttgcg ggattagtcc ttgtgaagaa   14399
atcctcaaat atgcgtacct gcagctggct ctgcagaccc ttgatgtgct caactgcaag   14459
gtccaacatg tccgctgtgc ttgtttgctg ttgcaacacg aacataatta attactcaat   14519
tggttgcatt attcatgcgc aaaaaatgtt accgctaatt aatattagct agaactagat   14579
gagagaacgt acgacccctt tcatctatat acaataatca tgaatttgtt gagaaagcat   14639
gtttggtatg gtgttggagt tgtggctgtc atgcaccaaa gctctaatct cagtgcctat   14699
agaatttaac tacacaaaca tggatacgct ttttctagaa attctattag gttatgattt   14759
tgcgcttggt gtccatgaat ttgttgagca tgtgttaagg gacacttcac agtgcacact   14819
catgggtgaa tgcgtgtgca tttgccatgt ctattattaa ggcgagaaac atgaatctgt   14879
gtgctaatgg cacaagaaat gtggaaagtt tttttttaaa agaaaatact tagctaggga   14939
tgttcctttc ttcctcaaat atcatgtaaa tataggtatg aacattatgc aaagttcaaa   14999
tcgtaatggc caccttgtcc atgttgggca ccagctcctg cagcttcctg agcttctcgc   15059
taattctcgt cctccgttcc tacggacgcg catcgatcac accgacgtac atgctcatgt   15119
gtcaagatct gaagagaaag caaaagcaaa tatagaggcg ttttgatcat gatattgcgt   15179
acgtaccctc tccgcgatgc tcctgggggtg cgtcgcgcag ccgcgcttgg cccgcacttt   15239
```

```
gaacggcacc tggtcatgct gcagctgcag gtacctgtcc atgccggcca tctccagcgc  15299
cgacgtgctc gccatgccgc cgaactgccc ccatttccaa cacgcccaag aaatcagaac  15359
acatcgcgat atatatatat atatatatat atatatatat atatatatat atatatatat  15419
cacaaacaca gcaaagctag ctactacttc ttcctctgtt ttacattaat tattataagt  15479
tgttttgagt tttgaataga ttcatacatg tataaatgta tgtgtttcat acatgtgtcc  15539
aaattcttat gaatgttagt aaatataaac aagggatgaa gagatcaaga agccttgtag  15599
tgtacaatga ttcaatgaag gtagccctag caatcaaatt tgccgagcaa tctttacctg  15659
ggactcgtac ccgccgaggg tggagatgat gtccctggac tcctcccacg gcccgacgat  15719
ggagaacccg ccgccgccgc tgctgccgcc ggcggagaag gtgcggggca cggaggcctc  15779
ggcgccggcg cggtcgggga aggcgccgtc ctccgcgatg tgcgagaggt gcggcggccc  15839
ggccgtgaag ctcagctggg acttcatctt cctcccgccg ctgctgctgc cgctgccgct  15899
gccggccatg gaagggtggt ggtgggcttc ggctccgctg cctcccccgc cttttgagcc  15959
tggaaagcct gcttagttta ttgccaagta gcaagcacgg aaattaacta atgatcgcta  16019
attagttaaa ttaactgtgt gtgtgagaga aagagctact gttacccaaa cgctagttga  16079
aaactgccaa gtgtgacaag taaacaatag tttacggtat tagcataccg ttagagctag  16139
ctctataggt acacgtgttg agcaataagt ttaacctaga tgtgatggga tgttcaaact  16199
tgcttctcca aggttgaatg gagtagtgtg tatttgattc tacaatattt ttctgtagta  16259
ggtgcacgta attaaggtta ggtttgattc tcatgttcaa atgtgtgttt aactgcaggt  16319
gtaatgttat atatgcatag tggttctata aatattttca taattaaaca ctaccaaatt  16379
tctatttgaa atccatgtac aaattaaact tgactaatca ccggttatta tagttaaaca  16439
taacttaaac cacaacaatt accattcatc aacactatgc actactaact aattaaaaaa  16499
aattacaagc tagcactacg aaattaaaag tggcccggcc gagttgcccc agcacaaaat  16559
agcacgatag atacaggata tacttcctcc gtttctaaat attttacacc gttaacttt  16619
tagcacatgt ttgaccattc atcttattca aaaattttg tgaaatatat aaaactatat  16679
gtatacataa aagtatattt aacaatgaat caaatgatag gaaaaaaata atacttatt  16739
aaaattttg aataagacga acggtcaaac atgtttaaaa aagtcaacgg catcgaatat  16799
ttagaaacgg agggagtata tgagaggaat attctcgtga ctagaaccat atgttccaga  16859
aagttgtact ccatccattt taaaatgtaa ggtctatttt gagtggtcac aagtattaag  16919
aatatgaaac ttacagaaag atgagttcaa acgaccacct taattagaaa gagtagtaga  16979
tcgttagtga gacgaatatt atatatatga aagagacaaa aacaattaaa attagtgttt  17039
gcatttgcgt tcatctttac tagctattac tagttactta taagcacatc gtcaaacatg  17099
tacttacgtg ttgcaactta atttctactc cctccaattc agtattggtc gttttggatg  17159
aaaataatat caaagttagc aatccggccg taaccatttt ttcaaacctt gtatgccaa  17219
tagttacatc gctattcaaa tcaaaggttt caaattttgg attactattg gtcccaata  17279
gaagcccaaa aagtatttga atttttaac ttaggccccg tttagttccc taaattttt  17339
ttcaaaaaac atcacatcga atttgtgaac acatgcatga agcattaaat atagataaga  17399
gataatccct catatgccac taaaaattga tctgatccct tatatgccac taaaaattgg  17459
ctcctccctt atatgccatt ggtctaaatt tgcgtaccct ctcatgtcac taccgtcagt  17519
tgaccgtgtg ttgaccgtta actctcaagt aaaaaagaca tattgccctc tctgagttgt  17579
```

-continued

```
taggcatgcc ctatactcag aagggtaaat acgtcttttt tccttaagaa ttaacggtca    17639
acacatgtca actgacggga gtggcgtgag agagtgtgca aatttggatc aatggcatat    17699
aagggaagaa ctaattgtca atggcatata agggattaga ccaactttcg gtggtatata    17759
agggattctc tctataaata aatgaaaaat ctaattgcac agttagggag gaaatcgcga    17819
gacgaatctt ttgagcctaa ttaatccatg attagccata agtgctacag taacccacat    17879
gtgctaatga cggattaatt aggcttaaaa gattcgtctc gcagtttcca tgcaagttat    17939
gaaattattt ttttcattcg tatctgaaaa acccttccga catccggtca acatccgat     17999
atgacaccca aaatgtttct tttcgcaaac taaacaggcc cttagcaaaa tggttggtta    18059
tcaactttta aaatatgttg acagtgtctg tgacgacttc atgacggtcc tctttaaagg    18119
tgcttatata gtgatagggt gtgcgtgtat gttcagagcg ttgagtatgc atgtgtatat    18179
atgcatgttt gtgtctgtac tgtgttaaaa agaaaatcc caagatctag cctaaaattt     18239
tcattaaaaa cattgaaatt ttggccccac gatttttta ttccacaatg taaatttcta     18299
gtcaaattgc tgcgaatgac gcgaaaatta ttttctgacc agtgaactga catgcacaca    18359
ttacactata tttattttat atttattttg aacgtaccta cgactacttc caggggatcg    18419
atcttattct cctcaaatta ataagaacaa gtactctctc catttcaaaa tacaacaacc    18479
taagaatatg gataattttc ttcattgaat cggatggttt cttcggtttt tttgtactac    18539
gatgcgaaca gatggtatat tgaagcctac cggacacgct agcacgtgca tgccgcgtgc    18599
cggcccgtgc atatgagcaa gcctcgcacg ctgacataga cgcagccaag agagaaagca    18659
aacgccaaat caagaagccg agcaatcacg catgccatct caacgcaccg taggtcacta    18719
tctttagcga ggcaagaccg tgacgtcacc gtcaggccat cagcagagga gctgaacctg    18779
gacaaaccgg ggggcccacc ccgcaggcca agttgcggcg acacacacgt ggtccccgcc    18839
ttacattaag gcaagtggcg ccctaattaa tccattgatc aaaaattaat taatccacaa    18899
attaatcaaa tgccctcatc ttttctttt tgccttggct agggttcgag gcactaagat     18959
ccactggtaa tttaattgtg cttgctgtct tgatactaat taattgatca tatatgcgca    19019
agttggtcta tctagagcag aatctagagt gcaactggct gccgcattga aagaaatgct    19079
gctacatggg ctccactgaa agacatttga ctcttttaaa ctttactcga ggctattcct    19139
acctcgatca aagtataatt actaaattta gtactggtgt agtacttata tgtggatttc    19199
gacatttcta ctggtactat ttttatccttt accaattgtt gtatacaggt tgctcggtca    19259
aaaggccatt ttagatgttg gtatatatgt agtgtgaaaa ttaattataa cataactcta    19319
tgttcatatt gatctgcatt tcaaaaagat attgacacac ttattcctaa tttttgaata    19379
aatgatattt tgaagttttc attaaagggt tattatctct gtatgctcta aaacgttgaa    19439
tatttgtgac gcagaattaa tttaatactc atggaataaa taatgatggt gcataatttt    19499
gcaatgattt tcatcaaatg aggtgcatat aggtatcctt tatatgaaat gagaatactt    19559
gccaaaaaca ttttttaaaaa gagcttgttt tagctagcta ggttggtgaa tggtgatact    19619
aattaatcaa atgtacatat ttgtgcaaat cctggaagat gaatgcatgg ttttctagtc    19679
ttattatgaa caaattaaat tagaaaaaaa aacatctatc tctttgctct ctccactata    19739
gcttcaaatt gttttttttc cccatgtcta ctattgtagt gaagaatgga ttgtcatgcg    19799
caatgacttt gcaactgaaa ataatggatc aaatgagaga gagggacacc aggtgcaagt    19859
ggcaaaaaaa ctaagccatt tatagcaagt tgcaatagaa aataagacaa tctagagaca    19919
ctcgattata aaaagcgtac gtaaaaagaa taaaagcggt gtattcaaaa ccctagaccc    19979
```

-continued

```
cacatttcac tatcgatgat accctacttg agaaaacccg cctcctgtgt agcccatagt    20039
tttccatcgt ccttcttaca cgccgagcca aatttgtgca ctcctcgtaa taacatatgc    20099
cttaaaaact tgaactcata ttacattatc acgaaaacaa ttaagccgca taatctcatg    20159
gatataacat ctcatggtgg atccttaatt aacagcttat atatatatat atatatatat    20219
atatatatat atatatatat atatatatat atatatatat tgaccctaac tgtggcaaac    20279
atgcattatt atcacacaaa agttactaac cacatatagg agcctatggc taatggctct    20339
gagtagaaaa atgggcacag aggatctcca tgatactatt tatggcaact cacgtagcaa    20399
aaagccgcag actaacacat ccatggatat ccacaacgca tactgatagt agtctgatat    20459
acacactagc tcctcccatg acggccttag cgaaaaccac ttttttaaccc aaaaaaaaaa    20519 ccagttagga ccggtgaaaa gtcgcacgcg atgatcgatt cacgcgcgcg ccgcagaagc    20579
aacttgcaaa agggatcgag cttagctaga tagcgcgagc tcatcagcat ttcgtcgtcg    20639
ccgagcgagc tagtggcttt ggcagttagt agtgatggga gttgcataga agttaagaac    20699
caggtagaca gagatcgatc gattgatcaa acccgtttgg tttcggataa gtatgggaag    20759
aatctgaaac agtgtggagg aaacactgag agagaaagaa caccattaac aataatatcg    20819
atggaattcg tttttttttgg tggttgttgc tagaagccta aacagcaat tcatgtgatc     20879 gatcgatact tcgatcgtgt gcgtgtgtga cgagaaagag atgggcatg tgaaggcaaa     20939 gacgaggttg acatttgcac agctagccgt tctctcctga cagaattaag ctagaaattg    20999
aagatccgtg actctgagta gtcctaacca attagctata cgcctataca cgatgggcta    21059
gctatgcacg cacgcgacgc caaattgaac acggatgaac aaataaaatc gaacaatggg    21119
ttggctagcg caatcgatcg atcgatctta ccgttgctgg ccatgaggtt ggagaagaat    21179
ccggccggcg agctgctgtg ccgcgccagc aagtccacgc tcccgtcctg cagctgatgc    21239
ccatgccctc cgcccctcc gccgccgccg ccgccgccgc cgtgcgggcc cagcgagatg     21299 tccccccac cgaaccgcag ccccgccgcc tccgcctccc ttggctgcgg cgtcgtcgac     21359
gacgacgacg gctccacccc tcctcctcct cctccccca ccggcagaaa cctcctcatc     21419 ataccctcc ttggatcgat cgatcaactc cacccccgc gaccgagacg cggcctctcg      21479
tcgatcgatc tgcagctcgc gcaggcgcag gtaggcaggc ggcgcgtggt gtgggtggaa    21539
atttcggcgt gaaaattaac aaaacgacgg gggcggccta tactatagct agtagaggag    21599
agaagagggg aagggaaggg aaggggagg tgaggtggtg gaggtggtgg ggctaggcgc     21659
aagtgggagg agagggtggt gggattttaa agggaagcga ggccccgtga ttggttctcg    21719
gggcgtgtgg cgccgtgggg accagcggac cggccgggcc cgggcaagtg gatgtctcgc    21779
gcggagtgga gtgggcttct gcactgcgca gcagcagcag tagcaagccg taggtggcgt    21839
cgcgcgcccc gccccggaac cggcaggcat ctctctcggc ttttcgctgc atctttggtg    21899
ctagattttt gtgttggata tatgatgctg atcgaggaaa gggaaggaag aagaaaaaaa    21959
aaaggatttt tttggtgtgg cttagatttt tggatgcttt cttt cctctg ctgcggactg    22019 cggggactag aggatgaact cgataatcaa tggtggtggc ggcaaatgtt tatacttcct    22079 cagtcttta tatttacctt ttgtgatatg gaggaaacaa gctggtttgt ggtgttgtgc     22139
actcgtagga ggggaggtac gtagttaacg gcaaagatcg atcatgcaag ttggttgggt    22199
caatttggtg gtcgagctga cctatgttcg cccatcctct cgatactttt ctcatctaga    22259
ctttttctac gacgctaaca gactgattat cacagtcatt ggatagatcg acatggtcat    22319
```

```
ttgaaattgt tcgatataac tggtttaagt tcaaacaaat ccaagctaaa ttttattttg   22379
cggaaaaaat gtttgaattt cacttgtttt caaccgttat tgctgttagc gaccttgccg   22439
ttagggagcg ttttttaac ctcggcacat ccgtaaactc tattgcaggg gagtcatgtg    22499
tatgtctaac agtagtataa ttttatcaca atgatttgtc tctttacgag ttgtattata   22559
aactcacggt gttccccgca aaaataaaa ataaactca cggtatgtgt aaatggaatt     22619
aggtcaaaat ttaggaatga aatgaataat caattgggtg tgaatgggtc aatgcactaa   22679
accatatgtt ttgctcacta gatatgacaa ggaaaaaccg aaccatcaat aacactggaa   22739
accatgtttt tgtggtgacg cttagttaac tcatacatca attataatct tttctctatc   22799
caattccact ttggtctatt ttgtctattt gaaatcatgt ttcagctatc ttctaagtaa   22859
agcaaacttg aaaacctagt acatctaaac ctagctccac tagtgtggtc caaaagcagt   22919
ggagtaatat cataagagga agacaacaaa aaataggata gagatagtct tagcttgtgc   22979
cgcagtaatt cattcgatag attattagta attcattcga taagatatga taatgatgaa   23039
atgattcggt cgcacggtgg ttgtgaagtc ggagccatga tatgtggcat cgaaagcatt   23099
agtcaaacgg acttcggttt tggtcaggta aagttgtgtt ccttggttct taattcttat   23159
caaaattgga gtcgcctgat catgtgtgcg gtggtgtgat gacgaatgac ggcgagtttt   23219
taccaatgta cagtgaactg cgttttgttt taaggctgtt agttttgttg tcgtggttat   23279
gctttgctag ctagttaggg tgattcctat tttttgtcag gtcttatgaa agttaaaaat   23339
atttttaaa atatgagttt ttttattgtg aataatgagg aacaaatgaa gttttgggag   23399
gatacatggc tagaaaacat ggcttttaaa gataaatatc catctttata ttatatagtt   23459
cgaaggaaaa atttatctat tgctaatgcc atgggatctg ttccgcttaa tgtttctttt   23519
agaagagttt tagttggtca gaatcttgta tattggcatg aattgcgtgc ttctattgta   23579
catattcagt tgaatcaatc tactgactat tttagatgga attatcatca aaatggttta   23639
ttttctgtaa ggtcaatgta tctagcctta agccttaatt aataatggtt acattgagag   23699
aaataagatt atttagaaac ttaagatgcc gcttaaaatt aagattttta tgtggtactt   23759
gcttaaaggg gttatgttaa caaagacaat ttggcaaaac ggaattggaa tggcagctta   23819
agatgttgtt tatgtatgaa aaatgagact attcaatatc tttttataga ttgtcatttt   23879
gcaaaatttg tttggggagc gtttcagtac tcttttggtt tataccttcc tactttcata   23939
cattgtatgt ttgatggttg gctttggggg tgaacaagaa aaggagcaaa ctaattcttg   23999
tagaagcttg tactatatgt taggctctgt gattgagtag gaatgatatg attttttgaca  24059
aatcactatc tatttcattt atgcaggcat tcttcagagc aacatattgg ctccggtttt   24119
gggcacaacc gtaaaagtgt gatgaagatg gagagcttt gaaagttata tgtcgtaagc    24179
ttgagacgac ggttatgcaa ctttttgcca actatggatg gagattcaca aatagactta   24239
aataattgtg tgctccttat attggtctgg tcatttttt tatgtttagg tgtgtgttta    24299
attctatttg aactacactc tttgttaagt gctagattgt ataattggc tgtagctctg    24359
ttgagcaaag gccgagatgt tatctattcc attattaaaa aaaagctagt tagtgtattt   24419
attgttgtat ggcggtttta gcccgattgt tctaaatcaa ctgaatatta atttgctctt   24479
ttttagagaa acacccagag gtcttccggc tgggttagat gaccttggtc cttatcccttt  24539
ctaattattt gatattaggt acttcactaa tattcgtatc tttttttaaat taatttgctc   24599
tctttttaaa ctattcatct tttctttaat atagcactaa attaaccgtg atctttcaaa   24659
agaaaaggcg aaaggtgtga atatgcatga aagatcgagt ggacaccccc caaaaaaaaa   24719
```

-continued

```
aaaccctagt tgttgtcacg tgactctcaa agtccatttg aggacttact aactgtttga   24779
aattaatgga taaggctcca gctaagtagg cgggaaaaga tcaaacgtgt tcagtggatt   24839
tataccaaat gtggtccgtg cgacatgttg gtccataaaa gggcatatga aagtttcctt   24899
tcagctaatt aaagccagtg tcgaatactt atacagtata gttttcgaaa taagttttac   24959
ttctacaatg taatccattc acggatgaaa agctgtgcg cccaacagct atagctatac    25019
aactatatct atttgttaat taagaggttc atatcttggg cacacaaagg ttctgtttga   25079
atcttctgaa gataaatatg aagatcaaat gttttacgta aaacgaggtg gtaataactt   25139
ttgattaatt agatttttaat tattacaaac ttaaaaaaaa gattaatctg atattttata  25199
acaactttca tatagaaaat tttcacacga aacgcaccgt ttaacagttt gaaaagcgtg   25259
ccacgaaaat ctagaactta atctgccctt tgttgggttc tcgaacagga ccaaacttca   25319
tgtccatact ccgtactgta cataccaact atactaaata tcgctaaaac gttttaaaaa   25379
tattatacat atactttcaa tactattata cgtatgcgta aagttttatc ctcaaattca   25439
ttatatttca tacttaaaaa aaattctaat agctttatga atataagtct tagattttt    25499 tctccatata tatatatgat aaatttaaag atgggacttc acgcgtatat ataaatacta   25559
tttaaagtac atgtacattt ttctaaaaaa ataatatttg ttagtttgta tacattgtgt   25619
gtatacgtga aggctcacgt agacattttg cactctcaat tatttatact agactaataa   25679
ccacctaaat attgttctta gcggttttga cttgagctta cctacgagat gccaacgtgt   25739
cagtccagtc agcaaaaaag ttttaaaaaa actccgtggg cccacttgtc atacttctcc   25799
ctcaatctaa cgcctccccg gtcaccctac tctctcttcc tcgtgcgcac gctcgtgcgg   25859
ccaacggcgg agtggtgcgg tgttggtgtt ggtggtgcgt ccgcgtcggg cacgacggcg   25919
gtgttgccgg agagatggag ctacgcaaga ggcgggcgtc gacaagtatg gacccccagga 25979 ggtggaggct acgcgcgagc gcgtcggccg cgcccttgc cttcaacggc gacgacagca    26039
ttggccgctc gttctcggcc tcgcctctct gaccgcaggt cggcctcagc ctagcagtag   26099
tcggccacgc acgttggcct cattttcgtc accgtgttct tggggctggc atgcaggcgg   26159
gagaaggagg gatagcggca tggactgcgt gtgcgcctgt gcagtgacct gggtggatac   26219
tatgtcaagt tggagctctg caagtcggcg ctctgcgacg gcgacggcaa cagggacaca   26279
tcgtcgttgt caccgtgctg cgcggcacga gaaagatggt ggcactgacg gtgaggcttg   26339
cgatgacaaa tgtgatggtg acaagggccc aacgtcgagg tcgttgccct ggaatagaat   26399
ccgatcggca gctctagcgg tggcaacggc tcagtgctgg cgctagagta cgagcgcggt   26459
cggtggccac agggcggtac cgcggcgcgc gggaggtgct ccaggcggcg cagtgctccc   26519
cccgtgagaa cgagcggttt agcatcatgg ccatcgtcgc gcaccgtcac cgccctgggc   26579
ttctctagcc gaccacgctc cacctcaagc aacccgggga gtagtctttg ctgccaccgc   26639
ggccttctcc tcactgctcg gttcaaggat gagagagaga tcgaggtgga aggaggtaga   26699
agagatgagg tgagaatata tggatcactg acaagtgggc ctgttatttt ttgccgcgtt   26759
agaaatgcca agtcagctaa cctagcctaa aaccgtccaa aatagtgccc cggtattcgt   26819
ctggttttaa gagttttgag gtattgaata caatatatgt tattatagtt tagagggtaa   26879
attgtactac cgtaccataa tagttcgggg gtaaattgta cttcctctgt actcataatg   26939
gaagtcgttt aggacaatat ttaagtcaaa cattgggaat ataaatcatg aataactctc   26999
aagttgttga gtttgaaaat gtaaaaatta tatgaataga ttttcttga aaatatttt     27059
```

```
cataaaagta tacatatatc acttttttaat atatattttt atagaaacaa gaagtcaaaa    27119
ttatgttttg gagaccgtgt cgctgtccaa aacgagtacg gagggaatac tttttactcg    27179
tagtttacaa tatcgatctg ttaactgttt ataagagtat ttggatccat gcagtattgt    27239
agtagtagta gcagtacatt tgagaatatt agagtacgaa ttaggtggtg tttggataca    27299
gagacttaac tttagtcttt gtatttagac actaatttag aatattaaat atagactact    27359
tacaaaacta attatataaa tgaaagctaa tttgcgagac aaattttta agcctaatta     27419 atctataatt agagaatgtt tattgtagca tcatataggc taattatgga ttaattaggc    27479
tcaaaagatt tgtctcgtga attagtctaa gattatgaat gagttttatt aatagtctac    27539
gtttaatatt tataattaat tttcaaacat ctgatgtaat agggacttaa aagacttta     27599 actaccattt aaacagggtc actccaatgg taggtgaaat tcaacagctg ggaaatgcac    27659
tagtgcgttg tgtcagtaaa tttcgtacta gtaccacgag acagctagac agacacgtca    27719
ggtcacgacg cagcactgca gcagggctgt agcctgtacg ggaggcgtag gcgcaacatc    27779
tcgaaaattt tgttccgtag ctaaagcccc cccaaagcca gccgcggttt tcatggattg    27839
cacaggcgtt cctctccgcc ggattccgga aagaaaaaag aaaaaacaag atgtccgttc    27899
cctgggtggt gcatccgttt tctgacaggt gcatgcacct ctcgctcgct accgcggtag    27959
cgcccacacg aaccacgttg gctttcggcc aacttgcccg attctttaat cccctcacga    28019
cgtacgtcgc tgtccaataa aaagttttaa caccaactat agtaaccagc ttaattttaa    28079
taaaaccaaa gaaaattctt aattacttag agcatctcca acagggtcct caaacaaagt    28139
ccctaaataa gttttgagag ttgatgcaaa aaaatatagg tccagcagat tccctactag    28199
agcccccaat ctagggaggc ccctagatca ctcctccaag cccccagtcc gggggggctca    28259 accccacagc ccccatcctc ttttttttg gcggggaaa tttctgagcg cgcgccatcg      28319
tcatcctccc tcccgcgtca tcgccatcct cccacaacct cccagcgagc aagccgccag    28379
gtcgttttgc tccggtcggc gaccacccga catccctcgg gaagaaactt cggcgagatc    28439
ccatggtgtg ccgcctcaag ccatcacaat catcggtttt actccgtcac tcactgtcgc    28499
cgacctcctt gcatcttcgg ccaacgcacg tcgtcaccga ttgatcatgc ccaggtgagt    28559
ctcgacgtcc tccccgaact agctgcccac ccgctgtcca caaggcctag cgccgaccat    28619
cgacagctat ctatcaccgg ccgcacacat gctgcagtaa aaaaattcag agatgatggt    28679
gattaaaaca aatcacaata gtaaagttca gtttcgtatg tctgagtctc cttgtttgat    28739
tttgatcttt atgggcttac taggcgtcta ggcccatcta aatcattcgc acagcaaaac    28799
gtacattgtc atcattcatg tttatatgc agtgtcttgt tctatgtcag agagctaatc    28859
ttgcagagca tatataatat ttaagaaata aatttgtgtt tgcactgagt ccttagtact    28919
gcgcaaccaa tatatatgct aaataaatac atattgcaaa cagtataacc tgatgtacat    28979
tgcaatcact tgttgatgtt tctgagatag attggaaagg ttgtcaattt atatatttat    29039
tgcagtgact agattgcaat gacaagtgga ggtgattcct ttgtgcgcat gatgtccgag    29099
gacactgatg tcgaagtgct aatgccaaat gaagaccttc gtacttcaac aaatggtgca    29159
aaaggaagtg ccaaaagatc aagcaactat actcataagg aggacattca attgtgcatt    29219
tcatggcaga gcattagctc agatcctatt attggcaatg agcaaccagg gaaggcatat    29279
tggcagagga tcgcagagca ctaccatgct aaccgtgatt ttgagtctga taggaatgca    29339
aactctcttg agcaccattg gggtaacatt cagaaggaag taagcaagtt tcaaggttgc    29399
tacaatcaaa ttgagcgtcg tcatccaagt ggcataccac atcaagagct tgtaagttaa    29459
```

```
attgtttatt tattattatt aataacaatc ttgtatgtat gtgaattaaa acttaaatta    29519
tgttgcaggt tcttgaagct gaggcattat actcgtccac tgcaccaaag aatagggcat    29579
ttcagtttaa tcattgttgg ctcaagttga ggaattctcc aaagtttcaa acactagaat    29639
cccacaagag gccacggtct aggaagtctt cgaccccaat tgagagagct ggtgaagaag    29699
atgaaggaga tgatgctagc aagagtacag ctcctgattt atctcagccg agtgctaaaa    29759
agagaccaat aggtaggaag caagcaaagg aaaagttgaa gaatggagga caagatggac    29819
catacaaaga ggcgatgaaa gatttgcttg acgctaaaga gaaagaagcg aaattgaaag    29879
aagagagatg gaaggaaact aaggagattc aagagcgcaa gctcttattt gctgagcgta    29939
agttagtgtg ggatcaagaa cagaagatta tgttttgtga tgtttccacc ttggaaccgg    29999
atgtgagaac gtatgtgttg gctatgaggg cacagattgc agcttcaaag gtggctgccc    30059
tcaatggtgg atttgatggt agtagtggct tggaggtga gtttggtggc ggtaatggag    30119
aagtttgagc acttcgatgg aataagttgg attctattgg atgatccatg tgtcctttac    30179
tagtaggata tgccattatc acgattggtc tttggagtcc ttttttgtta attatttcca    30239
caataatttt agtgtcactt gctagtagga catatattac tttcagattt gttatttata    30299
atcgaatcat tcatggttgt aggatgtatt attttaaat tatataatgc atcattgggt    30359
tcacatagtg tattttttat gagcaatttt cattttcatt ggtgaattac gaatcttggt    30419
tgcatcttgt tgtcgtatat ggcactgtac ccataccata tttacatgtt taaaaatttt    30479
aattttgtat tcgaattgta gtgtttgaaa ttgtgaattt aagtatggtt aaattatgtg    30539
agttagaaat aattgtgttc gaattttgt ggtgttaaac atactgtata tggattgtat    30599
tttaaaatac aagataaaca tgagtaggga ctaagaaata ggggctactg ctggagttgg    30659
aggcattttt tagtccttga gaaatggggg cagccctcat ttaacttta gacgcttcaa    30719 aataaggtct attgctggag atgctcttag gtccccatcg tttccttcaa tcagcattag    30779
ccgctaccaa aatttgaaat tttaaagttt ttcatcgaag tttattttcc agcattggta    30839
tttaagtcgc taaaaacaca tatatgaaag tcttatctgt aaattattat tattttgcta    30899
atacgccgaa tggcgtatta tatgtatttg gccaaaggat gggggcctta aaccttagcc    30959
ttagtcgtgc cctacaaaag acacacgcct cgtcagggca agggtactcg agcgtggagg    31019
catggttcgc aagccatggt cggcgaggcc atgctctagc aatgcggtgc agtccacctc    31079
ctctccgagc gcggagctcc aacgggtgat ggccaatgaa agaaggagac cgacttgccg    31139
ttggttgtag catgtaaatt tcttgcactt tcttaataaa tttcggctag tgttcgctag    31199
ctcgaccaaa aaaagagag gctaatgatg gggttaggaa gtgaaaacaa gcgcagtgga    31259
ggagaagaag atcgagaggc ctatttgtat gatgctttgt cgatgtagat ttagtcccat    31319
gctcatctca tccctcagcc acaacaatcc catcattgta gagctcatca gcttgctcta    31379
ccatctctcc ttgtttatgg gccactccca acctgctacc catcgcctga tctatgaatc    31439
tagctgtcaa tgacctcatt ggccctagtc ttgagatcac ccagtggatc ctttggcaaa    31499
gtggatccgc cttttgttttg ctttggagaa agaaaacgat gacttagcta aagatctcgt    31559
cggtcaaaaa gagagatgcc tttgatatat gctgaaaaat agaggagagg cagtgtcagc    31619
tggagagctc tttatccaca cccgtgggga tcgagcttat tggcgtagag ggagagacat    31679
tgagggagag agagtgcaag gggatttttt tgtaatttct agatttggtg gtgtttagtg    31739
caatactttg aacttatttg taaattaagt aaaacatgat tgtaatagaa aatatcataa    31799
```

-continued

```
actgacatag aaaaacaaag ataacaattg aagccactag cgctatggag aaaatgtgtg      31859
acctcggtct acatataacg gctatgtgtt attaccatgt cacttctaaa actaccatat      31919
aaccatatac gttttctcc tacttatcaa aaatataatt aacaaatttt tttaccggtt       31979
tagtttacaa gaaaaagtt tgactgcatt gttgataccc taccatcctt gtacgaaggc       32039
aggcgctaca caacaccgct gccgctgccg tcgccgccgt aagctaaggc tgtcacgccg      32099
gcgaccggcc acggccgacg tggaaagcga cctaatctgt aaagtgtaaa cccaccctat      32159
agaaaaaccc ggttggtggg acgagaatca ccgaatcagc gtcgacgacg acggccgacg      32219
actccagcag cggggtcac gagactcgga gccgagagag agaaagagga ccacgcgcgc       32279
attcactcaa ctgcataaaa aaccccgc gcggcggctg cgcagtcacg tctacgctcg        32339
cgggatcgct cgatgaaatc aaccaaaatc ttaaacaaac cgaaccaacc aaccaaccgt      32399
cgcgcgtgtg cgcgcgaggc gctcgattag cggagacgca aacccatgta acaccgtgcg     32459
gaaaaactta aagaaatccg cgtcgctcgc ccgtcgcgc gcgcgggggg cgcgtagtac       32519
ctccacacac gattctgcac ttgtactacc acgcgaacct gatgcggttt accggtcatc     32579
gattggctgc gaggcttgct gttactggtg gtggtagact ggtagtacgt tgcttgtact     32639
acctcactca tgtctggaga ttactacact tcgatctttt cctctgtttt gttaattgag    32699
atttggaggt gttactgttc gctgtgtggt aagtatatt ggtgtataac tacaagttgg      32759
tactctcaaa gggaaaaaaa ggtactgcaa attggctaat ctatgattct attctgcaca     32819
tgcatataga taagcactat aataaggaac tgaggatcgt gaaagtggc attaattata      32879 acaggaccat gtacgactat accactggca gggatttcac ggaatcaact ataggagtag     32939
gttagttggc acttggcaag gttgattgat tcactaacgt ggggaaaaga acacacgaga     32999
tcaaaggctg tcgtgggctt aaaataaaag ggcccatctg ggatcagctc ttttaagccc     33059
acatcactag ccaggaggct aggagtccag tattgcctcg tactgggccg tcctctgaaa     33119
tttggaggcc ctgtctaaaa ttctaatcaa gccttaaact taagtgacaa aataaaaaga     33179
ggtagactat ataacagcat accattacaa cggaatagct gtcgttagca cgatactcta     33239
tatgcatcag atatggtacc aggtactata ccgacgttag catgatccga taggtatagg     33299
atctggtgta cctagatatt atgctaacat aatcatgaca tcagctattc cattggaatg     33359
atataccggt ggtatcttcg gtaaattgtg agcatgctag gaatttaagt aaagggcctt     33419
agggttaaaa tcacacgttc ttagtcactg cactatcaag tgcatttcaa ccctaatgcc     33479
cttttatgat ctatatctgc cctcctagcc tattttggac gaggctccct cgtcctagaa     33539
gtaaatcatc gtatccataa tccaaccgat tagtagagaa aaaacatact tttcgaacgc     33599
aacagttctt gtcatcttgt gctctcaaat gttcattttc cccttactta aaggacatgg    33659
aaaacagaac agaccc                                                     33675
```

<210> SEQ ID NO 3
<211> LENGTH: 1119
<212> TYPE: DNA
<213> ORGANISM: Escherichia coli
<220> FEATURE:
<221> NAME/KEY: CDS
<222> LOCATION: (1)..(1119)

<400> SEQUENCE: 3

```
atg cat aac cag gct cca att caa cgt aga aaa tca aca cgt att tac        48
Met His Asn Gln Ala Pro Ile Gln Arg Arg Lys Ser Thr Arg Ile Tyr
1               5                   10                  15
```

-continued

| | |
|---|---|
| gtt ggg aat gtg ccg att ggc gat ggt gct ccc atc gcc gta cag tcc<br>Val Gly Asn Val Pro Ile Gly Asp Gly Ala Pro Ile Ala Val Gln Ser<br>20 25 30 | 96 |
| atg acc aat acg cgt acg aca gac gtc gaa gca acg gtc aat caa atc<br>Met Thr Asn Thr Arg Thr Thr Asp Val Glu Ala Thr Val Asn Gln Ile<br>35 40 45 | 144 |
| aag gcg ctg gaa cgc gtt ggc gct gat atc gtc cgt gta tcc gta ccg<br>Lys Ala Leu Glu Arg Val Gly Ala Asp Ile Val Arg Val Ser Val Pro<br>50 55 60 | 192 |
| acg atg gac gcg gca gaa gcg ttc aaa ctc atc aaa cag cag gtt aac<br>Thr Met Asp Ala Ala Glu Ala Phe Lys Leu Ile Lys Gln Gln Val Asn<br>65 70 75 80 | 240 |
| gtg ccg ctg gtg gct gac atc cac ttc gac tat cgc att gcg ctg aaa<br>Val Pro Leu Val Ala Asp Ile His Phe Asp Tyr Arg Ile Ala Leu Lys<br>85 90 95 | 288 |
| gta gcg gaa tac ggc gtc gat tgt ctg cgt att aac cct ggc aat atc<br>Val Ala Glu Tyr Gly Val Asp Cys Leu Arg Ile Asn Pro Gly Asn Ile<br>100 105 110 | 336 |
| ggt aat gaa gag cgt att cgc atg gtg gtt gac tgt gcg cgc gat aaa<br>Gly Asn Glu Glu Arg Ile Arg Met Val Val Asp Cys Ala Arg Asp Lys<br>115 120 125 | 384 |
| aac att ccg atc cgt att ggc gtt aac gcc gga tcg ctg gaa aaa gat<br>Asn Ile Pro Ile Arg Ile Gly Val Asn Ala Gly Ser Leu Glu Lys Asp<br>130 135 140 | 432 |
| ctg caa gaa aag tat ggc gaa ccg acg ccg cag gcg ttg ctg gaa tct<br>Leu Gln Glu Lys Tyr Gly Glu Pro Thr Pro Gln Ala Leu Leu Glu Ser<br>145 150 155 160 | 480 |
| gcc atg cgt cat gtt gat cat ctc gat cgc ctg aac ttc gat cag ttc<br>Ala Met Arg His Val Asp His Leu Asp Arg Leu Asn Phe Asp Gln Phe<br>165 170 175 | 528 |
| aaa gtc agc gtg aaa gcg tct gac gtc ttc ctc gct gtt gag tct tat<br>Lys Val Ser Val Lys Ala Ser Asp Val Phe Leu Ala Val Glu Ser Tyr<br>180 185 190 | 576 |
| cgt ttg ctg gca aaa cag atc gat cag ccg ttg cat ctg ggg atc acc<br>Arg Leu Leu Ala Lys Gln Ile Asp Gln Pro Leu His Leu Gly Ile Thr<br>195 200 205 | 624 |
| gaa gcc ggt ggt gcg cgc agc ggg gca gta aaa tcc gcc att ggt tta<br>Glu Ala Gly Gly Ala Arg Ser Gly Ala Val Lys Ser Ala Ile Gly Leu<br>210 215 220 | 672 |
| ggt ctg ctg ctg tct gaa ggc atc ggc gac acg ctg cgc gta tcg ctg<br>Gly Leu Leu Leu Ser Glu Gly Ile Gly Asp Thr Leu Arg Val Ser Leu<br>225 230 235 240 | 720 |
| gcg gcc gat ccg gtc gaa gag atc aaa gtc ggt ttc gat att ttg aaa<br>Ala Ala Asp Pro Val Glu Glu Ile Lys Val Gly Phe Asp Ile Leu Lys<br>245 250 255 | 768 |
| tcg ctg cgt atc cgt tcg cga ggg atc aac ttc atc gcc tgc ccg acc<br>Ser Leu Arg Ile Arg Ser Arg Gly Ile Asn Phe Ile Ala Cys Pro Thr<br>260 265 270 | 816 |
| tgt tcg cgt cag gaa ttt gat gtt atc ggt acg gtt aac gcg ctg gag<br>Cys Ser Arg Gln Glu Phe Asp Val Ile Gly Thr Val Asn Ala Leu Glu<br>275 280 285 | 864 |
| caa cgc ctg gaa gat atc atc act ccg atg gac gtt tcg att atc ggc<br>Gln Arg Leu Glu Asp Ile Ile Thr Pro Met Asp Val Ser Ile Ile Gly<br>290 295 300 | 912 |
| tgc gtg gtg aat ggc cca ggt gag gcg ctg gtt tct aca ctc ggc gtc<br>Cys Val Val Asn Gly Pro Gly Glu Ala Leu Val Ser Thr Leu Gly Val<br>305 310 315 320 | 960 |
| acc ggc ggc aac aag aaa agc ggc ctc tat gaa gat ggc gtg cgc aaa<br>Thr Gly Gly Asn Lys Lys Ser Gly Leu Tyr Glu Asp Gly Val Arg Lys<br>325 330 335 | 1008 |

-continued

```
gac cgt ctg gac aac aac gat atg atc gac cag ctg gaa gca cgc att    1056
Asp Arg Leu Asp Asn Asn Asp Met Ile Asp Gln Leu Glu Ala Arg Ile
        340                 345                 350 cgt gcg aaa gcc agt cag ctg gac gaa gcg cgt cga att gac gtt cag    1104
Arg Ala Lys Ala Ser Gln Leu Asp Glu Ala Arg Arg Ile Asp Val Gln
    355                 360                 365 cag gtt gaa aaa taa                                                 1119
Gln Val Glu Lys
    370
```

<210> SEQ ID NO 4
<211> LENGTH: 686
<212> TYPE: PRT
<213> ORGANISM: Oryza sativa

<400> SEQUENCE: 4

```
Met Ala Thr Gly Val Ala Pro Ala Pro Leu Pro His Val Arg Val Arg
  1               5                  10                  15

Asp Gly Gly Ile Gly Phe Thr Arg Ser Val Asp Phe Ala Lys Ile Leu
                 20                  25                  30

Ser Val Pro Ala Thr Leu Arg Val Gly Ser Ser Arg Gly Arg Val Leu
             35                  40                  45

Val Ala Lys Ser Ser Ser Thr Gly Ser Asp Thr Met Glu Leu Glu Pro
         50                  55                  60

Ser Ser Glu Gly Ser Pro Leu Leu Gly Ile Thr Arg Leu Leu Phe
 65                  70                  75                  80

Thr Leu His Met Val Gly Asn Val Pro Leu Gly Ser Asp His Pro Ile
                 85                  90                  95

Arg Ile Gln Thr Met Thr Thr Ser Asp Thr Lys Asp Val Ala Lys Thr
                100                 105                 110

Val Glu Glu Val Met Arg Ile Ala Asp Lys Gly Ala Asp Phe Val Arg
            115                 120                 125

Ile Thr Val Gln Gly Arg Lys Glu Ala Asp Ala Cys Phe Glu Ile Lys
        130                 135                 140

Asn Thr Leu Val Gln Lys Asn Tyr Asn Ile Pro Leu Val Ala Asp Ile
145                 150                 155                 160

His Phe Ala Pro Thr Val Ala Leu Arg Val Ala Glu Cys Phe Asp Lys
                165                 170                 175

Ile Arg Val Asn Pro Gly Asn Phe Ala Asp Arg Arg Ala Gln Phe Glu
            180                 185                 190

Gln Leu Glu Tyr Thr Glu Asp Tyr Gln Lys Glu Leu Glu His Ile
        195                 200                 205

Glu Lys Val Pro Asn Ile Ser Leu Phe Ser Val Asn Leu Val Phe Ser
    210                 215                 220

Pro Leu Val Glu Lys Cys Lys Gln Tyr Gly Arg Ala Met Arg Ile Gly
225                 230                 235                 240

Thr Asn His Gly Ser Leu Ser Asp Arg Ile Met Ser Tyr Tyr Gly Asp
                245                 250                 255

Ser Pro Arg Gly Met Val Glu Ser Leu Glu Phe Ala Arg Ile Cys
            260                 265                 270

Arg Lys Leu Asp Phe His Asn Phe Val Phe Ser Met Lys Ala Ser Asn
        275                 280                 285

Pro Val Ile Met Val Gln Ala Tyr Arg Leu Leu Val Ala Glu Met Tyr
    290                 295                 300

Asn Leu Gly Trp Asp Tyr Pro Leu His Leu Gly Val Thr Glu Ala Gly
```

```
                305                 310                 315                 320
Glu Gly Glu Asp Gly Arg Met Lys Ser Ala Ile Gly Ile Gly Thr Leu
                325                 330                 335
Leu Met Asp Gly Leu Gly Asp Thr Ile Arg Val Ser Leu Thr Glu Pro
                340                 345                 350
Pro Glu Glu Ile Asp Pro Cys Arg Arg Leu Ala Asn Leu Gly Thr
                355                 360                 365
His Ala Ala Asp Leu Gln Ile Gly Val Ala Pro Phe Glu Glu Lys His
                370                 375                 380
Arg Arg Tyr Phe Asp Phe Gln Arg Arg Ser Gly Gln Leu Pro Leu Gln
385                 390                 395                 400
Lys Glu Ala Pro Glu Leu Leu Tyr Arg Ser Leu Ala Ala Lys Leu Val
                405                 410                 415
Val Gly Met Pro Phe Lys Asp Leu Ala Thr Val Asp Ser Ile Leu Leu
                420                 425                 430
Lys Glu Leu Pro Pro Val Glu Asp Ala Gln Ala Arg Leu Ala Leu Lys
                435                 440                 445
Arg Leu Val Asp Ile Ser Met Gly Val Leu Thr Pro Leu Ser Glu Gln
450                 455                 460
Leu Thr Lys Pro Leu Pro His Ala Ile Ala Leu Val Asn Val Asp Glu
465                 470                 475                 480
Leu Ser Ser Gly Ala His Lys Leu Leu Pro Glu Gly Thr Arg Leu Ala
                485                 490                 495
Val Thr Leu Arg Gly Asp Glu Ser Tyr Glu Gln Leu Asp Leu Leu Lys
                500                 505                 510
Gly Val Asp Asp Ile Thr Met Leu Leu His Ser Val Pro Tyr Gly Glu
                515                 520                 525
Glu Lys Thr Gly Arg Val His Ala Ala Arg Arg Leu Phe Glu Tyr Leu
                530                 535                 540
Glu Thr Asn Gly Leu Asn Phe Pro Val Ile His Ile Glu Phe Pro
545                 550                 555                 560
Lys Ser Val Asn Arg Asp Asp Leu Val Ile Gly Ala Gly Ala Asn Val
                565                 570                 575
Gly Ala Leu Leu Val Asp Gly Leu Gly Asp Gly Val Leu Leu Glu Ala
                580                 585                 590
Ala Asp Gln Glu Phe Glu Phe Leu Arg Asp Thr Ser Phe Asn Leu Leu
                595                 600                 605
Gln Gly Cys Arg Met Arg Asn Thr Lys Thr Ile Ala Ile Met Gly Cys
                610                 615                 620
Ile Val Asn Gly Pro Gly Glu Met Ala Asp Ala Asp Phe Gly Tyr Val
625                 630                 635                 640
Gly Gly Ala Pro Gly Lys Ile Asp Leu Tyr Val Gly Lys Thr Val Val
                645                 650                 655
Gln Arg Gly Ile Ala Met Glu Gly Ala Thr Asp Ala Leu Ile Gln Leu
                660                 665                 670
Ile Lys Asp His Gly Arg Trp Val Asp Pro Pro Val Glu Glu
                675                 680                 685

<210> SEQ ID NO 5
<211> LENGTH: 594
<212> TYPE: DNA
<213> ORGANISM: Arabidopsis thaliana
<220> FEATURE:
<221> NAME/KEY: unsure
<222> LOCATION: (1..594)
```

<223> OTHER INFORMATION: unsure at all n locations

<400> SEQUENCE: 5

```
aaaatcgtca atccctctca aactcttctc accactaatt tcttcctctg gaacattctc    60
ttctctatta ttttgattcc cttggcctca acactggttt ctcaattgca tgatcttggc   120
tcgtcttcag ttactttgat tcactgagaa aaatggcgac tggagtattg ccagctccgg   180
tttctgggat caagataccg gattcgaaag tcgggtttgg taaaagcatg aatcttgtga   240
gaatttgtna tgttaggagt ctaagatctg ctaggagaag agtttcggtt atccggaatt   300
caaaccaagg ctctgattta gctgagcttc aaccctgcat ccgaaggaaa gcccctcttc   360
ttagtgccaa ggcaggaaat attgtgaatc attgcataan gcggttagga ggaagnctcg   420
gacctgtaat ggttgaaatg tcgncccttn gaagngnaca ccggtanggg tcaaacggtg   480
ccttcttngg gtacaaaang tnttccttgg anccntttng tggggtttt gggattgcgg    540
aaaagggc tgnttttnaa gggnacctnn caaggnagna agggnggtc tttt            594
```

<210> SEQ ID NO 6
<211> LENGTH: 615
<212> TYPE: DNA
<213> ORGANISM: Glycine max
<220> FEATURE:
<221> NAME/KEY: unsure
<222> LOCATION: (1..615)
<223> OTHER INFORMATION: unsure at all n locations

<400> SEQUENCE: 6

```
accagaagtg atgagcctta tgaagaactg acattctta agggtgttga tgctactatg    60
cttttccatg accttcctta tacagaagac agaattagca gagtgcatgc aaccagacgg   120
ttatttgagt acctatctga caattctcta aacttccctg ttattcacca tattcagttc   180
ccaaatggga ttcacaggga tgacttggta attggtgctg ttctgatgc tggagcccctt   240
ctggttgatg ggcttggaga tggactactt ttggaagccc cggacaagga ttttgaattt   300
attagaaaca cttcttttcaa tttgttgcaa ggctgcagaa tgagaaatac aaagacagag   360
tatgtctcat gtccatcctg tggcagaaca ttgtttgatc ttcaagaagt aagtgcacaa   420
attcgggaga agacatcaca cctncctggt gtttcgattg caatcatggg atgcattgtt   480
aatggaccag gggagatggc tgatgcagac tttgggtatg tgggaagcac tccccggaag   540
attgacctct atgttgggaa gactggtgtg aagcgtggga attcaatgga gcatgccaac   600
catggcttga tccga                                                    615
```

<210> SEQ ID NO 7
<211> LENGTH: 589
<212> TYPE: DNA
<213> ORGANISM: Lycopersicon esculentum

<400> SEQUENCE: 7

```
tggcgatgaa tcacatgatg agttggaaat cctgaagagc tctgatgtta caatgattct    60
tcataatctg ccatatacag aggaaaaaat tggcagggtt caagcagcca ggaggctttt   120
tgagtatctt tccgagaatt ccttgaactt ccagtgatt catcacatac aatttcccag   180
caacacccac agagatgact tagtgattgg tgccgggaca aatgcgggag ccctcttggt   240
agatgggctt ggtgatggac ttctcttgga agctccagac aaggattttg attttctcag   300
aaatacatct ttcaatttgc ttcaaggttg cagaatgcgg aacacaaaaa cggaatatgt   360
atcatgccca tcctgtggca gaactttatt cgatcttcaa gagataagcg ctcaaattag   420
```

```
agagaagacg tcacacttgc ctggtgtttc aattgccatc atgggttgca ttgtgaatgg    480
acctggggag atggctgatg ctgactttgg atatgttggt ggtgctcctg gaaagattga    540
cctttacgtc ggcaagacag tggtgaaacg ccctattgaa atggagcat               589

<210> SEQ ID NO 8
<211> LENGTH: 617
<212> TYPE: DNA
<213> ORGANISM: Mesembryanthemum crystallinum

<400> SEQUENCE: 8
gaaaagcata gacattattt tgactttcaa cgtagaactg gtcaattacc gattcagaaa     60
gagggtgaag atgtggacta tagaggtgtc ctacaccgtg atggttctgt cctcatgact   120
gtttccttgg acatgttgaa gacacctgaa ctcctttaca agtcattagc agcaaagctt   180
gttgttggca tgccatttaa ggatctggct actgtagact ctattttttct gagagagctt   240 tcaccagtag atgactctga tgctcggcta gctctgaaga ggttaataga tataagtatg   300
ggtgtcatag ctccttttttc tgagcaactg acaaagccct tgccaaatgc aattgtattg   360
gtgaacctta aagagttgtc aaccggtgca tacaagcttt taccagtagg aacccgcttg   420
gcagtatctg tgcgaggtga tgaaccatat tgagacattg gagatcctta aagatattga   480
tgcttcaatg gctttttatg aactgtcttt taccgagagg atattcacac agtgcatgct   540
ggaccaaagc ttttgaggtc ctatcagata agcttggacc tcccgtaatt aacatatcct   600
atcccttcgg attaagg                                                  617

<210> SEQ ID NO 9
<211> LENGTH: 416
<212> TYPE: DNA
<213> ORGANISM: Oryza sativa
<220> FEATURE:
<221> NAME/KEY: unsure
<222> LOCATION: (1..416)
<223> OTHER INFORMATION: unsure at all n locations

<400> SEQUENCE: 9
ggattcggca cgagtctaat tgatggtctt ggtgatggtg tacttcttga aagctgctga     60
ccaagaaatt tgagtttttg agggacacat cctccaactt gttacagggc tgcaggatgc   120
gcaacacaaa aacggaatat ttccctggtc ctcctggtgg gcggacacnc tttnaccncc   180
aaaaattcan tgctcaaatt aaanaaaaaa ccnctcatct gccaggcntc tctattgcta   240
tcatgggtng cattgtcaat gggccagggg aaatggccaa tcctaattnc ggatacttng   300
gaggtgccct ggagaaaatc nacctntatn ttggttnttt tttttnnaac ggggcatngc   360
aanagaaggg ggcccnnacc ccnanatncn ttcnccgggn ccngggccgn ggggtt       416

<210> SEQ ID NO 10
<211> LENGTH: 621
<212> TYPE: DNA
<213> ORGANISM: Zea mays

<400> SEQUENCE: 10
gaattcggca ccagaagcca ctcccacatg caattgtact tgtcaacctc gacgaattgt     60
caagtggtgc acacaaactt tgccagaaag gcactagact agctgtcact cttcgtggtg   120
atgaatcata cgagcagcta gatattctta aggatgttga tgatataaca atgttgttac   180
ataatgttcc atatggtgag gagaagacag gcagggtgca tgctgctagg aggttatttg   240
```

-continued

| | |
|---|---|
| agtacttaca ggccaatggc ttgaacttcc ctgtaattca tcacataaat ttccctgaaa | 300 |
| ccattgacag agatggtctt gtcattggtg ctggggccaa cgttggtgct ctcttagtcg | 360 |
| atggtcttgg tgatggtgta ttccttgaag ctgctgacca ggaatttgag tttctgaggg | 420 |
| acacatcttt caacttgctc caaggttgca ggatgcgcaa cacaaaaact gaatatgtgt | 480 |
| cttgtccttc ctgcggccga acactctttg accttcagga aatcagcgct gagattagag | 540 |
| aaaagacctc tcatctgcca gtgtctcga tcgctatcat gggctgtatt gcaatggacc | 600 |
| aggagagatg gctgatgccg a | 621 |

<210> SEQ ID NO 11
<211> LENGTH: 601
<212> TYPE: DNA
<213> ORGANISM: Pinus taeda
<220> FEATURE:
<221> NAME/KEY: unsure
<222> LOCATION: (1..601)
<223> OTHER INFORMATION: unsure at all n locations

<400> SEQUENCE: 11

| | |
|---|---|
| aatgcaagaa gtacggaagg gcaatgcgaa ttggcacaaa ccatggaagt ctttccgatc | 60 |
| gtactatgag ttattatggt gattctccca ggggtatggt ggaatcagca tttgaatttg | 120 |
| cacgcatttg ccggaagttg ggttttcata attttgtgtt tcaatgaaa gcagcgatc | 180 |
| ctgtagtcat ggttcaggca taccgtttac ttgttgcgga gatgtatgtg caaggatggg | 240 |
| attatccatt gcatttagga gttactgaag ctggtgaagg tgaagatgga cgcatgaagt | 300 |
| ctgcaattgg cattggaaca cttttgcagg atggtttggg tgatactatt cgagtttccc | 360 |
| ttacagaacc tccagaagag gagatcaatc cctgtagaag acttgcaaat cttgggatgc | 420 |
| aagctgcaaa gctanggaaa ggagtggctc cttttgagga gaacatcgtc attactttac | 480 |
| tttccaacgc angactggcn agctccagta cagaaggagg gtgatgaggt ggatacagag | 540 |
| gagtccgcat cgtgatggtc tgttctaatg tcagtgtcct tgacagntga agacacanaa | 600 |
| a | 601 |

<210> SEQ ID NO 12
<211> LENGTH: 443
<212> TYPE: DNA
<213> ORGANISM: Physcomitrella patens

<400> SEQUENCE: 12

| | |
|---|---|
| gcacgtatct gccgcaaaca tgactatatt aatttcttgt tttctatgaa agcaagcaat | 60 |
| ccggtcgtaa tggttcaagc atatcggctt ttagtatctg agatgtatgt gaacaactgg | 120 |
| gactacccat tacatcttgg tgttactgag gctggagagg gagaggatgg tcgcatgaag | 180 |
| tcagctatcg gcattggtgc tttacttcag gatggtctcg gtgacaccat acgtgtttca | 240 |
| ttgacggaag ctcctgaaga agaaattgat ccttgcacaa agcttgcaaa ccttggcatg | 300 |
| aagatttctg cagaacagaa gggggtggct gaattcgaag agaagcaccg gcgatacttt | 360 |
| gacttccaac gaaggaccgg ccaacttcca ctgcagaggg agggagagtt ggtggactac | 420 |
| agaaacgttc tgcaccgtga tgg | 443 |

<210> SEQ ID NO 13
<211> LENGTH: 938
<212> TYPE: DNA
<213> ORGANISM: Arabidopsis thaliana
<220> FEATURE:
<221> NAME/KEY: unsure
<222> LOCATION: (1..938)
<223> OTHER INFORMATION: unsure at all n locations

<400> SEQUENCE: 13

| | | | | | |
|---|---|---|---|---|---|
| atgatactgc | cagctannnn | nnnnnnnnnn | nnnnnnnnnn | nnnnnnnnnn | 60 |
| nnnnnnnnnn | nnnnnnnnnn | nnnccacgcg | tccgaaaacg | ttttatcctg | agtttctttc | 120 |
| accatccagc | ttcatttgtg | aaaaatcgtc | aatccctctc | aaactcttct | caccactaat | 180 |
| ttcttcctct | ggaacattct | cttctctatt | attttgattc | ccttggcctc | aacactggtt | 240 |
| tctcaattgc | atgatcttgg | ctcgtcttca | gttactttga | ttcactgaga | aaaatggcga | 300 |
| ctggagtatt | gccagctccg | gtttctggga | tcaagatacc | ggattcgaaa | gtcgggtttg | 360 |
| gtaaaagcat | gaatcttgtg | agaatttgtg | atgttaggag | tctaagatct | gctaggagaa | 420 |
| gagtttcggt | tatccggaat | tcaaaccaag | gctctgattt | agctgagctt | caacctgcat | 480 |
| ccgaaggaag | ccctctctta | gtgccaagac | agaaatattg | tgaatcattg | cataagacgg | 540 |
| tgagaaggaa | gactcgtact | gttatggttg | gaaatgtcgc | ccttggaagc | gaacatccga | 600 |
| taaggattca | aacgatgact | acttcggata | caaaagatat | tactgaaact | gttgatgagg | 660 |
| ttatgagaat | agcggataaa | ggagctgata | ttgtaaggat | aactgtccaa | gggaagaaag | 720 |
| aggcggatgc | gtgctttgaa | ataaaagata | aactcgttca | gcttaattac | aatataccgc | 780 |
| tggttgcaga | tattcattgt | gcccctactg | tagccttacg | agtcgctgaa | tgctttgaca | 840 |
| agatccgtgt | caacccagga | aatttttgcgg | acaggcgggc | ccagtttgag | acgattgatt | 900 |
| atacagaaga | tgaatatcag | aaagaactcc | agcatatc | | 938 |

<210> SEQ ID NO 14
<211> LENGTH: 432
<212> TYPE: DNA
<213> ORGANISM: Arabidopsis thaliana

<400> SEQUENCE: 14

| | | | | | |
|---|---|---|---|---|---|
| agcataacaa | ggctctgatt | tagctgagct | tcaacctgca | tccgaaggaa | gccctctctt | 60 |
| agtgccaaga | cagaaatatt | gtgaatcatt | gcataagacg | gtgagaagga | agactcgtac | 120 |
| tgttatggtt | ggaaatgtcg | cccttggaag | cgaacatccg | ataaggattc | aaacgatgac | 180 |
| tacttcggat | acaaaagata | ttactggaac | tgttgatgag | gttatgagaa | tagcggataa | 240 |
| aggagctgat | attgtaagga | taactgttca | agggaagaaa | gaggcggatg | cgtgctttga | 300 |
| aataaaagat | aaactcgttc | agcttaatta | caatataccg | ctggttgcag | atattcattt | 360 |
| tgcccctact | gtagccttac | gagtcgctga | atgctttgac | aagatccgtg | tcaacccaag | 420 |
| aaattttgcg | ga | | | | | 432 |

<210> SEQ ID NO 15
<211> LENGTH: 528
<212> TYPE: DNA
<213> ORGANISM: Arabidopsis thaliana
<220> FEATURE:
<221> NAME/KEY: unsure
<222> LOCATION: (1..528)
<223> OTHER INFORMATION: unsure at all n locations

<400> SEQUENCE: 15

| | | | | | |
|---|---|---|---|---|---|
| tgatacgcca | gctctatacg | actcactatt | agggaagctg | gtacgcctgc | aggtacccgg | 60 |
| tccgggaatt | cccngggtcg | acccacgcgt | ccgaaagaac | tccagcatat | cgagcaggtc | 120 |
| ttcactcctt | tggttgagaa | atgcaaaaag | tacgggagag | caatgcgtat | tgggacaaat | 180 |

```
catggaagtc tttctgaccg tatcatgagc tattacgggg attctccccg aggaatggtt    240
gaatctgcgt ttgagtttgc aagaatatgt cggaaattag actatcacaa ctttgttttc    300
tcaatgaaag cgagcaaccc agtgatcatg gtccaggcgt accgtttact tgtggctgag    360
atgtatgttc atggatggga ttatccttg catttgggag ttactgaggc aggagaaggc    420
gaagatggac ggatgaaatc tgcgattgga attgggacgc ttcttcagga cgggctcggt    480
gacacaataa gagtttcact gacggagcca ccagaagagg agatagat                 528

<210> SEQ ID NO 16
<211> LENGTH: 379
<212> TYPE: DNA
<213> ORGANISM: Arabidopsis thaliana

<400> SEQUENCE: 16
gcgtattggg acaaatcatg gaagtctttc tgaccgtatc atgagctatt acgggattc      60 tccccgagga atggttgaat ctgcgtttga gtttgcaaga atatgtcgga aattagacta    120
tcacaacttt gttttctcaa tgaaagcgag caacccagtg atcatggtcc aggcgtaccg    180
tttacttgtg gctgagatgt atgttcatgg atgggattat cctttgcatt tgggagttac    240
tgaggcagga gaaggcgaag atggacggat gaaatctgcg attggaattg gacgcttct    300 tcaggacggg ctcggtgaca caataagagt ttcactgacg gagccaccag aagaggagat    360
agatccctgc aagcgattg                                                  379

<210> SEQ ID NO 17
<211> LENGTH: 395
<212> TYPE: DNA
<213> ORGANISM: Arabidopsis thaliana

<400> SEQUENCE: 17
aaagaactcc agcatatcga gcaggtcttc actcctttgg ttgagaaatg caaaaagtac     60
gggagagcaa tgcgtattgg gacaaatcat ggaagtcttt ctgaccgtat catgagctat    120 tacgggatt ctccccgagg aatggttgaa tctgcgtttg agtttgcaag aatatgtcgg    180
aaattagact atcacaactt tgttttctca atgaaagcga gcaacccagt gatcatggtc    240
caggcgtacc gtttacttgt ggctgagatg tatgttcatg gatgggatta cctttgcat    300 ttgggagtta ctgaggcagg agaaggcgaa gatggacgga tgaaatctgc gattggaatt    360
ggggacactt cttcaggacg ggctcggtga cacaa                                395

<210> SEQ ID NO 18
<211> LENGTH: 395
<212> TYPE: DNA
<213> ORGANISM: Arabidopsis thaliana

<400> SEQUENCE: 18
aaagaactcc agcatatcga gcaggtcttc actcctttgg ttgagaaatg caaaaagtac     60
gggagagcaa tgcgtattgg gacaaatcat ggaagtcttt ctgaccgtat catgagctat    120 tacgggatt ctccccgagg aatggttgaa tctgcgtttg agtttgcaag aatatgtcgg    180
gaattagact atcacaactt tgttttctca atgaaagcga gcaacccagt gatcatggtc    240
caggcgtacc gtttacttgt ggctgagatg tatgttcatg gatgggatta cctttgcat    300 ttgggagtta ctgatgcagg agaaggcgaa gatggacgga tgaaatctgc gattggaatt    360
gggacgcttc ttcaggacgg gctcggtgac acaat                                395
```

```
<210> SEQ ID NO 19
<211> LENGTH: 412
<212> TYPE: DNA
<213> ORGANISM: Arabidopsis thaliana

<400> SEQUENCE: 19
atgctggagg ccttcttgtg gatggactag gtgatggcgt aatgctcgaa gcacctgacc      60
aagattttga ttttcttagg aatacttcct tcaacttatt acaaggatgc agaatgcgta     120
acactaagac ggaatatgta tcgtgcccgt cttgtggaag aacgcttttc gacttgcaag     180
aaatcagcgc cgagatccga gaaaagactt cccatttacc tggcgtttcg atcgcaatca     240
tgggatgcat tgtgaatgga ccaggagaaa tggcagatgc tgatttcgga tatgtaggtg     300
gttctcccgg aaaaatcgac ctttatgtcg gaaagacggt ggtgaagcgt gggatagcta     360
tgacggaggc aacagatgct ctgatcggtc tgatcaaaga acatggtcgt tg            412

<210> SEQ ID NO 20
<211> LENGTH: 1172
<212> TYPE: DNA
<213> ORGANISM: Arabidopsis thaliana
<220> FEATURE:
<221> NAME/KEY: unsure
<222> LOCATION: (1..1172)
<223> OTHER INFORMATION: unsure at all n locations

<400> SEQUENCE: 20
gggtatgcca ttcaaggatc tggcaactgt tgattcaatc ttattaaaga gagctaccgc      60
ctgtagatga tcaagtggct cgtttggctc taaaacggtt gattgatgtc agtatgggag     120
ttatagcacc tttatcagag caactaacaa agccattgcc caatgccatg gttcttgtca     180
acctcaagga actatctggt ggcgcttaca agcttctccc tgaaggtaca cgcttggttg     240
tctctctacg aggcgatgag ccttacgagg agcttgaaat actcaacaac attgatgcta     300
cgatgattct ccatgatgta cctttcactg aagacaaagt tagcagagta catgcagctc     360
ggaggctatt cgagttctta tccgagaatt cagttaactt tcctgttatt catcacataa     420
acttcccaac cggaatccac agagacgaat tggtgattca tgcagggaca tatgctggag     480
gccttcttgt ggatggacta cgtgatggcg taatgctcga agcacctgac caagattttg     540
attttcttag gaatacttcc ttcaacttat acaaggatg cagaatgcgt aacactaaga     600
cggaatatgt atcgtgcccg tcttgtggaa gaacgctttt cgacttgcaa gaaatcagcg     660
ccgagatccg agaaaagact cccatttac ctggcgtttc gatcgcaatc atgggatgca     720
ttgtgaatgg accaggagaa atggcagatg ctgatttcgg atatgtaggt ggttctcccg     780
gaaaaatcga cctttatgtc ggaaagacgg tggtgaagcg tgggatagct atgacggagg     840
caacagatgc tctgatcggt ctgatcaaag aacatggtcg ttgggtcgac ccgcccgtgg     900
ccgatgagta gatttcaaaa cggagaaaga tgggtgggcc attctttgaa aactgtgaga     960
ggagatatat atatttgtgt gtgtatatca tctgtttgtt gtgtattgca tcattcattt    1020
tggacaaatg tccaaattct cttaagttga taaaagttct taggccaaat taaatttaat    1080
ataaaaaaaa aaaaaaaaag gcnnnnnnnn nnnnnnnnnn nnnnnnnnnn nnnnnnnnnn    1140
nnnnnnnnnn nnnnnnnnnn nnnnnnnnnn nn                                  1172

<210> SEQ ID NO 21
<211> LENGTH: 584
<212> TYPE: DNA
<213> ORGANISM: Zea mays
```

-continued

```
<400> SEQUENCE: 21
caggttaatt aattcctgta cgccgtcggt ttcgggtact cgtttaattt cttcccgacc      60
acggttgatg gcaatgtaac cggcttgttt acccacatag ccatagtcgg catcggccat     120
ttccccgggg ccattgacaa tacagcccat gacggcgatg tctaaacccg ttagatgttt     180
agtggcttct cggacttcat gtaacacgtc ttccaagttg aacaacgtgc ggccacagga     240
aggacaggcc acatattcca ccatggtttt ccgcaaaccc agcgcctgga gaatgctgta     300
gcaaacggga atttcttttt cggggcttc ggtgagggat acccggatag tatcgccaat      360
gccatcagct aaaagggtgg caatgccagc ggtggattta atgcggccat attccccatc     420
cccggcttcg gtaaccccta gatggagggg ataatccatg cccaactcgt tcatacgttt     480
caccatgagg cgataggcgg ccaacattac cggtacccgg gacgctttca tggaaacgac     540
taggttgcgg aaatctaaag actcacaaat tttgatgaat tcca                      584

<210> SEQ ID NO 22
<211> LENGTH: 670
<212> TYPE: DNA
<213> ORGANISM: Zea mays

<400> SEQUENCE: 22
caggtcgact ctagaggatc ggcgttaacc atggttctct ctccgaaaga atgcttttac      60
ctacttttta cccccgaggg catggtgcaa tcggccctgg aattcatcaa aatttgtgag     120
tccttagatt tccgcaacct agtcgttccc atgaaagcgt cccgggtacc ggtaatgttg     180
gccgcctatc gcctcatggt gaaacgtatg gacgagttgg gcatggatta tcccctccat     240
ctaggggtta ccgaagccgg ggatggggaa tatggccgca ttaaatccac cgctggcatt     300 gccaccctttt agctgatgg cattggcgat actatccggg tatccctcac cgaagccccc     360
gaaaaagaaa ttcccgtttg ctacagcatt ctccaggcgc tgggtttgcg gaaaaccatg     420
gtggaatatg tggcctgtcc ttcctgtggc cgcacgttgt tcaacttgga agacgtgtta     480
catgaagtcc gagatgccac taaacatcta acgggtttag actttcgccg tcatgggctg     540
tattgtcaat ggccccgggg caatggccga tgccgactat ggctatgtgg gtaaacaagc     600
cggttacatt gccatcaacc gtggtcggga agaaattaaa cgagtacccg aaaccgacgg     660
cgtacaggaa                                                           670

<210> SEQ ID NO 23
<211> LENGTH: 596
<212> TYPE: DNA
<213> ORGANISM: Zea mays
<220> FEATURE:
<221> NAME/KEY: unsure
<222> LOCATION: (1..596)
<223> OTHER INFORMATION: unsure at all n locations

<400> SEQUENCE: 23
caggtcgact ctagaggatc ggcgttaacc atggttctct ctccgaaaga atgcttttac      60
ctacttttta cccccgaggg catggtgcaa tcggccctgg aattcatcaa aatttgtgag     120
tccttagatt tccgcaacct agtcgttccc atgaaagcgt cccgggtacc ggtaatgttg     180
gccgcctatc gcctcatggt gaaacgtatg gacgagttgg gcatggatta tcccctccat     240
ctaggggtta ccgaagccgg ggatggggaa tatggccgca ttaaatccac cgctggcatt     300 gccaccctttt agctgatgg cattggcgat actatccggg tatccctcac cgaagccccc     360
gaaaaagaaa ttcccgtttg ctacagcatt ctccaggcgc tgggtttgcg gaaaaccatg     420
```

```
gtggaatatg tggcctgtcc ttcctgtggc cgcacgttgt tcaacttgga agacgtgtta      480
catgaagtcc gagatgccac taaacatcta acgtgtttag actttcgncg tcatgtgctg      540
tattgtcaat ggccccggtg caatggccga tgccgactat ggctatgtgg gtaaac         596
```

<210> SEQ ID NO 24
<211> LENGTH: 403
<212> TYPE: DNA
<213> ORGANISM: Zea mays

<400> SEQUENCE: 24

```
cagacaagga ggaggaaaac tcgaactgtg atggtgggga atgtgccact tgggagtgat      60
caccccataa ggattcaaac catgacgact tcagatacca aggatgttgc gaaaacagta     120
gaggaggtga tgaggatagc agataaagga gctgatcttg ttagaataac agtccagggt     180
aggaaggaag ctgatgcctg ctttgagatc aagaacactc tggttcagaa gaattacaac     240
attccactag tggccgatat tcattttgct cctacggtag ctctaaaggt ggcagaatgt     300
tttgacaaaa ttcgtgtgaa cccaggaaat tttgctgatc gtcgtgctca atttgaaaag     360
ctggaatata ctgacgacga ctaccaaaaa gagctagagc ata                      403
```

<210> SEQ ID NO 25
<211> LENGTH: 293
<212> TYPE: DNA
<213> ORGANISM: Zea mays

<400> SEQUENCE: 25

```
cagacaaggc ggaggaaaac tcgaactgtg atggtgggga atgtgccact tggcagtgat      60
caccccataa ggattcaaac catgacgact tcagatacca aggatgttgc gaaaacagta     120
gaggaggtga tgaggatagc agataaagga gctgatcttg ttagaataac agtccagggt     180
aggaaggaag ctgatgcctg ctttgagatc aagaacactc tggttcagaa gaattacaac     240
attccactag tggccgatat tcattttgct cctacggtag ctctaagggt ggc            293
```

<210> SEQ ID NO 26
<211> LENGTH: 456
<212> TYPE: DNA
<213> ORGANISM: Zea mays

<400> SEQUENCE: 26

```
cagacaaggc ggaggaaaac tcgaactgtg atggtgggga atgtgccact tggcagtgat      60
caccccataa ggattcaaac catgacgact tcagatacca aggatgttgc gaaaacagta     120
gaggaggtga tgaggattgc agataaagga gctgatcttg ttagaataac agtccagggt     180
aggaaggaag ctgatgcctg ctttgagatc aagaacaact ctggttcaga agaattacaa     240
ccttccacta gtggacctga tattcatttt gctccttcag tagctttaaa ggtggcagaa     300
tgtttggaca aattaattga aacacacaat ttcttgttga tagtgtacct taattagaaa     360
agctggaatt taccggctac gacttccata aagcgcttgg gcttgtttaa caattggttt     420
ttaccttaat cgaatatttc acagaaattt gaattt                              456
```

<210> SEQ ID NO 27
<211> LENGTH: 619
<212> TYPE: DNA
<213> ORGANISM: Zea mays

<400> SEQUENCE: 27

```
caccgaaggt ttctaattta tttctcagat ctcaataaat gtacaaaatg tgtagggatg      60
atgtacattg tatgctcagt tcctgcattg cgtgtttcgc tttacagaat atataaacta    120
cagacttggc tacagcctac agccctactc ctcggcagga ggatccaccc atcggccatg    180
gtccttgatc agctggatca aggcgtcagt tgcaccttcc atggcgatgg cgcgctgcac    240
aacggtcttg ccaacataaa ggtcgatctt ccgggagcg cctccaacgt atccgaaatc    300
ggcatcagcc atctctcctg gtccattgac aatacaaccc atgatagcga tcgaaacacc    360
tggcagatga gaggtctttt ctctaatctc agcgctgatt tcctgaaggt caaagagtgt    420
tcggccgcag aaggacaag acacatattc agtttttgtg ttgcgcatcc tgcaaccttg    480
gagcaagttg aaagatgtgt ccctcaggaa ctcaaattcc tggtcagcag cttcaaggaa    540
tacaccatca ccaagaccat cgactaagag agcaccaacg ttggccccag caccaatgac    600
aagaccatct ctgtcaatg                                                  619

<210> SEQ ID NO 28
<211> LENGTH: 422
<212> TYPE: DNA
<213> ORGANISM: Zea mays

<400> SEQUENCE: 28
tcgcttgcac ttgggtgtta cagaagctgg agagggtgaa gatggaagga tgaaatctgc     60
tattggcatt gggacactgc taatggatgg tttgggtgat acaatccgtg tctccctcac    120
agaaccacca gaagaagaga ttgatccttg ccaaaggttg gcaaatcttg ggacgcaggc    180
cgcaaacctt caaattgggg tggccccatt tgaagaaaag cacaggcgct attttgattt    240
ccagcgtagg agtggtcaat tgcctttgca gaaggaggga ggcgatagtt gactacagaa    300
atgtcctgca tcgtgatggt atctgactga tggcagtttc cctggatcag ttgaaggctc    360
ctgatctcct ttataggtat attgcagcaa agcttgcgga tggcatgcct ttcaaggatc    420
tg                                                                    422

<210> SEQ ID NO 29
<211> LENGTH: 430
<212> TYPE: DNA
<213> ORGANISM: Zea mays

<400> SEQUENCE: 29
tcgcttgcac ttgggtgtta cagaagctgg agagggtgaa gatggaagga tgaaatctgc     60
tattggcatt gggacactgc taatggatgg tttgggtgat acaatccgtg tctccctcac    120
agaaccacca gaagaagaga ttgatccttg ccaaaggttg gcaaatcttg ggacgcaggc    180
tgcaaacctt caaattgggg tggccccatt tgaagaaaag cacaggcgtt attttgattt    240
ccagcgtagg agtggtcaat tgcctttgca gaaggagggt gaggaagttg actacagaaa    300
tgtcctgcat cgtgatggta tctgtactga tggcagtttc cctggatcag ttgaaggctc    360
ctgatctcct ttataggtct cttgcagcaa agcttgcggt tggcatgcct ttcaaggatc    420
tggctactgt                                                            430

<210> SEQ ID NO 30
<211> LENGTH: 528
<212> TYPE: DNA
<213> ORGANISM: Zea mays

<400> SEQUENCE: 30
gacaggcagg gtgcatgctg ctaggaggtt atttgagtac ttacaggcca atggcttgaa     60
```

```
cttccctgta attcatcaca taaatttccc tgaaaccatt gacagagatg gtcttgtcat      120
tggggctggg gccaacgttg gtgctctctt agtcgatggt cttggtgatg gtgtattcct      180
tgaggcggct gaccaggaat ttgagttcct gagggacaca tctttcaact tgctccaagg      240
ttgcaggatg cgcaacacaa aaactgaata tgtgtcttgt ccttcctgcg gccgaacact      300
cttcgacctt caggaaatca gcgctgagat tagcgaaaag acctctcatc tgccacgtgt      360
ttcgatcgct atcatgggtt gtattgtcaa tggaccagga gcgctggctg atgccgattt      420
cggatacgtt ggcggcgctc ccggaaagat cgacctttat attggcacga ccgttatgca      480
gcgcgccatc gccatggacg tgcaactga  cgccttgatc cagctgat                   528
```

```
<210> SEQ ID NO 31
<211> LENGTH: 303
<212> TYPE: DNA
<213> ORGANISM: Zea mays

<400> SEQUENCE: 31
ggggccaacg ttggtgctct cttagtcgat ggtcttggtg atggtgtatt ccttgaggcg       60
gctgaccagg aatttgagtt cctgagggac acatctttca acttgctcca aggttgcagg      120
atgcgcaaca caaaaactga atatgtgtct tgtccttcct gcggccgaac actctttgac      180
cttcaggaaa tcagcgctga gattagagaa aagacctctc atctgccacg tgtttcgatc      240
gctatcatgg gttgtattgt caatggacca ggagagatgg ctgatgccga tttcggatac      300
gtt                                                                    303
```

```
<210> SEQ ID NO 32
<211> LENGTH: 613
<212> TYPE: DNA
<213> ORGANISM: Zea mays
<220> FEATURE:
<221> NAME/KEY: unsure
<222> LOCATION: (1..613)
<223> OTHER INFORMATION: unsure at all n locations

<400> SEQUENCE: 32
cgagatggcg ttccatgccn ggcccttcct cctcttcctc ttcttctgcc ccccgctgg        60 cttggaaaag ggagagaaac tcgcgcactc ggttatcgaa gggaggagcg cgggcgaggg      120
tgaggtttcg cccacacgga gctgcgaggt gtttgtagga tctcctaggt gagcccctgc      180
tgcttggaga cagccatggc caccggcgtg gctccagctc ctctcccaca tgtcagagtg      240
cgtcatgggg gcgtcgggtt caccaggagc gtcgattttg cgaaggtctt gtctgctccc      300
ggtgccggca cgatgagagc aagctcctct agaggcaggg cgctcgtggc gaagagctct      360
agtactggct cggagaccat ggagctcgag ccatcttcag aaggaagccc acttttagta      420
cccaggcaga agtactgtga atcaacacac cagacaagga ggaggaaaac tcgaactgtg      480
atggtgggga atgtgccact tggcagtgat catcccataa ggattcaaac catgacgact      540
tcagatacca aggatgttgc aaaaacagta gaggaggtga tgaggatagc agataaagga      600
gctgatcttg tta                                                         613
```

```
<210> SEQ ID NO 33
<211> LENGTH: 464
<212> TYPE: DNA
<213> ORGANISM: Glycine max

<400> SEQUENCE: 33
```

```
agagcatgaa atcttctgcg aggaaaaggg tgtcaattat cacgaactca atcctggcc    60 aagatattgc tgaacttcaa cctgcatccc caggaagccc tcttttggtt cctaggcaaa   120
agtattgtga atcattgcac aaacccatca ggagaaaaac aagcacagta atggttggta   180
acgtggctat tggtagcgag catcctataa gaattcagac catgactaca actgacacta   240
aggatgttgc tgggacagtt gaacaggtga tgagaatagc agataaagga gctgatattg   300
tacggataac agttcaaggg aagaaagaag ctgatgcttg ttttgagatt aaaaacaccc   360
ttgtgcagaa aaattacaac atacccgtgg tggctgatat tcattttgct ccctctgttg   420 cttttgcgggt agctgaatgc tttgataaga ttcgtgtaaa ccct                   464

<210> SEQ ID NO 34
<211> LENGTH: 705
<212> TYPE: DNA
<213> ORGANISM: Glycine max

<400> SEQUENCE: 34
gtagctgaat gctttgataa gattcgtgta aaccctggaa attttgctga tagacgggct    60
caatttgaaa cattagagta cacagaagaa gactatcaga agaacttga gcatattgaa   120 aaggttttca caccattggt tgagaaatgt aagaaatatg ggagagcaat gcgcattggg   180
acaaaccatg gaagtctttc tgatcgtata atgagctact atggagactc gcctagggga   240
atggtagaat ctgcttttga atttgcaagg atatgccgaa agttagacta tcacaatttt   300
gttttttcta tgaaagcaag caacccagtt atcatggttc aggcataccg cttacttgtg   360
gctgaaatgt atgtccaagg ctgggattat ccattacact tgggtgttac tgaagctgga   420
gaaggtgagg atgggaggat gaagtctgca ataggcattg gaactcttct tcaggatgga   480
ttgggtgata caattagggt ttctctcaca gaaccaccag aggaggagat agacccttgc   540
agaaggttgg caaatcttgg aatgatagct tctgaactcc agaaggggt ggaaccttt   600 gaagaaaagc acagacatta ttttcgactt tcagcgccga tctggtcaat gccagtgca   660 aaaagagggt gaggaggtgg attacagagg tgtactgcac cgtga                  705

<210> SEQ ID NO 35
<211> LENGTH: 564
<212> TYPE: DNA
<213> ORGANISM: Glycine max
<220> FEATURE:
<221> NAME/KEY: unsure
<222> LOCATION: (1..564)
<223> OTHER INFORMATION: unsure at all n locations

<400> SEQUENCE: 35
aagcncggaa ttcggctcga gaggaactca atcctggcc aagatattgc tgaacttcaa    60
cctgtatccc caggaagccc tcttttggtt cctaggcaaa agtattgtga atgattacac   120
aaaactgtca ggagaaaaac aaacacagtg atggttggta acgtggctat tggtagcgag   180
catcctataa gaattcagac catgactacg actgacacta aggatgttgc tgggacagtt   240
gaacaggtga tgagaatagc agataaagga gctgatattg tacggataac agttcaaggg   300
aagaaagaag ctgatgcttg ttttgagatt aaaaacaccc ttgttcagaa aaattacaac   360
atactcgtgg tggctgatat tcattttgct ccctctggtg ctttgcgggt agctgaatgc   420
tttgataaga ttcgtgtaaa ccctggaaat tttgctgata cgggctcaa atttgaaaca   480 ttagagtaca cagatgatga ctatcagaaa gaacttgagc atattgaaaa ggttttcaca   540
ccattggttg agaaatgtaa gaaa                                          564
```

<210> SEQ ID NO 36
<211> LENGTH: 511
<212> TYPE: DNA
<213> ORGANISM: Glycine max

<400> SEQUENCE: 36

```
aaaccatgga agtctttctg atcgtataat gagctactat ggagactcgc ctaggggaat      60
ggtagaatct gcttttgaat ttgcaaggat atgccgaaag ttagactatc acaattttgt     120
tttttctatg aaagcaagca acccagttat catggttcag gcataccgct tacttgtggc     180
tgaaatgtat gtccaaggct gggattatcc attacacttg ggtgttactg aagctggaga     240
aggtgaggat gggaggatga agtctgcaat aggcattgga actcttcttc aggatggatt     300
gggtgataca attagggttt ctctcacaga accaccagag gaggagatag acccttgcag     360
aaggttggca atcttggaa tgatagcttc tgaactccag aaggggtgg aaccttttga      420
agaaaagcac agacattatt ttgactttca gcgccgatct ggtcaattgc cagtgcataa     480
agagggtgag gaggtggatt acagaggtgt a                                    511
```

<210> SEQ ID NO 37
<211> LENGTH: 498
<212> TYPE: DNA
<213> ORGANISM: Glycine max
<220> FEATURE:
<221> NAME/KEY: unsure
<222> LOCATION: (1..498)
<223> OTHER INFORMATION: unsure at all n locations

<400> SEQUENCE: 37

```
cggaggtggc gtgaatgctt tgataagatt cgtgtaaacc ctggaaattt tgctgataga      60
cgggctcaat ttgaaacatg agagtggaca naataagact atgagaaaga acttgagcat     120
attgaaaagg ttttcacacc attggttgag aaatgtaaga aatatgggag agcaatgcgc     180
attgggacaa accatggaag tctttctgat cgtataatga gctactatgg agactcgcct     240
aggggaatgg tagaatctgc ttttgaattt gcaaggatat gccgaaagtt agactatcac     300
aattttgttt tttctatgaa agcaagcaac ccagttatca tggttcaggc ataccgctta     360
cttgtgctg aaatgtatgt ccaaggctgg gattatccat tacacttggg tgttactgaa     420
gctggagaag gtgaggatgg gaggatgaag tctgcaatag gcattggaac tcttcttcag     480
gatggattgg gtgataca                                                   498
```

<210> SEQ ID NO 38
<211> LENGTH: 440
<212> TYPE: DNA
<213> ORGANISM: Glycine max

<400> SEQUENCE: 38

```
gtagctgaat gctttgataa gattcgtgta aaccctggaa attttgttga tagacgggct      60
caatttgaaa cattgagta cacagaagaa gactatcata agaacttga gcatattgaa      120
aaggttttca caccattggt tgagaaatgt aagaaatatg ggagagcaat gcgcattggg     180
acaaaccatg gaagtctttc tgatcgtata atgagctact atggagactc gcctagggga     240
atggtagaat ctgcttttga atttgcaagg atatgccgaa agttagacta tcacaatttt     300
gttttttcta tgaaagcaag caacccagtt atcatggttc aggcataccg cttacttgtg     360
gctgaaatgt atgttcaagg ctgggattat ccattacact gggtgttac tgaagctgga     420
```

```
aaaagtgagg atgggaggat                                                 440
```

```
<210> SEQ ID NO 39
<211> LENGTH: 353
<212> TYPE: DNA
<213> ORGANISM: Glycine max

<400> SEQUENCE: 39
aattcggctc gagaggaact caaatcctgg ccaagatatt gctgaacttc aacctgcatc     60
cccaggaagc cctcttttgg ttcctaggca aaagtattgt gaatcattac acaaaactgt    120
caggagaaaa acaaacacag tgatggttgg taacgtggct attggtagcg agcatcctat    180
aagaattcag accatgacta cgactgacac taaggatgtt gctgggacag ttgaacaggt    240
gatgagaata gcagataaag gagctgatat tgtacggata acagttcaag ggaagaaaga    300
agctgatgct tgttttgaga ttaaaaacac ccttgttcaa aaaattaca aca             353

<210> SEQ ID NO 40
<211> LENGTH: 577
<212> TYPE: DNA
<213> ORGANISM: Glycine max

<400> SEQUENCE: 40 gatgttttg tcgtgtattc tattcctatt gcattcagct cactgatttc aattacaaag     60
tcaattttgt aaatcagagg cagagagagt tgtaaagagc ctctgaattt tgatcacacc    120
acacccttct tctcatctcc accagaaatg gctaccggag ctgctgtgcc aactacgttt    180
tctaccctca agacatggga ttccagtttg gggtttgcaa aaaacataga ttttgtgaga    240
gtttccgata tgaagagcat gaaatcttct gcgaggaaaa gggtgtcaat tatcaggaac    300
tcaaatcctg gccaagatat tgctgaactt caacctgcat ccccaggaag ccctcttttg    360
gttcctaggc aaaagtattg tgaatcattg cacaaaccca tcaggagaaa aacaagcaca    420
gtaatggttg gtaacgtggc tattggtagc gagcatccta agaattca gaccatgact    480 acaactgaca ctaaggatgt tgctgggaca gttgaaccgg tgatgagaat agcagataaa    540
ggagctgata ttgtacggat aacagttcaa gggaaga                              577

<210> SEQ ID NO 41
<211> LENGTH: 551
<212> TYPE: DNA
<213> ORGANISM: Glycine max

<400> SEQUENCE: 41
tggtgctggt tctgatgctg gagcccttct ggtggatggg cttggagatg gacttctttt     60
ggaagcgcca gacaaggatt ttgaatttat tagaaacact tctttcaatt tgttgcaagg    120
ctgcagaatg agaaatacaa agacagagta tgtctcatgt ccatcctgtg cagaacatt    180 gtttgatctt caagaagtaa gtgcacaaat tcgggagaag acatcacacc tccccggtgt    240
ttcgattgca atcatgggat gcattgtaaa tggaccaggg gagatggctg atgcagactt    300
tgggtatgtg ggaggcactc ccggaagat tgacctctat gttgggaaga ctgtggtgaa    360
gcgtggaatt gcaatggagc atgcaaccaa tgccttgatc gatctaataa agaacatgg    420 acgatgggtg gaccctcctg ccgaggagta aaagcaagag cttaattttg agattggcat    480
tcaaggccat agtaagatga gcattgtcat atccaattat tggacacatg taatataagc    540
atacactcaa t                                                          551
```

```
<210> SEQ ID NO 42
<211> LENGTH: 869
<212> TYPE: DNA
<213> ORGANISM: Glycine max

<400> SEQUENCE: 42
gaagcatagt agcatcaatg ccttccttat acagaagact aaaattagca gagtgcatgc      60
ggccaggcgg ttatttgagt acctatccga caattctcta aacttccctg ttattcacca    120
tattcagttc ccaaatggga ttcacagaga tgacttggta attggtgctg gttctgatgc    180
tggagcccct ctggtggatg ggcttggaga tggacttctt ttggaagcgc cagacaagga    240
ttttgaattt attagaaaca cttctttcaa tttgttgcaa ggctgcagaa tgagaaatac    300
aaagacagag tatgtctcat gtccatcctg tggcagaaca ttgtttgatc ttcaagaagt    360
aagtgcacaa attcgggaga agacatcaca cctccctggt gtttcgattg caatcatggg    420
atgcattgta aatggaccag gggagatggc tgatgcagac tttgggtatg tgggaggcac    480
tcccgggaag attgacctct atgttgggaa gactgtggtg aagcgtggaa ttgcaatgga    540
gcatgcaacc aatgccttga tcgatctaat aaaagaacat ggacgatggg tggacccctcc   600
tgccgaggag taaaagcaag agcttaattt tgagattggc attcaaggcc atagtaagat    660
gagcattgtc atatccaatt attgtacaca tgtaatataa gataacactc aatgcttaag    720
tttgagccta gttttaagtt cctttgaga aagatcccaa ttaaagcttg ttgtgaggaa    780
atcgacagct agaacatgta tacagataac agtgtattgc tttgccccat cagccatcaa    840
taataatgag aatctcttag aatagtgcc                                       869

<210> SEQ ID NO 43
<211> LENGTH: 291
<212> TYPE: DNA
<213> ORGANISM: Glycine max
<220> FEATURE:
<221> NAME/KEY: unsure
<222> LOCATION: (1..291)
<223> OTHER INFORMATION: unsure at all n locations

<400> SEQUENCE: 43
gangnactca aatcctgggc caagatattg ctgaacttca nccctgcatc cccaggnngc      60
cctcttttgg ttcctaggca aaagtattgt gaatcattnc cacaaaactg nccaggnaaa    120
aaacaaacac agtgatggtt ggtaacgtgg ctattggtag cgagcatcct ataagaattc    180
agaccatgac tacgacngac actaaggatg ttgctgggac agtngaacng gtgatgagaa    240
tagcagataa aggagctgat attgtacgga taacagttca agggaagaaa g             291

<210> SEQ ID NO 44
<211> LENGTH: 388
<212> TYPE: DNA
<213> ORGANISM: Glycine max

<400> SEQUENCE: 44
cccggtatat ggttcaggca taccgtttac ttgtggctga aatgtatgtc caaggctggg      60
attatccatt acacttgggt gttactgaag ctggagaagg tgaggatggg aggatgaagt    120
ctgcaattgg cattggaact cttcttcagg atggattggg tgatacaatt agggtttctc    180
tcacagaacc accagaagag gagatagatc cttgcagaag gttggcaaat cttggaatga    240
gagcttctga actccagaag gggtggaac cttttgaaga aaagcacaga cattattttg    300
acttccagcg ccgatctggt caattgccag tgcaaaaaga gggtgaggag gtggattaca    360
```

```
                                      -continued
gaggtgcact gcaccgtgac ggttctgt                                      388

<210> SEQ ID NO 45
<211> LENGTH: 211
<212> TYPE: DNA
<213> ORGANISM: Glycine max

<400> SEQUENCE: 45
cccggttatc atggcgcagg cataccgctt acttgtggct gaaatgtatg tccaaggctg    60
ggattatcca ttacacttgg gtgttactga agctggagga ggtgaggatg acaggatgaa   120
gtctgcaatt ggcattggaa ctcttcttca ggatggattg ggtgatacaa ttagggtgtc   180
tcgcacagaa ccaccagaag aggagataga t                                  211

<210> SEQ ID NO 46
<211> LENGTH: 276
<212> TYPE: DNA
<213> ORGANISM: Glycine max

<400> SEQUENCE: 46
tgggcttgga gatggactac ttttggaagc cccggacaag gattttgaat ttattagaaa    60
cacttctttc aatttgttgc aaggctgcag aatgagaaat acaagacag agtatgtctc    120 atgtccatcc tgtggcagaa cattgttga tcttcaagaa gtaagtgcac aaattcggga   180
gaagacatca cacctccctg tgtttcgat tgcaatcatg ggatgcattg taaatggacc   240
aggggagatg gctgatgcag actttgggta tgtggg                             276

<210> SEQ ID NO 47
<211> LENGTH: 399
<212> TYPE: DNA
<213> ORGANISM: Brassica napus

<400> SEQUENCE: 47
cccacgcgtc cgcagggatt cacagggacg agttggtgat ccacgcaggg acatacgctg    60
gggcacttct agtggatgga cttggagatg gtgtaatgct agaagcacct gatcaagact   120
tcgagtttct taggaacact tctttcaact tgttacaagg ctgcaggatg cgtaacacca   180
agacggaata cgtatcgtgc ccgtcttgtg gaagaactct gttcgacttg caagaaatca   240
gcgctgagat cagagaaaag acttcgcatt tgcctggcgt ttcgattgca ataatgggtt   300
gcattgtgaa tggacctggc gaaatggctg atgctgattt cggttatgta ggcggttctc   360
ccgggaaaat cgacctttac gttggaaaga cggtggtca                          399

<210> SEQ ID NO 48
<211> LENGTH: 740
<212> TYPE: PRT
<213> ORGANISM: Arabidopsis thaliana

<400> SEQUENCE: 48

Met Ala Thr Gly Val Leu Pro Ala Pro Val Ser Gly Ile Lys Ile Pro
1               5                   10                  15

Asp Ser Lys Val Gly Phe Gly Lys Ser Met Asn Leu Val Arg Ile Cys
                20                  25                  30

Asp Val Arg Ser Leu Arg Ser Ala Arg Arg Val Ser Val Ile Arg
            35                  40                  45

Asn Ser Asn Gln Gly Ser Asp Leu Ala Glu Leu Gln Pro Ala Ser Glu
        50                  55                  60

Gly Ser Pro Leu Leu Val Pro Arg Gln Lys Tyr Cys Glu Ser Leu His
```

```
                65                  70                  75                  80
Lys Thr Val Arg Arg Lys Thr Arg Thr Val Met Val Gly Asn Val Ala
                    85                  90                  95
Leu Gly Ser Glu His Pro Ile Arg Ile Gln Thr Met Thr Thr Ser Asp
                    100                 105                 110
Thr Lys Asp Ile Thr Gly Thr Val Asp Glu Val Met Arg Ile Ala Asp
                    115                 120                 125
Lys Gly Ala Asp Ile Val Arg Ile Thr Val Gln Gly Lys Lys Glu Ala
                    130                 135                 140
Asp Ala Cys Phe Glu Ile Lys Asp Lys Leu Val Gln Leu Asn Tyr Asn
145                 150                 155                 160
Ile Pro Leu Val Ala Asp Ile His Phe Ala Pro Thr Val Ala Leu Arg
                    165                 170                 175
Val Ala Glu Cys Phe Asp Lys Ile Arg Val Asn Pro Gly Asn Phe Ala
                    180                 185                 190
Asp Arg Arg Ala Gln Phe Glu Thr Ile Asp Tyr Thr Glu Asp Glu Tyr
                    195                 200                 205
Gln Lys Glu Leu Gln His Ile Glu Gln Val Phe Thr Pro Leu Val Glu
                    210                 215                 220
Lys Cys Lys Lys Tyr Gly Arg Ala Met Arg Ile Gly Thr Asn His Gly
225                 230                 235                 240
Ser Leu Ser Asp Arg Ile Met Ser Tyr Tyr Gly Asp Ser Pro Arg Gly
                    245                 250                 255
Met Val Glu Ser Ala Phe Glu Phe Ala Arg Ile Cys Arg Lys Leu Asp
                    260                 265                 270
Tyr His Asn Phe Val Phe Ser Met Lys Ala Ser Asn Pro Val Ile Met
                    275                 280                 285
Val Gln Ala Tyr Arg Leu Leu Val Ala Glu Met Tyr Val His Gly Trp
                    290                 295                 300
Asp Tyr Pro Leu His Leu Gly Val Thr Glu Ala Gly Glu Gly Glu Asp
305                 310                 315                 320
Gly Arg Met Lys Ser Ala Ile Gly Ile Gly Thr Leu Leu Gln Asp Gly
                    325                 330                 335
Leu Gly Asp Thr Ile Arg Val Ser Leu Thr Glu Pro Glu Glu Glu
                    340                 345                 350
Ile Asp Pro Cys Arg Arg Leu Ala Asn Leu Gly Thr Lys Ala Ala Lys
                    355                 360                 365
Leu Gln Gln Gly Ala Pro Phe Glu Glu Lys His Arg His Tyr Phe Asp
                    370                 375                 380
Phe Gln Arg Arg Thr Gly Asp Leu Pro Val Gln Lys Glu Gly Glu Glu
385                 390                 395                 400
Val Asp Tyr Arg Asn Val Leu His Arg Asp Gly Ser Val Leu Met Ser
                    405                 410                 415
Ile Ser Leu Asp Gln Leu Lys Ala Pro Glu Leu Leu Tyr Arg Ser Leu
                    420                 425                 430
Ala Thr Lys Leu Val Val Gly Met Pro Phe Lys Asp Leu Ala Thr Val
                    435                 440                 445
Asp Ser Ile Leu Leu Arg Glu Leu Pro Val Asp Asp Gln Val Ala
                    450                 455                 460
Arg Leu Ala Leu Lys Arg Leu Ile Asp Val Ser Met Gly Val Ile Ala
465                 470                 475                 480
Pro Leu Ser Glu Gln Leu Thr Lys Pro Leu Pro Asn Ala Met Val Leu
                    485                 490                 495
```

```
Val Asn Leu Lys Glu Leu Ser Gly Gly Ala Tyr Lys Leu Leu Pro Glu
            500                 505                 510

Gly Thr Arg Leu Val Val Ser Leu Arg Gly Asp Glu Pro Tyr Glu Glu
            515                 520                 525

Leu Glu Ile Leu Lys Asn Ile Asp Ala Thr Met Ile Leu His Asp Val
            530                 535                 540

Pro Phe Thr Glu Asp Lys Val Ser Arg Val His Ala Ala Arg Arg Leu
545                 550                 555                 560

Phe Glu Phe Leu Ser Glu Asn Ser Val Asn Phe Pro Val Ile His His
                565                 570                 575

Ile Asn Phe Pro Thr Gly Ile His Arg Asp Glu Leu Val Ile His Ala
            580                 585                 590

Gly Thr Tyr Ala Gly Gly Leu Leu Val Asp Gly Leu Gly Asp Gly Val
            595                 600                 605

Met Leu Glu Ala Pro Asp Gln Asp Phe Asp Phe Leu Arg Asn Thr Ser
            610                 615                 620

Phe Asn Leu Leu Gln Gly Cys Arg Met Arg Asn Thr Lys Thr Glu Tyr
625                 630                 635                 640

Val Ser Cys Pro Ser Cys Gly Arg Thr Leu Phe Asp Leu Gln Glu Ile
                645                 650                 655

Ser Ala Glu Ile Arg Glu Lys Thr Ser His Leu Pro Gly Val Ser Ile
            660                 665                 670

Ala Ile Met Gly Cys Ile Val Asn Gly Pro Gly Glu Met Ala Asp Ala
            675                 680                 685

Asp Phe Gly Tyr Val Gly Gly Ser Pro Gly Lys Ile Asp Leu Tyr Val
690                 695                 700

Gly Lys Thr Val Val Lys Arg Gly Ile Ala Met Thr Glu Ala Thr Asp
705                 710                 715                 720

Ala Leu Ile Gly Leu Ile Lys Glu His Gly Arg Trp Val Asp Pro Pro
                725                 730                 735

Val Ala Asp Glu
            740

<210> SEQ ID NO 49
<211> LENGTH: 603
<212> TYPE: PRT
<213> ORGANISM: Oryza sativa

<400> SEQUENCE: 49

Met Val Gly Asn Val Pro Leu Gly Ser Asp His Pro Ile Arg Ile Gln
1               5                   10                  15

Thr Met Thr Thr Ser Asp Thr Lys Asp Val Ala Lys Thr Val Glu Glu
            20                  25                  30

Val Met Arg Ile Ala Asp Lys Gly Ala Asp Phe Val Arg Ile Thr Val
            35                  40                  45

Gln Gly Arg Lys Glu Ala Asp Ala Cys Phe Glu Ile Lys Asn Thr Leu
        50                  55                  60

Val Gln Lys Asn Tyr Asn Ile Pro Leu Val Ala Asp Ile His Phe Ala
65                  70                  75                  80

Pro Thr Val Ala Leu Arg Val Ala Glu Cys Phe Asp Lys Ile Arg Val
                85                  90                  95

Asn Pro Gly Asn Phe Ala Asp Arg Arg Ala Gln Phe Glu Gln Leu Glu
            100                 105                 110

Tyr Thr Glu Asp Asp Tyr Gln Lys Glu Leu Glu His Ile Glu Lys Val
```

```
                115                 120                 125
Pro Asn Ile Ser Leu Phe Ser Val Asn Leu Val Phe Ser Pro Leu Val
        130                 135                 140
Glu Lys Cys Lys Gln Tyr Gly Arg Ala Met Arg Ile Gly Thr Asn His
145                 150                 155                 160
Gly Ser Leu Ser Asp Arg Ile Met Ser Tyr Tyr Gly Asp Ser Pro Arg
                165                 170                 175
Gly Met Val Glu Ser Ala Leu Glu Phe Ala Arg Ile Cys Arg Lys Leu
                180                 185                 190
Asp Phe His Asn Phe Val Phe Ser Met Lys Ala Ser Asn Pro Val Ile
            195                 200                 205
Met Val Gln Ala Tyr Arg Leu Leu Val Ala Glu Met Tyr Asn Leu Gly
    210                 215                 220
Trp Asp Tyr Pro Leu His Leu Gly Val Thr Glu Ala Gly Glu Gly Glu
225                 230                 235                 240
Asp Gly Arg Met Lys Ser Ala Ile Gly Ile Gly Thr Leu Leu Met Asp
                245                 250                 255
Gly Leu Gly Asp Thr Ile Arg Val Ser Leu Thr Glu Pro Pro Glu Glu
                260                 265                 270
Glu Ile Asp Pro Cys Arg Arg Leu Ala Asn Leu Gly Thr His Ala Ala
                275                 280                 285
Asp Leu Gln Ile Gly Val Ala Pro Phe Glu Glu Lys His Arg Arg Tyr
        290                 295                 300
Phe Asp Phe Gln Arg Arg Ser Gly Gln Leu Pro Leu Gln Lys Glu Ala
305                 310                 315                 320
Pro Glu Leu Leu Tyr Arg Ser Leu Ala Ala Lys Leu Val Val Gly Met
                    325                 330                 335
Pro Phe Lys Asp Leu Ala Thr Val Asp Ser Ile Leu Leu Lys Glu Leu
                340                 345                 350
Pro Pro Val Glu Asp Ala Gln Ala Arg Leu Ala Leu Lys Arg Leu Val
                355                 360                 365
Asp Ile Ser Met Gly Val Leu Thr Pro Leu Ser Glu Gln Leu Thr Lys
        370                 375                 380
Pro Leu Pro His Ala Ile Ala Leu Val Asn Val Asp Glu Leu Ser Ser
385                 390                 395                 400
Gly Ala His Lys Leu Leu Pro Glu Gly Thr Arg Leu Ala Val Thr Leu
                405                 410                 415
Arg Gly Asp Glu Ser Tyr Glu Gln Leu Asp Leu Leu Lys Gly Val Asp
                420                 425                 430
Asp Ile Thr Met Leu Leu His Ser Val Pro Tyr Gly Glu Glu Lys Thr
        435                 440                 445
Gly Arg Val His Ala Ala Arg Arg Leu Phe Glu Tyr Leu Glu Thr Asn
    450                 455                 460
Gly Leu Asn Phe Pro Val Ile His His Ile Glu Phe Pro Lys Ser Val
465                 470                 475                 480
Asn Arg Asp Asp Leu Val Ile Gly Ala Gly Ala Asn Val Gly Ala Leu
                485                 490                 495
Leu Val Asp Gly Leu Gly Asp Gly Val Leu Leu Glu Ala Ala Asp Gln
                500                 505                 510
Glu Phe Glu Phe Leu Arg Asp Thr Ser Phe Asn Leu Leu Gln Gly Cys
            515                 520                 525
Arg Met Arg Asn Thr Lys Thr Ile Ala Ile Met Gly Cys Ile Val Asn
    530                 535                 540
```

-continued

```
Gly Pro Gly Glu Met Ala Asp Ala Asp Phe Gly Tyr Val Gly Gly Ala
545                 550                 555                 560

Pro Gly Lys Ile Asp Leu Tyr Val Gly Lys Thr Val Val Gln Arg Gly
                565                 570                 575

Ile Ala Met Glu Gly Ala Thr Asp Ala Leu Ile Gln Leu Ile Lys Asp
                580                 585                 590

His Gly Arg Trp Val Asp Pro Val Glu Glu
            595                 600
```

<210> SEQ ID NO 50
<211> LENGTH: 372
<212> TYPE: PRT
<213> ORGANISM: Escherichia coli

<400> SEQUENCE: 50

```
Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
                20                  25                  30

Met Thr Asn Thr Arg Thr Thr Asp Val Glu Ala Thr Val Asn Gln Ile
            35                  40                  45

Lys Ala Leu Glu Arg Val Gly Ala Asp Ile Val Arg Val Ser Val Pro
50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
            100                 105                 110

Gly Asn Glu Glu Arg Ile Arg Met Val Val Asp Cys Ala Arg Asp Lys
        115                 120                 125

Asn Ile Pro Ile Arg Ile Gly Val Asn Ala Gly Ser Leu Glu Lys Asp
130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
    210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
    290                 295                 300

Cys Val Val Asn Gly Pro Gly Glu Ala Leu Val Ser Thr Leu Gly Val
```

```
                305                 310                 315                 320
Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365

Gln Val Glu Lys
    370
```

<210> SEQ ID NO 51
<211> LENGTH: 25
<212> TYPE: DNA
<213> ORGANISM: Artificial Sequence
<220> FEATURE:
<223> OTHER INFORMATION: Designed primer named CINCO

<400> SEQUENCE: 51
cgctgcccag aatggacctc cctag                                             25

<210> SEQ ID NO 52
<211> LENGTH: 26
<212> TYPE: DNA
<213> ORGANISM: Artificial Sequence
<220> FEATURE:
<223> OTHER INFORMATION: Designed primer named SEIS

<400> SEQUENCE: 52
cagccgcgtt ttgacttgaa acgtgc                                            26

<210> SEQ ID NO 53
<211> LENGTH: 27
<212> TYPE: DNA
<213> ORGANISM: Artificial Sequence
<220> FEATURE:
<223> OTHER INFORMATION: Designed primer named MPD-Nde5'

<400> SEQUENCE: 53
gccatatgac cgtttacaca gcatccg                                           27

<210> SEQ ID NO 54
<211> LENGTH: 35
<212> TYPE: DNA
<213> ORGANISM: Artificial Sequence
<220> FEATURE:
<223> OTHER INFORMATION: Designed primer named MPD-Eco3'

<400> SEQUENCE: 54
tcgaattctc attattcctt tggtagacca gtctt                                  35

<210> SEQ ID NO 55
<211> LENGTH: 30
<212> TYPE: DNA
<213> ORGANISM: Artificial Sequence
<220> FEATURE:
<223> OTHER INFORMATION: Designed primer named hPMK1

<400> SEQUENCE: 55
tggttaacat atggccccgc tgggaggcgc                                        30

<210> SEQ ID NO 56
<211> LENGTH: 40
<212> TYPE: DNA
<213> ORGANISM: Artificial Sequence

```
<220> FEATURE:
<223> OTHER INFORMATION: Designed primer named hPMK4

<400> SEQUENCE: 56
aggttaactc aattaaagtc tggagcggat aaattctatc                              40

<210> SEQ ID NO 57
<211> LENGTH: 25
<212> TYPE: DNA
<213> ORGANISM: Artificial Sequence
<220> FEATURE:
<223> OTHER INFORMATION: Designed primer named UNO

<400> SEQUENCE: 57
cgggcctcgt ttggctgtcg cactg                                              25

<210> SEQ ID NO 58
<211> LENGTH: 25
<212> TYPE: DNA
<213> ORGANISM: Artificial Sequence
<220> FEATURE:
<223> OTHER INFORMATION: Designed primer named DOS

<400> SEQUENCE: 58
cgcgggtgga aggaccttgt ggagg                                              25

<210> SEQ ID NO 59
<211> LENGTH: 33
<212> TYPE: DNA
<213> ORGANISM: Artificial Sequence
<220> FEATURE:
<223> OTHER INFORMATION: Designed primer named MK-Hpa5'

<400> SEQUENCE: 59
aagttaacat atgtcattac cgttcttaac ttc                                     33

<210> SEQ ID NO 60
<211> LENGTH: 34
<212> TYPE: DNA
<213> ORGANISM: Artificial Sequence
<220> FEATURE:
<223> OTHER INFORMATION: Designed primer named MK-Hpa3'

<400> SEQUENCE: 60
cggttaactc attatgaagt ccatggtaaa ttcg                                    34

<210> SEQ ID NO 61
<211> LENGTH: 30
<212> TYPE: DNA
<213> ORGANISM: Artificial Sequence
<220> FEATURE:
<223> OTHER INFORMATION: Designed primer named idi5X

<400> SEQUENCE: 61
cccctcgaga ttatgcaaac ggaacacgtc                                         30

<210> SEQ ID NO 62
<211> LENGTH: 31
<212> TYPE: DNA
<213> ORGANISM: Artificial Sequence
<220> FEATURE:
<223> OTHER INFORMATION: Designed primer named idi3X

<400> SEQUENCE: 62
ggctcgagtt atttaagctg ggtaaatgca g                                       31
```

```
<210> SEQ ID NO 63
<211> LENGTH: 32
<212> TYPE: DNA
<213> ORGANISM: Artificial Sequence
<220> FEATURE:
<223> OTHER INFORMATION: Designed primer named pBAD-mut1

<400> SEQUENCE: 63
ctgagagtgc accatctgcg gtgtgaaata cc                              32

<210> SEQ ID NO 64
<211> LENGTH: 40
<212> TYPE: DNA
<213> ORGANISM: Artificial Sequence
<220> FEATURE:
<223> OTHER INFORMATION: Designed primer named pBAD-Link1

<400> SEQUENCE: 64
aattctaagg aggtttaaac taaggaggta cgtaaggagg                      40

<210> SEQ ID NO 65
<211> LENGTH: 40
<212> TYPE: DNA
<213> ORGANISM: Artificial Sequence
<220> FEATURE:
<223> OTHER INFORMATION: Designed primer named pBAD-Link2

<400> SEQUENCE: 65
tcgacctcct tacgtacctc cttagtttaa acctccttag                      40

<210> SEQ ID NO 66
<211> LENGTH: 21
<212> TYPE: DNA
<213> ORGANISM: Artificial Sequence
<220> FEATURE:
<223> OTHER INFORMATION: Designed primer named pBAD-D2

<400> SEQUENCE: 66
tcatactccc gccattcaga g                                          21

<210> SEQ ID NO 67
<211> LENGTH: 21
<212> TYPE: DNA
<213> ORGANISM: Artificial Sequence
<220> FEATURE:
<223> OTHER INFORMATION: Designed primer named pBAD-U3

<400> SEQUENCE: 67
ccgccaaaac agccaagctt g                                          21

<210> SEQ ID NO 68
<211> LENGTH: 28
<212> TYPE: DNA
<213> ORGANISM: Artificial Sequence
<220> FEATURE:
<223> OTHER INFORMATION: Designed primer named pRS-L1

<400> SEQUENCE: 68
gatccgttta aacgcccggg cggccgcg                                   28

<210> SEQ ID NO 69
<211> LENGTH: 28
<212> TYPE: DNA
<213> ORGANISM: Artificial Sequence
<220> FEATURE:
<223> OTHER INFORMATION: Designed primer named pRS-L2
```

```
<400> SEQUENCE: 69
aattcgcggc cgcccgggcg tttaaacg                                          28

<210> SEQ ID NO 70
<211> LENGTH: 22
<212> TYPE: DNA
<213> ORGANISM: Artificial Sequence
<220> FEATURE:
<223> OTHER INFORMATION: Designed primer named 1PE

<400> SEQUENCE: 70
cgcggtgtgg gtgagcatga tg                                                22

<210> SEQ ID NO 71
<211> LENGTH: 30
<212> TYPE: DNA
<213> ORGANISM: Artificial Sequence
<220> FEATURE:
<223> OTHER INFORMATION: Designed primer named 22PE

<400> SEQUENCE: 71
aaatctcccg ggttacccgt ctgttactgc                                        30

<210> SEQ ID NO 72
<211> LENGTH: 33
<212> TYPE: DNA
<213> ORGANISM: Artificial Sequence
<220> FEATURE:
<223> OTHER INFORMATION: Designed primer named 3PE

<400> SEQUENCE: 72
gcgtttaaac tggacgaagc gcgtcgaatt gac                                    33

<210> SEQ ID NO 73
<211> LENGTH: 22
<212> TYPE: DNA
<213> ORGANISM: Artificial Sequence
<220> FEATURE:
<223> OTHER INFORMATION: Designed primer named 4PE

<400> SEQUENCE: 73
tgcacgaccg cccagttgtt cc                                                22

<210> SEQ ID NO 74
<211> LENGTH: 21
<212> TYPE: DNA
<213> ORGANISM: Artificial Sequence
<220> FEATURE:
<223> OTHER INFORMATION: Designed primer named CAT1

<400> SEQUENCE: 74
gagtccgaat aaatacctgt g                                                 21

<210> SEQ ID NO 75
<211> LENGTH: 21
<212> TYPE: DNA
<213> ORGANISM: Artificial Sequence
<220> FEATURE:
<223> OTHER INFORMATION: Designed primer named CAT4

<400> SEQUENCE: 75
ccgaatttct gccattcatc c                                                 21

<210> SEQ ID NO 76
```

-continued

```
<211> LENGTH: 21
<212> TYPE: DNA
<213> ORGANISM: Artificial Sequence
<220> FEATURE:
<223> OTHER INFORMATION: Designed primer named 0PE

<400> SEQUENCE: 76
tgggctttgt cacgagcaca c                                          21

<210> SEQ ID NO 77
<211> LENGTH: 21
<212> TYPE: DNA
<213> ORGANISM: Artificial Sequence
<220> FEATURE:
<223> OTHER INFORMATION: Designed primer named 5PE

<400> SEQUENCE: 77
ggcccatagc aaaaccgaca g                                          21

<210> SEQ ID NO 78
<211> LENGTH: 372
<212> TYPE: PRT
<213> ORGANISM: Escherichia coli

<400> SEQUENCE: 78

Met His Asn Gln Ala Pro Ile Gln Arg Arg Lys Ser Thr Arg Ile Tyr
  1               5                  10                  15

Val Gly Asn Val Pro Ile Gly Asp Gly Ala Pro Ile Ala Val Gln Ser
                 20                  25                  30

Met Thr Asn Thr Arg Thr Thr Asp Val Glu Ala Thr Val Asn Gln Ile
             35                  40                  45

Lys Ala Leu Glu Arg Val Gly Ala Asp Ile Val Arg Val Ser Val Pro
         50                  55                  60

Thr Met Asp Ala Ala Glu Ala Phe Lys Leu Ile Lys Gln Gln Val Asn
 65                  70                  75                  80

Val Pro Leu Val Ala Asp Ile His Phe Asp Tyr Arg Ile Ala Leu Lys
                 85                  90                  95

Val Ala Glu Tyr Gly Val Asp Cys Leu Arg Ile Asn Pro Gly Asn Ile
                100                 105                 110

Gly Asn Glu Glu Arg Ile Arg Met Val Val Asp Cys Ala Arg Asp Lys
            115                 120                 125

Asn Ile Pro Ile Arg Ile Gly Val Asn Ala Gly Ser Leu Glu Lys Asp
        130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
    210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
```

-continued

```
            260                 265                 270
Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
    290                 295                 300

Cys Val Asn Gly Pro Gly Glu Ala Leu Val Ser Thr Leu Gly Val
305                 310                 315                 320

Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365

Gln Val Glu Lys
    370

<210> SEQ ID NO 79
<211> LENGTH: 740
<212> TYPE: PRT
<213> ORGANISM: Arabidopsis thaliana

<400> SEQUENCE: 79

Met Ala Thr Gly Val Leu Pro Ala Pro Val Ser Gly Ile Lys Ile Pro
1               5                   10                  15

Asp Ser Lys Val Gly Phe Gly Lys Ser Met Asn Leu Val Arg Ile Cys
            20                  25                  30

Asp Val Arg Ser Leu Arg Ser Ala Arg Arg Val Ser Val Ile Arg
        35                  40                  45

Asn Ser Asn Gln Gly Ser Asp Leu Ala Glu Leu Gln Pro Ala Ser Glu
    50                  55                  60

Gly Ser Pro Leu Leu Val Pro Arg Gln Lys Tyr Cys Glu Ser Leu His
65                  70                  75                  80

Lys Thr Val Arg Arg Lys Thr Arg Thr Val Met Val Gly Asn Val Ala
                85                  90                  95

Leu Gly Ser Glu His Pro Ile Arg Ile Gln Thr Met Thr Thr Ser Asp
            100                 105                 110

Thr Lys Asp Ile Thr Gly Thr Val Asp Glu Val Met Arg Ile Ala Asp
        115                 120                 125

Lys Gly Ala Asp Ile Val Arg Ile Thr Val Gln Gly Lys Lys Glu Ala
    130                 135                 140

Asp Ala Cys Phe Glu Ile Lys Asp Lys Leu Val Gln Leu Asn Tyr Asn
145                 150                 155                 160

Ile Pro Leu Val Ala Asp Ile His Phe Ala Pro Thr Val Ala Leu Arg
                165                 170                 175

Val Ala Glu Cys Phe Asp Lys Ile Arg Val Asn Pro Gly Asn Phe Ala
            180                 185                 190

Asp Arg Arg Ala Gln Phe Glu Thr Ile Asp Tyr Thr Glu Asp Glu Tyr
        195                 200                 205

Gln Lys Glu Leu Gln His Ile Glu Gln Val Phe Thr Pro Leu Val Glu
    210                 215                 220

Lys Cys Lys Lys Tyr Gly Arg Ala Met Arg Ile Gly Thr Asn His Gly
225                 230                 235                 240

Ser Leu Ser Asp Arg Ile Met Ser Tyr Tyr Gly Asp Ser Pro Arg Gly
                245                 250                 255
```

```
Met Val Glu Ser Ala Phe Glu Phe Ala Arg Ile Cys Arg Lys Leu Asp
            260                 265                 270

Tyr His Asn Phe Val Phe Ser Met Lys Ala Ser Asn Pro Val Ile Met
            275                 280                 285

Val Gln Ala Tyr Arg Leu Leu Val Ala Glu Met Tyr Val His Gly Trp
        290                 295                 300

Asp Tyr Pro Leu His Leu Gly Val Thr Glu Ala Gly Glu Gly Glu Asp
305                 310                 315                 320

Gly Arg Met Lys Ser Ala Ile Gly Ile Gly Thr Leu Leu Gln Asp Gly
                325                 330                 335

Leu Gly Asp Thr Ile Arg Val Ser Leu Thr Glu Pro Pro Glu Glu Glu
            340                 345                 350

Ile Asp Pro Cys Arg Arg Leu Ala Asn Leu Gly Thr Lys Ala Ala Lys
            355                 360                 365

Leu Gln Gln Gly Ala Pro Phe Glu Glu Lys His Arg His Tyr Phe Asp
        370                 375                 380

Phe Gln Arg Arg Thr Gly Asp Leu Pro Val Gln Lys Glu Gly Glu Glu
385                 390                 395                 400

Val Asp Tyr Arg Asn Val Leu His Arg Asp Gly Ser Val Leu Met Ser
                405                 410                 415

Ile Ser Leu Asp Gln Leu Lys Ala Pro Glu Leu Leu Tyr Arg Ser Leu
            420                 425                 430

Ala Thr Lys Leu Val Val Gly Met Pro Phe Lys Asp Leu Ala Thr Val
            435                 440                 445

Asp Ser Ile Leu Leu Arg Glu Leu Pro Pro Val Asp Asp Gln Val Ala
        450                 455                 460

Arg Leu Ala Leu Lys Arg Leu Ile Asp Val Ser Met Gly Val Ile Ala
465                 470                 475                 480

Pro Leu Ser Glu Gln Leu Thr Lys Pro Leu Pro Asn Ala Met Val Leu
                485                 490                 495

Val Asn Leu Lys Glu Leu Ser Gly Gly Ala Tyr Lys Leu Leu Pro Glu
            500                 505                 510

Gly Thr Arg Leu Val Val Ser Leu Arg Gly Asp Glu Pro Tyr Glu Glu
            515                 520                 525

Leu Glu Ile Leu Lys Asn Ile Asp Ala Thr Met Ile Leu His Asp Val
        530                 535                 540

Pro Phe Thr Glu Asp Lys Val Ser Arg Val His Ala Ala Arg Arg Leu
545                 550                 555                 560

Phe Glu Phe Leu Ser Glu Asn Ser Val Asn Phe Pro Val Ile His His
                565                 570                 575

Ile Asn Phe Pro Thr Gly Ile His Arg Asp Glu Leu Val Ile His Ala
            580                 585                 590

Gly Thr Tyr Ala Gly Leu Leu Val Asp Gly Leu Gly Asp Gly Val
            595                 600                 605

Met Leu Glu Ala Pro Asp Gln Asp Phe Asp Phe Leu Arg Asn Thr Ser
        610                 615                 620

Phe Asn Leu Leu Gln Gly Cys Arg Met Arg Asn Thr Lys Thr Glu Tyr
625                 630                 635                 640

Val Ser Cys Pro Ser Cys Gly Arg Thr Leu Phe Asp Leu Gln Glu Ile
                645                 650                 655

Ser Ala Glu Ile Arg Glu Lys Thr Ser His Leu Pro Gly Val Ser Ile
            660                 665                 670

Ala Ile Met Gly Cys Ile Val Asn Gly Pro Gly Glu Met Ala Asp Ala
```

-continued

```
                       675                 680                 685

Asp Phe Gly Tyr Val Gly Gly Ser Pro Gly Lys Ile Asp Leu Tyr Val
        690                 695                 700

Gly Lys Thr Val Val Lys Arg Gly Ile Ala Met Thr Glu Ala Thr Asp
705                 710                 715                 720

Ala Leu Ile Gly Leu Ile Lys Glu His Gly Arg Trp Val Asp Pro Pro
                725                 730                 735

Val Ala Asp Glu
        740

<210> SEQ ID NO 80
<211> LENGTH: 155
<212> TYPE: DNA
<213> ORGANISM: Arabidopsis thaliana

<400> SEQUENCE: 80
aaaaatcgga aaatggcga ctggagtatt gccagctccg gtttctggga tcaagatacc      60
ggattcgaaa gtcgggtttg gtaaaagcat gaatcttgtg agaatttgtg atgttaggag    120
tctaagatct gctgatgagt agatttcata aaagt                               155

<210> SEQ ID NO 81
<211> LENGTH: 42
<212> TYPE: PRT
<213> ORGANISM: Arabidopsis thaliana

<400> SEQUENCE: 81

Met Ala Thr Gly Val Leu Pro Ala Pro Val Ser Gly Ile Lys Ile Pro
1               5                  10                  15

Asp Ser Lys Val Gly Phe Gly Lys Ser Met Asn Leu Val Arg Ile Cys
            20                  25                  30

Asp Val Arg Ser Leu Arg Ser Ala Asp Glu
        35                  40

<210> SEQ ID NO 82
<211> LENGTH: 45
<212> TYPE: DNA
<213> ORGANISM: Arabidopsis thaliana

<400> SEQUENCE: 82
atgagaggat cgcaycayca ycaycaycay cayggatccg catgc                     45

<210> SEQ ID NO 83
<211> LENGTH: 12
<212> TYPE: PRT
<213> ORGANISM: Arabidopsis thaliana

<400> SEQUENCE: 83

Met Arg Gly Ser His His His His His His Gly Ser
1               5                  10

<210> SEQ ID NO 84
<211> LENGTH: 59
<212> TYPE: DNA
<213> ORGANISM: Arabidopsis thaliana

<400> SEQUENCE: 84
atgagaggat cgcaycayca ycaycaycay ggatctgctg atgagtagat ttcgcatgc      59
```

-continued

```
<210> SEQ ID NO 85
<211> LENGTH: 15
<212> TYPE: PRT
<213> ORGANISM: Arabidopsis thaliana

<400> SEQUENCE: 85

Met Arg Gly Ser His His His His His His Gly Ser Ala Asp Glu
1               5                   10                  15
```

METHYL-D-ERYTHRITOL PHOSPHATE PATHWAY GENES

This application claims the benefit under 35 U.S.C. § 119(e) of U.S. Provisional Patent Application Ser. No. 60/223,483 filed Aug. 7, 2000, which application is herein incorporated by reference.

A paper copy of the Sequence Listing and a computer readable form of the sequence listing on diskette, containing the file named 16516-107 seq listing.txt, which is 133,010 bytes in size (measured in MS-DOS), and which was created on Aug. 6, 2001, are herein incorporated by reference.

The present invention is in the field of plant genetics and biochemistry. More specifically, the invention relates to genes associated with the methyl-D-erythritol phosphate (MEP) pathway. The present invention provides and includes nucleic acid molecules, proteins, and antibodies associated with the genes of the MEP pathway and also provides methods utilizing such agents, for example in gene isolation, gene analysis and the production of transgenic plants. Moreover, the present invention includes transgenic plants modified to express proteins associated with the MEP pathway and methods for the production of products from the MEP pathway.

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans. Tocopherols function, in part, by stabilizing the lipid bilayer of biological membranes, reducing polyunsaturated fatty acid (PUFA) free radicals generated by lipid oxidation, and scavenging oxygen free radicals, lipid peroxy radicals and singlet oxygen species.

$\alpha$-Tocopherol, often referred to as vitamin E, belongs to a class of lipid-soluble antioxidants that includes $\alpha$, $\beta$, $\gamma$, and $\delta$-tocopherols and $\alpha$, $\beta$, $\gamma$, and $\delta$-tocotrienols. Although $\alpha$, $\beta$, $\gamma$, and $\delta$-tocopherols and $\alpha$, $\beta$, $\gamma$, and $\delta$-tocotrienols are sometimes referred to collectively as "vitamin E", vitamin E is more appropriately defined chemically as $\alpha$-tocopherol. $\alpha$-Tocopherol is significant for human health, in part because it is readily absorbed and retained by the body, and therefore has a higher degree of bioactivity than other tocopherol species. However, other tocopherols such as $\beta$, $\gamma$, and $\delta$-tocopherols, also have significant health and nutritional benefits.

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with $\alpha$-tocopherol the predominant tocopherol species found in green, photosynthetic plant tissues. Leaf tissue can contain from 10–50 $\mu$g of total tocopherols per gram fresh weight, but most of the world's major staple crops (e.g., rice, corn, wheat, potato) produce low to extremely low levels of total tocopherols, of which only a small percentage is $\alpha$-tocopherol. Oil seed crops generally contain much higher levels of total tocopherols, but $\alpha$-tocopherol is present only as a minor component in most oilseeds.

The recommended human daily dietary intake of 15–30 mg of vitamin E is quite difficult to achieve from the average American diet. For example, it would take over 750 grams of spinach leaves in which $\alpha$-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single isomer. Furthermore, supplements tend to be relatively expensive, and the general population is disinclined to take vitamin supplements on a regular basis.

In addition to the health benefits of tocopherols, increased $\alpha$-tocopherol levels in crops have been associated with enhanced stability and extended shelf life of fresh and processed plant products. Further, tocopherol supplementation of swine, beef, and poultry feeds has been shown to significantly increase meat quality and extend the shelf life of post-processed meat products by retarding post-processing lipid oxidation, which contributes to undesirable flavor components.

Tocopherols are a member of the class of compounds referred to as the isoprenoids. Other isoprenoids include carotenoids, gibberellins, terpenes, chlorophyll and abscisic acid. The chloroplasts of higher plants exhibit interconnected biochemical pathways leading to secondary metabolites including tocopherols. One tocopherol biosynthetic pathway in higher plants involves condensation of homogentisic acid and phytylpyrophosphate to form 2-methyl-6 phytylplastoquinol.

This plant tocopherol pathway can be divided into four parts: 1) synthesis of homogentisic acid, which contributes to the aromatic ring of tocopherol; 2) synthesis of phytylpyrophosphate, which contributes to the side chain of tocopherol; 3) joining of HGA and phytylpyrophosphate via a prenyltransferase followed by a subsequent cyclization; 4) and S-adenosyl methionine-dependent methylation of an aromatic ring, which affects the relative abundance of each of the tocopherol species.

Homogentisic acid (HGA) is the common precursor to both tocopherols and plastoquinones. In at least some bacteria the synthesis of HGA is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the myra genes of *Erwinia herbicola* and *Escherichia coli*. The tyrA gene product catalyzes the production of prephenate from chorismate, as well as the subsequent dehydrogenation of prephenate to form p-hydroxyphenylpyruvate (p-HPP), the immediate precursor to HGA. p-HPP is then converted to HGA by hydroxyphenylpyruvate dioxygenase (HPPD). In contrast, plants are believed to lack prephenate dehydrogenase activity, and it is generally believed that the synthesis in plants of HGA from chorismate occurs via the synthesis and conversion of the intermediate arogenate. Because pathways involved in HGA synthesis are also responsible for tyrosine formation, any alterations in these pathways can also result in the alteration in tyrosine synthesis and the synthesis of other aromatic amino acids.

HGA is then combined with either phytyl-pyrophosphate or solanyl-pyrophosphate by phytyl/prenyl transferase to form methyl-plastoquinols, which are precursors to plastoquinones and tocopherols. The major structural difference between each of the tocopherol species is the position of the methyl groups around the phenyl ring. This methylation process is S-adenosyl methionine-dependent. Methyl Transferase 1 (MT1) catalyzes the formation of plastoquinol-9 and -tocopherol by methylation of the 7 position. Subsequent methylation at the 5 position of -tocopherol by -tocopherol methyl-transferase generates the biologically active -tocopherol.

Phytylpyrophosphate, which is the central constituent of the tocopherol side chain, is formed from geranylgeranyl-diphosphate (GGDP). GGDP is itself produced via a biosynthetic pathway in which isopentenyl diphosphate (IPP) plays a major role. IPP is a central intermediate in the production of isoprenoids. Two pathways that generate IPP have been reported: a cytoplasmic-based pathway referred to as the mevalonate pathway; and a plastid-based pathway referred to as the MEP pathway. The cytoplasmic-based pathway involves the enzymes acetoacetyl CoA thiolase, HMGCoA synthase, HMGCoA reductase, mevalonate kinase, phosphomevalonate kinase, and mevalonate pyrophosphate decarboxylase.

Evidence for the existence of an alternative, plastid-based, isoprenoid biosynthetic pathway recently emerged from studies in the research groups of Rohmer and Arigoni, who found that the isotope labeling patterns observed in studies on certain eubacterial and plant terpenoids could not be explained in terms of the mevalonate pathway. Eisenreich et al., *Chem. Bio.* 5:R221–233 (1998); Rohmer, *Prog. Drug. Res.* 50:135–154 (1998); Rohmner, 2 *Comprehensive Natural Products Chemistry* 45–68, Barton and Nakanishi (eds.), Pergamon Press, Oxford, England (1999). Arigoni and coworkers subsequently showed that 1-deoxyxylulose, or a derivative thereof, serves as an intermediate of the novel pathway, now referred to as the MEP pathway. Rohmer et al., *Biochem. J.* 295:517–524 (1993); Schwarz, Ph.D. thesis, Eidgenössiche Technische Hochschule, Zurich, Switzerland (1994).

In the first step of the MEP pathway, DXP synthase, an enzyme encoded by the dxs gene, catalyzes the formation of 1-deoxy-D-xylulose-5-phosphate (DXP) from one molecule each of D-glyceraldehyde-3-phosphate and pyruvate. DXP is then converted into 2-C-methyl-D-erythritol-4-phosphate (MEP) by DXP reductoisomerase, which is encoded by the dxr gene. The conversion of MEP into 4-diphosphocytidyl-2-C-methyl-D-erythritol (CDP-ME) is catalyzed by CDP-ME synthase, which is encoded by the ygbP gene. CDP-ME kinase, which is encoded by the ychB gene, catalyzes the conversion of CDP-ME into 4-diphosphocytidyl-2-C-methyl-D-erythritol 2-phosphate (CDP-MEP). CDP-MEP is then converted into 2-C-methyl-D-erythritol-2,4-cyclodiphosphate by ME-CDP synthase, which is encoded by the ygbB gene. The ygbP and ygbB genes are tightly linked on the *E. coli* genome. Herz et al., *PNAS* 97(6): 2485–2490 (2000).

Identification of further genes included in the MEP pathway will provide new approaches to increasing tocopherol levels in plants, which is a topic of the present application.

SUMMARY OF THE INVENTION

The present invention provides a novel gene essential to the MEP pathway: gcpE. gcpE is tightly linked to ygbP and ygbB. Expression of GCPE protein) in organisms such as plants can increase the levels of tocopherol substrates such as isopentyl diphosphate (IPP) and dimethylallyl diphosphate (DMAPP) biosynthesis. The present invention also provides transgenic organisms expressing a GCPE protein, which can nutritionally enhance food and feed sources.

In particular, the present invention includes and provides a substantially purified nucleic acid molecule that encodes a protein comprising an amino acid sequence selected from the group consisting of SEQ ID NOs: 4 and 48 through 50. The present invention also includes and provides a substantially purified nucleic acid molecule that encodes a protein comprising an amino acid sequence of SEQ ID NO: 4.

Further provided by the present invention is a substantially purified nucleic acid molecule that encodes a protein comprising an amino acid sequence of SEQ ID NO: 48.

The present invention includes and provides a substantially purified nucleic acid molecule that encodes a protein comprising an amino acid sequence of SEQ ID NO: 49. The present invention also includes and provides a substantially purified nucleic acid molecule that encodes a protein comprising an amino acid sequence of SEQ ID NO: 50. Further provided by the present invention is a substantially purified nucleic acid molecule that encodes a GCPE protein, where the nucleic acid molecule comprises a nucleic acid sequence selected from the group consisting of SEQ ID NOs: 1 through 3, 5 through 47, and complements thereof.

The present invention includes and provides a recombinant nucleic acid molecule comprising as operably linked components: (A) a promoter; and (B) a heterologous nucleic acid molecule that encodes an amino sequence selected from the group consisting of SEQ ID NOs: 4 and 48 through 50. The present invention also includes and provides transformed cells comprising such nucleic acid molecules.

Further provided by the present invention is a transgenic plant comprising a recombinant nucleic acid molecule comprising as operably linked components: (A) a promoter; and (B) a heterologous nucleic acid molecule that encodes an amino sequence selected from the group consisting of SEQ ID NOs: 4 and 48 through 50.

The present invention includes and provides such a transgenic plant that exhibits an increased tocopherol level relative to a plant with a similar genetic background but lacking the recombinant nucleic acid molecule. Also provided are seeds derived from such transgenic plants, and oil derived from such seeds. The present invention includes and provides such a transgenic plant that exhibits an increased monoterpene level relative to a plant with a similar genetic background but lacking the recombinant nucleic acid molecule. The present invention includes and provides such a transgenic plant that exhibits an increased carotenoid level relative to a plant with a similar genetic background but lacking the recombinant nucleic acid molecule. The present invention includes and provides such a transgenic plant that exhibits an increased tocotrienol level relative to a plant with a similar genetic background but lacking the recombinant nucleic acid molecule.

The present invention includes and provides such a transgenic plant that produces a seed with an increased tocopherol level relative to a plant with a similar genetic background but lacking the recombinant nucleic acid molecule. The present invention includes and provides such a transgenic plant that produces a seed with an increased monoterpene level relative to a plant with a similar genetic background but lacking the recombinant nucleic acid molecule. The present invention includes and provides such a transgenic plant that produces a seed with an increased carotenoid level relative to a plant with a similar genetic background but lacking the recombinant nucleic acid molecule. The present invention includes and provides such a transgenic plant which produces a seed with an increased tocotrienol level relative to a plant with a similar genetic background but lacking the recombinant nucleic acid molecule.

The present invention includes and provides a recombinant nucleic acid molecule comprising as operably linked components: (A) an exogenous promoter; and (B) a nucleic acid sequence selected from the group consisting of SEQ ID NOs: 1 through 3, 5 through 47, and complements thereof.

The present invention also includes and provides transformed cells comprising such nucleic acid molecules.

Further provided by the present invention is a transgenic plant comprising a recombinant nucleic acid molecule comprising as operably linked components: (A) an exogenous promoter; and (B) a nucleic acid sequence selected from the group consisting of SEQ ID NOs: 1 through 3, 5 through 47, and complements thereof. The present invention includes and provides such a transgenic plant which is selected from the group consisting of *Brassica campestris, Brassica napus,* canola, castor bean, coconut, cotton, crambe, linseed, maize, mustard, oil palm, peanut, rapeseed, rice, safflower, sesame, soybean, sunflower, and wheat. The present invention includes and provides such a trangenic plant which is selected from the group consisting of coconut, crambe, maize, oil palm, peanut, rapeseed, safflower, sesame, soybean, and sunflower.

The present invention further includes and provides a seed derived from such a transgenic plant. Also provided are oil and meal derived from such seeds. The present invention includes and provides such a seed which exhibits an increased tocopherol level relative to seed from a plant having a similar genetic background but lacking the recombinant nucleic acid molecule. The present invention includes and provides such a seed which exhibits an increased -tocopherol level relative to seed from a plant having a similar genetic background but lacking the recombinant nucleic acid molecule. The present invention includes and provides such a seed which exhibits an increased monoterpene level relative to seed from a plant having a similar genetic background but lacking the recombinant nucleic acid molecule. The present invention includes and provides such a seed which exhibits an increased carotenoid level relative to seed from a plant having a similar genetic background but lacking the recombinant nucleic acid molecule. The present invention includes and provides such a seed which exhibits an increased tocotrienol level relative to seed from a plant having a similar genetic background but lacking the recombinant nucleic acid molecule.

The present invention includes and provides a recombinant nucleic acid molecule comprising as operably linked components: (A) a promoter that functions in a plant cell to cause production of an mRNA molecule; and (B) a nucleic acid sequence that hybridizes under moderate stringency conditions to a nucleic acid sequence selected from the group consisting of SEQ ID NOs: 1 through 3, 5 through 47, and complements thereof.

The present invention includes and provides a recombinant nucleic acid molecule comprising as operably linked components: (A) a promoter that functions in a plant cell to cause production of an mRNA molecule; and (B) a nucleic acid sequence that has greater than 85% identity to a nucleic acid sequence selected from the group consisting of SEQ ID NOs: 1 through 3, 5 through 47, and complements thereof.

The present invention includes and provides a substantially purified protein comprising an amino acid sequence selected from the group consisting of SEQ ID NOs: 4, 48, and 49. The present invention also includes and provides an antibody capable of specifically binding a protein comprising an amino acid sequence selected from the group consisting of SEQ ID NOs: 4, 48 and 49.

The present invention includes and provides a transgenic plant comprising a nucleic acid molecule that encodes a GCPE protein, where the nucleic acid molecule comprises a promoter operably linked to a heterologous nucleic acid sequence selected from the group consisting of SEQ ID NOs: 1 through 3, 5 through 47, and complements thereof. The present invention includes and provides such a transgenic plant where the the promoter is a seed-specific promoter. The present invention includes and provides such a transgenic plant where the seed-specific promoter is selected from the group consisting of napin, phaseolin, zein, soybean trypsin inhibitor, ACP, stearoyl-ACP desaturase, soybean a' subunit of b-conglycinin (soy 7s), and oleosin promoters.

The present invention includes and provides such a transgenic plant, where the plant exhibits an increased isoprenoid compound level relative to a plant with a similar genetic background but lacking the heterologous nucleic acid sequence. The present invention includes and provides such a transgenic plant, where the isoprenoid compound is selected from the group consisting of tocotrienols, tocopherols, terpenes, gibberellins, carotenoids, and xanthophylls. The present invention includes and provides such a transgenic plant, where the isoprenoid compound is a monoterpene. The present invention includes and provides such a transgenic plant, where the isoprenoid compound is selected from the group consisting of IPP and DMAPP. The present invention includes and provides such a transgenic plant, where the plant exhibits an increased tocopherol level relative to a plant with a similar genetic background but lacking the heterologous nucleic acid sequence. Also included and provided are feedstock, plant parts, and seeds derived from such plants. Further provided are containers of such seeds.

The present invention includes and provides a method of producing a transgenic plant with an increased isoprenoid compound level comprising: (A) transforming the plant with a nucleic acid molecule to produce a transgenic plant, where the nucleic acid molecule comprises a nucleic acid sequence selected from the group consisting of SEQ ID NOs: 1 through 3, 5 through 47, and complements thereof; and (B) growing the transgenic plant.

The present invention includes and provides a method of producing a transgenic plant having seed with an increased isoprenoid compound level comprising: (A) transforming the plant with a nucleic acid molecule to produce a transgenic plant, where the nucleic acid molecule encodes a protein with an amino acid sequence selected from the group consisting of SEQ ID NOs: 4 and 48–50; and (B) growing the transgenic plant.

BRIEF DESCRIPTION OF THE DRAWINGS

FIG. 4 sets forth an alignment between proteins encoded by the gcpE gene from *E. coli* (SEQ ID NO: 78) and clone 135H1 from *A. thaliana* (SEQ ID NO: 79).

FIG. 5 sets forth cloning of a truncated *Arabidopsis* cDNA to create pQE-AGH.

DESCRIPTION OF THE NUCLEIC AND AMINO ACID SEQUENCES

Figure 1:
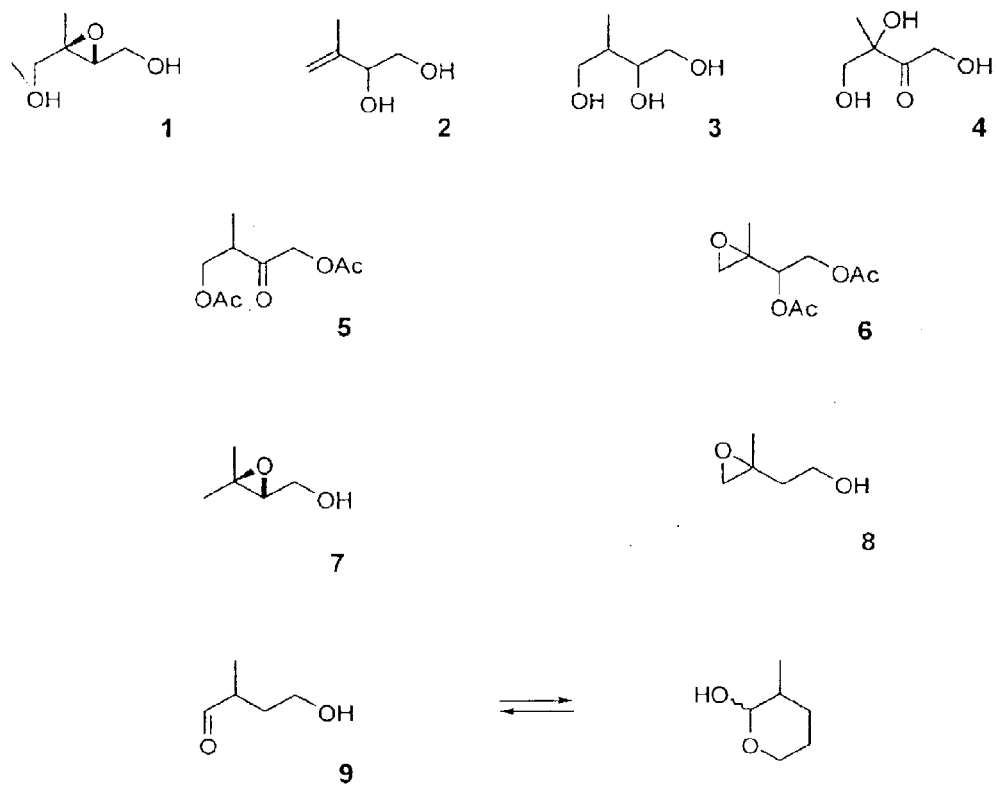
FIG. 1 sets forth chemical compounds that were determined as non-GCPE reaction products.

SEQ ID NO: 1 is an *Arabidopsis thaliana* nucleotide sequence of a gcpE gene.

SEQ ID NO: 2 is a rice nucleotide sequence of a gcpE gene.

SEQ ID NO: 3 is an *E. coli* nucleotide sequence of a gcpE gene.

SEQ ID NO: 4 is an amino acid sequence derived from a rice gcpE gene.

SEQ ID NO: 5 is a partial *A. thaliana* nucleotide sequence of a gcpE gene.

SEQ ID NO: 6 is a partial soybean nucleotide sequence of a gcpE gene.

SEQ ID NO: 7 is a partial tomato nucleotide sequence of a gcpE gene.

SEQ ID NO: 8 is a partial *Mesembryanthemun crystallinum* nucleotide sequence of a gcpE gene.

SEQ ID NO: 9 is a partial rice nucleotide sequence of a gcpE gene.

SEQ ID NO: 10 is a partial maize nucleotide sequence of a gcpE gene.

SEQ ID NO: 11 is a partial Loblolly pine nucleotide sequence of a gcpE gene.

SEQ ID NO: 12 is a partial *Physcomitrella patens* nucleotide sequence of a gcpE gene.

SEQ ID NOs: 13 through 20 are partial *A. thaliana* nucleotide sequences of a gcpE gene.

SEQ ID NOs: 21 through 32 are partial maize nucleotide sequences of a gcpE gene.

SEQ ID NOs: 33 through 46 are partial soybean nucleotide sequences of a gcpE gene.

SEQ ID NO: 47 is a partial *Brassica napus* nucleotide sequence of a gcpE gene.

SEQ ID NO: 48 is an amino acid sequence derived from an *A. thaliana* gcpE gene.

SEQ ID NO: 49 is an amino acid sequence derived from a rice gcpE gene.

SEQ ID NO: 50 is an amino acid sequence derived from an *E. coli* gcpE gene.

SEQ ID NOs: 51 through 77 are primer nucleotide sequences.

SEQ ID NO: 78 is an *E. coli* amino acid sequence derived from the gcpE gene.

SEQ ID NO: 79 is an *A. thaliana* amino acid sequence derived from clone 135H1.

SEQ ID NO: 80 is a partial *A. thaliana* nucleotide sequence of a gcpE gene.

SEQ ID NO: 81 is an amino acid sequence derived from an*A. thaliana* gcpE gene.

SEQ ID NO: 82 is a partial *A. thaliana* nucleotide sequence of a gcpE gene.

SEQ ID NO: 83 is an amino acid sequence derived from an *A. thaliana* gcpE gene.

SEQ ID NO: 84 is a partial *A. thaliana* nucleotide sequence of a gcpE gene.

SEQ ID NO: 85 is an amino acid sequence derived from an *A. thaliana* gcpE gene.

Definitions

The following definitions are provided as an aid to understanding the detailed description of the present invention.

The abbreviation "EP" refers to patent applications and patents published by the European Patent Office, and the term "WO" refers to patent applications published by the World Intellectual Property Organization. "PNAS" refers to *Proc. Natl. Acad. Sci. (U.S.A.)*.

"Amino acid" and "amino acids" refer to all naturally occurring L-amino acids. This definition is meant to include norleucine, norvaline, ornithine, homocysteine, and homoserine.

"Chromosome walking" means a process of extending a genetic map by successive hybridization steps.

The phrases "coding sequence," "structural sequence," and "structural nucleic acid sequence" refer to a physical structure comprising an orderly arrangement of nucleic acids. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

A nucleic acid molecule is said to be the "complement" of another nucleic acid molecule if they exhibit complete complementarity, i.e., every nucleotide of one of the molecules is complementary to a nucleotide of the other. Two molecules are "minimally complementary" if they can hybridize to one another with sufficient stability to remain annealed to one another under at least conventional "low-stringency" conditions. Similarly, the molecules are "complementary" if they can hybridize to one another with sufficient stability to remain annealed to one another under conventional "high-stringency" conditions. Conventional stringency conditions are described by Sambrook et al., *Molecular Cloning: A Laboratory Manual*, Second Edition, Cold Spring Harbor Laboratory Press, Cold Spring Harbor, N.Y. (1989); Haymes et al., *Nucleic Acid Hybridization, A Practical Approach*, IRL Press, Washington, D.C. (1985).

The phrases "DNA sequence," "nucleic acid sequence," and "nucleic acid molecule" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like. "Nucleic acid" refers to deoxyribonucleic acid (DNA) and ribonucleic acid (RNA).

An "elite soybean line" is any soybean line that has resulted from breeding and selection for superior agronomic performance. Elite soybean lines are commercially available to farmers or soybean breeders, e.g., HARTZ™ variety H4452 Roundup Ready™ (HARTZ SEED, Stuttgart, Ark., USA); QP4544 (Asgrow Seeds, Des Moines, Iowa, USA); DeKalb variety CX445 (DeKalb, Ill.).

"Exogenous genetic material" is any genetic material, whether naturally occurring or otherwise, from any source that is capable of being inserted into any organism.

The term "expression" refers to the transcription of a gene to produce the corresponding mRNA and translation of this MRNA to produce the corresponding gene product (i.e., a peptide, polypeptide, or protein). The term "expression of antisense RNA" refers to the transcription of a DNA to produce a first RNA molecule capable of hybridizing to a second RNA molecule. Formation of the RNA—RNA hybrid inhibits translation of the second RNA molecule to produce a gene product.

"Fungi" as used herein includes the phyla Ascomycota, Basidiomycota, Chytridiomycota and Zygomycota, as well as the Oomycota and all mitosporic fungi, and "filamentous fungi" include all filamentous forms of the subdivision Eumycota and Oomycota. These terms are defined in Hawksworth et al., in: Ainsworth and Bisby's *Dictionary of The Fungi*, $8^{th}$ edition, CAB International, University Press, Cambridge, UK (1995).

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

As used herein, a "homolog protein" molecule or fragment thereof is a counterpart protein molecule or fragment thereof in a second species (e.g., maize GCPE is a homolog of *Arabidopsis* GCPE). A homolog can also be generated by molecular evolution or DNA shuffling techniques, so that the molecule retains at least one functional or structure characteristic of the original protein (see, e.g., U.S. Pat. No. 5,811,238).

The phrase "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e. does not naturally occur in that particular cell or organism).

"Hybridization" refers to the ability of a strand of nucleic acid to join with a complementary strand via base pairing. Hybridization occurs when complementary nucleic acid sequences in the two nucleic acid strands contact one another under appropriate conditions.

The "MEP pathway" is the pathway associated with the biosynthesis of isopentenyl diphosphate or dimethylallyl-diphosphate where deoxy-D-xylulose-5-phosphate or a derivative thereof serves as an intermediate.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

"Phenotype" refers to traits exhibited by an organism resulting from the interaction of genotype and environment, such as disease resistance, pest tolerance, environmental tolerance such as tolerance to abiotic stress, male sterility, quality improvement or yield etc.

"Polyadenylation signal" or "polyA signal" refers to a nucleic acid sequence located 3' to a coding region that promotes the addition of adenylate nucleotides to the 3' end of the mRNA transcribed from the coding region.

The term "promoter" or "promoter region" refers to a nucleic acid sequence, usually found upstream (5') to a coding sequence, which is capable of directing transcription of a nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The term "protein" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide molecule" includes any protein that is modified by any biological or non-biological process.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein.

"Recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

"Regeneration" refers to the process of growing a plant from a plant cell or plant tissue (e.g., plant protoplast or explant).

"Regulatory sequence" refers to a nucleotide sequence located upstream (5'), within, or downstream (3') to a coding sequence. Transcription and expression of the coding sequence is typically impacted by the presence or absence of the regulatory sequence.

An antibody or peptide is said to "specifically bind" to a protein or peptide molecule of the invention if such binding is not competitively inhibited by the presence of non-related molecules.

"Substantially homologous" refers to two sequences which are at least 90% identical in sequence, as measured by the BestFit program described herein (Version 10; Genetics Computer Group, Inc., University of Wisconsin Biotechnology Center, Madison, Wis.), using default parameters.

"Substantially purified" refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

"Transcription" refers to the process of producing an RNA copy from a DNA template. "Transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

"Transgenic" refers to organisms into which exogenous nucleic acid sequences are integrated. "Transgenic plant" refers to a plant where an introduced nucleic acid is stably introduced into a genome of the plant, for example, the nuclear or plastid genomes.

"Vector" refers to a plasmid, cosmid, bacteriophage, or virus that carries exogenous DNA into a host organism.

"Yeast" as used herein includes Ascosporogenous yeast (Endomycetales), Basidiosporogenous yeast and yeast belonging to the Fungi Imperfecti (Blastomycetes), as defined in Skinner et al. (1980).

DETAILED DESCRIPTION OF THE PREFERRED EMBODIMENTS

One skilled in the art may refer to general reference texts for detailed descriptions of known techniques discussed herein or equivalent techniques. These texts include Ausubel et al., *Current Protocols in Molecular Biology*, John Wiley and Sons, Inc. (1995); Sambrook et al., *Molecular Cloning,*

*A Laboratory Manual* (2d ed.), Cold Spring Harbor Press, Cold Spring Harbor, N.Y. (1989); Birren et al., *Genome Analysis: A Laboratory Manual,* volumes 1 through 4, Cold Spring Harbor Press, Cold Spring Harbor, N.Y. (1997–1999); *Plant Molecular Biology: A Laboratory Manual,* Clark (ed.), Springer, N.Y. (1997); Richards et al., *Plant Breeding Systems* (2d ed.), Chapman & Hall, The University Press, Cambridge (1997); and Maliga et al., *Methods in Plant Molecular Biology,* Cold Spring Harbor Press, Cold Spring Harbor, N.Y. (1995). These texts can, of course, also be referred to in making or using an aspect of the invention.

Utilizing a methodology for the isolation and characterization of essential MEP pathway genes, an essential and novel gene, termed gcpE, was isolated. gcpE is tightly linked to ygbP and ygbB, which are other MEP pathway genes. As an essential MEP pathway component, enhanced expression or overexpression of GCPE in a variety of organisms such as plants can result in higher levels of tocopherol precursors such as IPP and DMAPP and ultimately in enhanced levels of tocopherols in such organisms. Moreover, the present invention provides a number of agents, for example, nucleic acid molecules encoding a GCPE protein, and provides uses of such agents.

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be substantially purified. The agents of the invention may also be recombinant.

It is understood that any of the agents of the invention can be substantially purified and/or be biologically active and/or recombinant. It is also understood that the agents of the invention may be labeled with reagents that facilitate detection of the agent, e.g., fluorescent labels, chemical labels, modified bases, and the like.

A. Nucleic Acid Molecules

Agents of the invention include nucleic acid molecules. In a preferred aspect of the present invention the nucleic acid molecule comprises a nucleic acid sequence which encodes a GCPE protein. In a preferred embodiment, the GCPE protein is derived from an organism having a MEP pathway. Examples of GCPE proteins are those proteins having an amino acid sequence selected from the group consisting of SEQ ID NO: 4, 48, 49, or 50.

In another preferred aspect of the present invention the nucleic acid molecule comprises a nucleic acid sequence that is selected from: (1) any of SEQ ID NOs: 1 through 3, 5 through 47, complements thereof, or fragments of these sequences; (2) the group consisting of SEQ ID NOs: 1, 2, complements thereof, and fragments of these sequences; (3) the group consisting of SEQ ID NOs: 1, 2, 3, complements thereof and fragments of these sequences; (4) the group consisting of SEQ ID NOs: 1, 2, 13 through 47, complements thereof and fragments of these sequences; (5) the group consisting of SEQ ID NOs: 5 through 12, complements thereof and fragments of these sequences; or (6) the group consisting of SEQ ID NOs: 1 through 3, 5 through 47, complements thereof and fragments of these sequences.

In a further aspect of the present invention the nucleic acid molecule comprises a nucleic acid sequence encoding an amino acid sequence selected from: (1) any of SEQ ID NOs: 4, 48, 49 or 50; (2) the group consisting of SEQ ID NO: 4, 48, and 49 and fragments of these sequences; or (3) the group consisting of SEQ ID NO: 4, 48, 49, 50 and fragments of these sequences.

It is understood that in a further aspect of the nucleic acid sequences of the present invention can encode a protein which differs from any of the proteins in that amino acid have been deleted, substituted or added without altering the function. For example, it is understood that codons capable of coding for such conservative amino acid substitutions are known in the art.

The present invention provides nucleic acid molecules that hybridize to the above-described nucleic acid molecules. Nucleic acid hybridization is a technique well known to those of skill in the art of DNA manipulation. The hybridization properties of a given pair of nucleic acids is an indication of their similarity or identity.

The nucleic acid molecules preferably hybridize, under low, moderate, or high stringency conditions, with a nucleic acid sequence selected from: (1) any of SEQ ID NOs: 1 through 3, 5 through 47, or complements thereof; (2) the group consisting of SEQ ID NOs: 1, 2, and complements thereof; (3) the group consisting of SEQ ID NOs: 1, 2, 3, and complements thereof; (4) the group consisting of SEQ ID NOs: 1, 2, 13 through 47, and complements thereof; (5) the group consisting of SEQ ID NOs: 5 through 12, and complements thereof; or (6) the group consisting of SEQ ID NOs: 1 through 3, 5 through 47, and complements thereof. Fragments of these sequences are also contemplated.

The hybridization conditions typically involve nucleic acid hybridization in about 0.1× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 20° C. to about 70° C. for several hours to overnight. The stringency conditions are preferably provided by 6×SSC, 5×Denhardt's solution, 100 mg/mL fish sperm DNA, and 0.1% (w/v) SDS, with an incubation at 55° C. for several hours.

The hybridization is generally followed by several wash steps. The wash compositions generally comprise 0.1× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Low stringency conditions may be used to select nucleic acid sequences with lower sequence identities to a target nucleic acid sequence. One may wish to employ conditions such as about 6.0×SSC to about 10×SSC, at temperatures ranging from about 20° C. to about 55° C., and preferably a nucleic acid molecule will hybridize to one or more of the above-described nucleic acid molecules under low stringency conditions of about 6.0×SSC and about 45° C. In a preferred embodiment, a nucleic acid molecule will hybridize to one or more of the above-described nucleic acid molecules under moderately stringent conditions, for example at about 2.0×SSC and about 65° C. In a particularly preferred embodiment, a nucleic acid molecule of the present invention will hybridize to one or more of the above-described nucleic acid molecules under high stringency conditions such as 0.2×SSC and about 65° C.

In an alternative embodiment, the nucleic acid molecule comprises a nucleic acid sequence that is greater than 85% identical, and more preferably greater than 86, 87, 88, 89, 90, 91, 92, 93, 94, 95, 96, 97, 98, or 99% identical to a nucleic acid sequence selected from the group consisting of SEQ ID NO: 1 through 3 and 5 through 47, complements thereof, and fragments of any of these sequences.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

The present invention also provides nucleic acid molecule fragments that hybridize to the above-described nucleic acid molecules and complements thereof, fragments of nucleic acid molecules that exhibit greater than 80%, 85%, 90%, 95% or 99% sequence identity with the above-described nucleic acid molecules and complements thereof, or fragments of any of these molecules.

Fragment nucleic acid molecules may consist of significant portion(s) of, or indeed most of, the nucleic acid molecules of the invention. In an embodiment, the fragments are between about 3000 and about 1000 consecutive nucleotides, about 1800 and about 150 consecutive nucleotides, about 1500 and about 500 consecutive nucleotides, about 1300 and about 250 consecutive nucleotides, about 1000 and about 200 consecutive nucleotides, about 800 and about 150 consecutive nucleotides, about 500 and about 100 consecutive nucleotides, about 300 and about 75 consecutive nucleotides, about 100 and about 50 consecutive nucleotides, about 50 and about 25 consecutive nucleotides, or about 20 and about 10 consecutive nucleotides long of a nucleic molecule of the present invention.

In another embodiment, the fragment comprises at least 20, 30, 40, 50, 60, 70, 80, 90, 100, 150, 200, 250, 500, or 750 consecutive nucleotides of a nucleic acid sequence of the present invention.

Exemplary Uses

Nucleic acid molecules of the invention and fragments thereof may be employed to obtain other nucleic acid molecules from the same species (e.g., nucleic acid molecules from maize may be utilized to obtain other nucleic acid molecules from maize). Exemplary nucleic acid molecules that may be obtained include, but are not limited to, nucleic acid molecules that encode the complete coding sequence of a protein and promoters and flanking sequences of such molecules, and nucleic acid molecules that encode for other isozymes or gene family members.

Nucleic acid molecules of the invention and fragments thereof may also be employed to obtain nucleic acid homologs. Such homologs include the nucleic acid molecules of other plants or other organisms, including the nucleic acid molecules that encode, in whole or in part, protein homologs of other plant species or other organisms, or sequences of genetic elements, such as promoters and transcriptional regulatory elements.

Promoters that may be isolated include, but are not limited to promoters of cell enhanced, cell specific, tissue enhanced, tissue specific, developmentally or environmentally regulated expression profiles. Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

The above-described molecules can be readily obtained by using the above-described nucleic acid molecules or fragments thereof to screen cDNA or genomic libraries obtained from such plant species. These methods are known to those of skill in the art, as are methods for forming such libraries. In one embodiment, such sequences are obtained by incubating nucleic acid molecules of the present invention with members of genomic libraries and recovering clones that hybridize to such nucleic acid molecules thereof. In a second embodiment, methods of chromosome walking or inverse PCR may be used to obtain such sequences.

Any of a variety of methods may be used to obtain one or more of the above-described nucleic acid molecules. Automated nucleic acid synthesizers may be employed for this purpose. In lieu of such synthesis, the disclosed nucleic acid molecules may be used to define a pair of primers that can be used with the polymerase chain reaction to amplify and obtain any desired nucleic acid molecule or fragment.

In a preferred embodiment, nucleic acid molecules having SEQ ID NOs: 1 through 3 and 5 through 47, and complements thereof, and fragments of any of these sequences can be utilized to obtain such homologs. Such homolog molecules may differ in their nucleotide sequences from those found in one or more of SEQ ID NOs: 1 through 3, and 5 through 47 or complements thereof because complete complementarity is not needed for stable hybridization. The nucleic acid molecules of the invention therefore also include molecules that, although capable of specifically hybridizing with the nucleic acid molecules may lack "complete complementarity."

In a preferred embodiment, the molecules are obtained from alfalfa, apple, *Arabidopsis,* banana, barley, *Brassica, Brassica campestris, Brassica napus,* broccoli, cabbage, canola, castor bean, chrysanthemum, citrus, coconut, coffee, cotton, crambe, cranberry, cucumber, Cuphea, dendrobium, dioscorea, eucalyptus, fescue, fir, garlic, gladiolus, grape, hordeum, lentils, lettuce, liliacea, linseed, maize, millet, muskmelon, mustard, oat, oil palm, oilseed rape, onion, an ornamental plant, papaya, pea, peanut, pepper, perennial ryegrass, *Phaseolus,* pine, poplar, potato, rapeseed (including Canola and High Erucic Acid varieties), rice, rye, safflower, sesame, sorghum, soybean, strawberry, sugarbeet, sugarcane, sunflower, tea, tomato, triticale, turf grasses, and wheat.

In a more preferred embodiment, the molecules are obtained from *Brassica campestris, Brassica napus,* canola, castor bean, coconut, cotton, crambe, linseed, maize, mustard, oil palm, peanut, rapeseed (including Canola and High Erucic Acid varieties), rice, safflower, sesame, soybean, sunflower, and wheat, and in a particularly preferred embodiment from coconut, crambe, maize, oil palm, peanut, rapeseed (including Canola and High Erucic Acid varieties), safflower, sesame, soybean, and sunflower.

The Sequence Analysis Software Package™ (Version 10; Genetics Computer Group, Inc., University of Wisconsin Biotechnology Center, Madison, Wis.) contains a number of other useful sequence analysis tools for identifying homologs of the presently disclosed nucleotide and amino acid sequences. For example, programs such as "BLAST", "FastA", "TfastA", "FastX", and "TfastX" can be used to search for sequences similar to a query sequence. See, e.g., Altschul et al., *Journal of Molecular Biology* 215: 403–410 (1990); Lipman and Pearson, *Science* 227:1435–1441 (1985); Pearson and Lipman, 85:2444–2448 (1988); Pearson, "Rapid and Sensitive Sequence Comparison with FASTP and FASTA" in *Methods in Enzymology*, (R. Doolittle, ed.), 183:63–98, Academic Press, San Diego, Calif., USA (1990).

Short nucleic acid sequences having the ability to specifically hybridize to complementary nucleic acid sequences may be produced and utilized in the present invention, e.g., as probes to identify the presence of a complementary nucleic acid sequence in a given sample. Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related sequences from other species).

Use of these probes or primers may greatly facilitate the identification of transgenic plants which contain the presently disclosed promoters and structural nucleic acid sequences. Such probes or primers may also be used to screen cDNA or genomic libraries for additional nucleic acid sequences related to or sharing homology with the presently disclosed promoters and structural nucleic acid sequences. The probes may also be PCR probes, which are nucleic acid molecules capable of initiating a polymerase activity while in a double-stranded structure with another nucleic acid.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule. Various methods for determining the structure of PCR probes and PCR techniques exist in the art. Computer-generated searches using programs such as Primer3 (www-genome.wi.mit. edu/cgi-bin/primer/primer3.cgi), STSPipeline (www-genome.wi.mit.edu/cgi-bin/www-STS$_{13}$Pipeline), or GeneUp (Pesole et al., *BioTechniques* 25:112–123, 1998), for example, can be used to identify potential PCR primers.

B. Protein and Peptide Molecules

Agents of the invention include proteins, peptide molecules, and fragments thereof encoded by nucleic acid agents of the invention. Preferred classes of protein and peptide molecules include: (1) GCPE proteins and peptide molecules; (2) GCPE proteins and peptide molecules derived from an organism having a MEP pathway; (3) GCPE proteins and peptide molecules derived from plants; and (4) GCPE proteins and peptide molecules derived from oilseed plants, including, but not limited to *Brassica campestris, Brassica napus*, canola, castor bean, coconut, cotton, crambe, linseed, maize, mustard, oil palm, peanut, rapeseed, rice, safflower, sesame, soybean, sunflower, and wheat.

Other preferred proteins are those proteins having an amino acid sequence: (1) selected from the group consisting of SEQ ID NOs: 4, 48, 49, and 50; (2) selected from the group consisting of SEQ ID NOs: 4, 48 and 49; (3) selected from the group consisting of SEQ ID NOs: 4 and 49; (4) of SEQ ID NO: 4; (5) of SEQ ID NO: 48; (6) of SEQ ID NO: 49; and (7) of SEQ ID NO: 50.

In another preferred aspect of the present invention the protein or peptide molecule is encoded by a nucleic acid agent of the invention, including, but not limited to a nucleic acid sequence that is selected from: (1) any of SEQ ID NOs: 1 through 3, 5 through 47, complements thereof, or fragments of these sequences; (2) the group consisting of SEQ ID NOs: 1, 2, complements thereof, and fragments of these sequences; (3) the group consisting of SEQ ID NOs: 1, 2, 3, complements thereof and fragments of these sequences; (4) the group consisting of SEQ ID NOs: 1, 2, 13 through 47, complements thereof and fragments of these sequences; (5) the group consisting of SEQ ID NOs: 5 through 12, complements thereof and fragments of these sequences; or (6) the group consisting of SEQ ID NOs: 1 through 3, 5 through 47, complements thereof and fragments of these sequences.

Any of the nucleic acid agents of the invention may be linked with additional nucleic acid sequences to encode fusion proteins. The additional nucleic acid sequence preferably encodes at least one amino acid, peptide, or protein. Many possible fusion combinations exist. For instance, the fusion protein may provide a "tagged" epitope to facilitate detection of the fusion protein, such as GST, GFP, FLAG, or polyHIS. Such fusions preferably encode between 1 and about 50 amino acids, more preferably between about 5 and about 30 additional amino acids, and even more preferably between about 5 and about 20 amino acids.

Alternatively, the fusion may provide regulatory, enzymatic, cell signaling, or intercellular transport functions. For example, a sequence encoding a plastid transit peptide may be added to direct a fusion protein to the chloroplasts within seeds. Such fusion partners preferably encode between 1 and about 1000 additional amino acids, more preferably between about 5 and about 500 additional amino acids, and even more preferably between about 10 and about 250 amino acids.

The above-described protein or peptide molecules may be produced via chemical synthesis, or more preferably, by expression in a suitable bacterial or eukaryotic host. Suitable methods for expression are described by Sambrook et al., supra, or similar texts. Fusion protein or peptide molecules of the invention are preferably produced via recombinant means. These proteins and peptide molecules may be derivatized to contain carbohydrate or other moieties (such as keyhole limpet hemocyanin, etc.).

Also contemplated are protein and peptide agents, including fragments and fusions thereof, in which conservative, non-essential or non-relevant amino acid residues have been added, replaced or deleted. A further particularly preferred class of protein is a GCPE protein, in which conservative, non-essential or non-relevant amino acid residues have been added, replaced or deleted. Computerized means for designing modifications in protein structure are known in the art. See, e.g., Dahiyat and Mayo, *Science* 278:82–87 (1997).

A protein of the invention can also be a homolog protein. In a preferred embodiment, the nucleic acid molecules of the present invention, complements thereof, and fragments of these sequences can be utilized to obtain such homologs. In another preferred embodiment, the homolog is selected from the group consisting of alfalfa, apple, *Arabidopsis*, banana, barley, *Brassica, Brassica campestris, Brassica napus*, broccoli, cabbage, canola, castor bean, chrysanthemum, citrus, coconut, coffee, cotton, crambe, cranberry, cucumber, Cuphea, dendrobium, dioscorea, eucalyptus, fescue, fir, garlic, gladiolus, grape, hordeum, lentils, lettuce, liliacea, linseed, maize, millet, muskmelon, mustard, oat, oil palm, oilseed rape, onion, an ornamental plant, papaya, pea, peanut, pepper, perennial ryegrass, *Phaseolus*, pine, poplar, potato, rapeseed (including Canola and High Erucic Acid varieties), rice, rye, safflower, sesame, sorghum, soybean, strawberry, sugarbeet, sugarcane, sunflower, tea, tomato, triticale, turf grasses, and wheat.

In a more preferred embodiment, the homolog is selected from *Brassica campestris, Brassica napus*, canola, castor bean, coconut, cotton, crambe, linseed, maize, mustard, oil palm, peanut, rapeseed (including Canola and High Erucic Acid varieties), rice, safflower, sesame, soybean, sunflower, and wheat, and in a particularly preferred embodiment from coconut, crambe, maize, oil palm, peanut, rapeseed (including Canola and High Erucic Acid varieties), safflower, sesame, soybean, and sunflower.

Agents of the invention include proteins comprising at least about a contiguous 10 amino acid region preferably comprising at least about a contiguous 20 amino acid region, even more preferably comprising at least about a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

Due to the degeneracy of the genetic code, different nucleotide codons may be used to code for a particular amino acid. A host cell often displays a preferred pattern of codon usage. Nucleic acid sequences are preferably constructed to utilize the codon usage pattern of the particular host cell. This generally enhances the expression of the nucleic acid sequence in a transformed host cell. Any of the above described nucleic acid and amino acid sequences may be modified to reflect the preferred codon usage of a host cell or organism in which they are contained. Modification of a nucleic acid sequence for optimal codon usage in plants is described in U.S. Pat. No. 5,689,052. Additional variations in the nucleic acid sequences may encode proteins having equivalent or superior characteristics when compared to the proteins from which they are engineered.

It is understood that certain amino acids may be substituted for other amino acids in a protein or peptide structure (and the nucleic acid sequence that codes for it) without appreciable change or loss of its biological utility or activity. For example, amino acid substitutions may be made without appreciable loss of interactive binding capacity in the antigen-binding regions of antibodies, or binding sites on substrate molecules. The modifications may result in either conservative or non-conservative changes in the amino acid sequence. The amino acid changes may be achieved by changing the codons of the nucleic acid sequence, according to the codons given in Table 1.

TABLE 1

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

In a further aspect of the present invention, nucleic acid molecules of the present invention can comprise sequences that differ from those encoding a protein or fragment thereof selected from the group consisting of SEQ ID NOs: 4 and 48 through 50 due to the fact that the different nucleic acid sequence encodes a protein having one or more conservative amino acid changes.

In a preferred aspect, biologically functional equivalents of the proteins or fragments thereof of the present invention can have about 10 or fewer conservative amino acid changes, more preferably about 7 or fewer conservative amino acid changes, and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Non-conservative changes include additions, deletions, and substitutions that result in an altered amino acid sequence. In a preferred embodiment, the protein has between about 5 and about 500 non-conservative amino acid changes, more preferably between about 10 and about 300 non-conservative amino acid changes, even more preferably between about 25 and about 150 non-conservative amino acid changes, and most preferably between about 5 and about 25 non-conservative amino acid changes or between 1 and about 5 non-conservative changes.

In making such changes, the role of the hydropathic index of amino acids in conferring interactive biological function on a protein may be considered. See Kyte and Doolittle, J. Mol. Biol. 157:105–132 (1982). It is accepted that the relative hydropathic character of amino acids contributes to the secondary structure of the resultant protein, which in turn defines the interaction of the protein with other molecules, e.g., enzymes, substrates, receptors, DNA, antibodies, antigens, etc. It is also understood in the art that the substitution of like amino acids may be made effectively on the basis of hydrophilicity, as the greatest local average hydrophilicity of a protein is known to correlate with a biological property of the protein. U.S. Pat. No. 4,554,101.

Each amino acid has been assigned a hydropathic index and a hydrophilic value, as shown in Table 2.

TABLE 2

Amino Acid Hydropathic Indices and Hydrophilic Values

| Amino acid | Hydropathic Index | Hydrophilic Value |
| --- | --- | --- |
| Alanine | +1.8 | −0.5 |
| Cysteine | +2.5 | −1.0 |
| Aspartic acid | −3.5 | +3.0 ±1 |
| Glutamic acid | −3.5 | +3.0 ±1 |
| Phenylalanine | +2.8 | −2.5 |
| Glycine | −0.4 | 0 |
| Histidine | −3.2 | −0.5 |
| Isoleucine | +4.5 | −1.8 |
| Lysine | −3.9 | +3.0 |
| Leucine | +3.8 | −1.8 |
| Methionine | +1.9 | −1.3 |
| Asparagine | −3.5 | +0.2 |
| Proline | −1.6 | −0.5 ±1 |
| Glutamine | −3.5 | +0.2 |
| Arginine | −4.5 | +3.0 |
| Serine | −0.8 | +0.3 |
| Threonine | −0.7 | −0.4 |
| Valine | +4.2 | −1.5 |
| Tryptophan | −0.9 | −3.4 |
| Tyrosine | −1.3 | −2.3 |

It is known in the art that certain amino acids may be substituted by other amino acids having a similar hydropathic or hydrophilic index, score or value, and still result in a protein with similar biological activity, i.e., still obtain a biologically functional protein. In making such changes, the substitution of amino acids whose hydropathic indices or hydrophilic values are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine.

These amino acid changes may be effected by mutating the nucleic acid sequence coding for the protein or peptide. Mutations to a nucleic acid sequence may be introduced in either a specific or random manner, both of which are well known to those of skill in the art of molecular biology. Mutations may include deletions, insertions, truncations, substitutions, fusions, shuffling of motif sequences, and the like. A myriad of site-directed mutagenesis techniques exist, typically using oligonucleotides to introduce mutations at specific locations in a structural nucleic acid sequence. Examples include single strand rescue, unique site elimination, nick protection, and PCR. Random or non-specific mutations may be generated by chemical agents (for a general review, see Singer and Kusmierek, Ann. Rev. Biochem. 52:655–693, 1982) such as nitrosoguanidine and 2-aminopurine; or by biological methods such as passage through mutator strains (Greener et al., Mol. Biotechnol. 7:189–195, 1997).

C. Recombinant Vectors and Constructs

Exogenous and/or heterologous genetic material may be transferred into a host cell by use of a vector or construct designed for such a purpose. Any of the nucleic acid sequences described above may be provided in a recombinant vector. The vector may be a linear or a closed circular plasmid. The vector system may be a single vector or plasmid or two or more vectors or plasmids that together contain the total DNA to be introduced into the genome of the host. Means for preparing recombinant vectors are well known in the art. Methods for making recombinant vectors particularly suited to plant transformation are described in U.S. Pat. Nos.: 4,971,908, 4,940,835, 4,769,061 and 4,757,011.

Typical vectors useful for expression of nucleic acids in higher plants are well known in the art and include vectors derived from the tumor-inducing (Ti) plasmid of Agrobacterium tumefaciens. Other vector systems suitable for introducing transforming DNA into a host plant cell include, but are not limited to the pCaMVCN transfer control vector, binary artificial chromosome (BIBAC) vectors (Hamilton et al., Gene 200:107–116, 1997), and transfection with RNA viral vectors (Della-Cioppa et al., Ann. N.Y. Acad. Sci. 792: 57–61, 1996). Additional vector systems also include plant selectable YAC vectors such as those described in Mullen et al., Molecular Breeding 4:449–457 (1988).

A construct or vector may include a promoter, e.g., a recombinant vector typically comprises, in a 5' to 3' orientation: a promoter to direct the transcription of a nucleic acid sequence of interest and a nucleic acid sequence of interest. Suitable promoters include, but are not limited to, those described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. For autonomous replication, the vector may further comprise an origin of replication enabling the vector to replicate autonomously in the host cell in question. Alternatively, the vector may be one that, when introduced into the cell, is integrated into the genome and replicated together with the chromosome(s) into which it has been integrated. This integration may be the result of homologous or non-homologous recombination.

Integration of a vector or nucleic acid into the genome by homologous recombination, regardless of the host being considered, relies on the nucleic acid sequence of the vector. Typically, the vector contains nucleic acid sequences for directing integration by homologous recombination into the genome of the host. These nucleic acid sequences enable the vector to be integrated into the host cell genome at a precise location or locations in one or more chromosomes. To increase the likelihood of integration at a precise location, there should be preferably two nucleic acid sequences that individually contain a sufficient number of nucleic acids, preferably about 400 bp to about 1500 bp, more preferably about 800 bp to about 1000 bp, which are highly homologous with the corresponding host cell target sequence. These nucleic acid sequences may be any sequence that is homologous with a host cell target sequence and, furthermore, may or may not encode proteins.

Vectors suitable for replication in mammalian cells may include viral replicons, or sequences that ensure integration of the appropriate sequences encoding HCV epitopes into the host genome. For example, another vector used to express foreign DNA is vaccinia virus. Such heterologous DNA is generally inserted into a gene that is non-essential to the virus, for example, the thymidine kinase gene (tk), which also provides a selectable marker. Expression of the HCV polypeptide then occurs in cells or animals that are infected with the live recombinant vaccinia virus.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, which contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Promoters

Promoters used in the context of the present invention are selected on the basis of the cell type into which the vector will be inserted. Promoters that function in bacteria, yeast, and plants are all taught in the art. The promoters may also be selected on the basis of their regulatory features, e.g., enhancement of transcriptional activity, inducibility, tissue specificity, and developmental stage-specificity. Additional promoters that may be utilized are described, for example, in U.S. Pat. Nos. 5,378,619; 5,391,725; 5,428,147; 5,447,858; 5,608,144; 5,614,399; 5,633,441; 5,633,435; and 4,633,436.

Particularly preferred promoters in the recombinant vector include the nopaline synthase (nos) promoter; mannopine synthase (mas) promoter; octopine synthase (ocs) promoter; the cauliflower mosaic virus (CaMV) 19S and 35S promoters; the enhanced CaMV 35S promoter (eCaMV); the Figwort Mosaic Virus (FMV) 35S promoter; the light-inducible promoter from the small subunit of ribulose-1,5-bisphosphate carboxylase (ssRUBISCO); the EIF-4A promoter from tobacco; corn sucrose synthetase 1; corn alcohol dehydrogenase 1; corn light harvesting complex; corn heat shock protein; the chitinase promoter from *Arabidopsis*; the LTP (Lipid Transfer Protein) promoters from broccoli; petunia chalcone isomerase; bean glycine rich protein 1; potato patatin; the ubiquitin promoter from maize; the Adh promoter; the R gene complex promoter; and the actin promoter from rice.

The promoter is most preferably the nos, ocs, mas, CaMV19S, CaMV35S, eCaMV, ssRUBISCO, FMV, CaMV derived AS4, tobacco RB7, wheat POX1, tobacco EIF-4, lectin protein (Le1), or rice RC2 promoter. The promoter is preferably seed selective, tissue selective, constitutive, or inducible.

Often-used constitutive promoters include the CaMV 35S promoter, the eCaMV 35S promoter, the FMV promoter, the mas promoter, the nos promoter, and the ocs promoter, which is carried on tumor-inducing plasmids of *Agrobacterium tumefaciens*.

Useful inducible promoters include promoters induced by salicylic acid or polyacrylic acids (PR-1), induced by application of safeners (substituted benzenesulfonamide herbicides), heat-shock promoters, a nitrate-inducible promoter derived from the spinach nitrite reductase structural nucleic acid sequence, hormone-inducible promoters, and light-inducible promoters associated with the small subunit of RuBP carboxylase and LHCP families.

For the purposes of expression in specific tissues of the plant, such as the leaf, seed, root or stem, it is preferred that the promoters utilized have relatively high expression in these specific tissues or organs. Examples reported in the literature include the chloroplast glutamine synthetase GS2 promoter from pea, the chloroplast fructose-1,6-biphosphatase (FBPase) promoter from wheat, the nuclear photosynthetic ST-LS 1 promoter from potato, the serine/threonine kinase (PAL) promoter and the glucoamylase (CHS) promoter from *A. thaliana*.

Also reported to be active in photosynthetically active tissues are the ribulose-1,5-bisphosphate carboxylase (RbcS) promoter from eastern larch (*Larix laricina*), the promoters for the cab genes of pine, wheat, spinach, and rice, the pyruvate orthophosphate dikinase (PPDK) promoter from maize, the promoter for the tobacco Lhcb1*2 gene, the *A. thaliana* SUC2 sucrose-H+ symporter promoter and the promoter for the thylakoid membrane proteins from spinach (psaD, psaF, psaE, PC, FNR, atpC, atpD, cab, rbcS). Other promoters for the chlorophyll ab-binding proteins may also be utilized in the invention, such as the promoters for LhcB gene and PsbP gene from white mustard.

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or tuber-enhanced expression are known, including the class I patatin promoter, the promoter for the potato tuber ADPGPP genes, both the large and small subunits, the sucrose synthase promoter, the promoter for the major tuber proteins including the 22 kd protein complexes and protease inhibitors, the promoter for the granule-bound starch synthase gene (GBSS) and other class I and II patatins promoters.

Plant functional promoters useful for preferential expression in seeds include those from plant storage proteins and from proteins involved in fatty acid biosynthesis in oilseeds. Examples of such promoters include the 5' regulatory regions from such genes as napin, phaseolin, zein, soybean trypsin inhibitor, ACP, stearoyl-ACP desaturase, soybean a' subunit of b-conglycinin (soy 7s), and oleosin. Further examples include the promoter for β-conglycinin and the lectin promoter from soybean. Seed-specific regulation is further discussed in EP 255 378.

Also included are promoters for the zeins, which are a group of storage proteins found in maize endosperm. Genomic clones for zein genes have been isolated and the promoters from these clones, including the 15 kD, 16 kD, 19 kD, 22 kD, 27 kD and genes, can also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter.

Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Preferred promoters in rice include promoters for the ADPGPP subunits, the granule bound and other starch synthase, the branching enzymes, the debranching enzymes, sucrose synthases and the glutelins, and particularly preferred is the promoter for rice glutelin, Osgt-1. Preferred promoters for barley include those promoters for the ADPGPP subunits, the granule bound and other starch synthase, the branching enzymes, the debranching enzymes, sucrose synthases, the hordeins, the embryo globulins and the aleurone specific proteins.

Root specific promoters can also be used. An example of such a promoter is the promoter for the acid chitinase gene. Expression in root tissue can also be accomplished by utilizing the root specific subdomains of the CaMV35S promoter that have been identified. Other root cell specific promoters include those reported by Conkling et al. *Plant Physiol.* 93:1203–1211 (1990).

Examples of suitable promoters for use with filamentous fungi are obtained from the genes encoding *Aspergillus oryzae* TAKA amylase, *Rhizomucor miehei* aspartic proteinase, *Aspergillus niger* neutral alpha-amylase, *A. niger* acid stable alpha-amylase, *A. niger* or *A. awamori* glucoamylase (glaA), *Rhizomucor miehei* lipase, *Aspergillus oryzae* alkaline protease, *A. oryzae* triose phosphate isomerase, *Aspergillus nidulans* acetamidase and hybrids thereof. In a yeast host, preferred promoters include the *Saccharomyces cerevisiae* enolase (eno-1), the TAKA amylase, NA2-tpi (a hybrid of the promoters from the genes encoding *A. niger* neutral alpha-amylase and *A. oryzae* triose phosphate isomerase), glaA, *S. cerevisiae* GAL1 (galactokinase) and *S. cerevisiae* GPD (glyceraldehyde-3-phosphate dehydrogenase) promoters.

Suitable promoters for mammalian cells are also known in the art and include viral promoters, such as those from Simian Virus 40 (SV40), Rous sarcoma virus (RSV), adenovirus (ADV), cytomegalovirus (CMV), and bovine papilloma virus (BPV), as well as mammalian cell-derived promoters. Other preferred promoters include the hematopoietic stem cell-specific, e.g., CD34, glucose-6-phosphotase, interleukin-1 alpha, CD11c gene, GM-CSF, interleukin-5R alpha, interleukin-2, c-fos, h-ras, and DMD gene promoters.

Inducible promoters suitable for use with bacteria hosts include the -lactamase and lactose promoter systems, the arabinose promoter system, alkaline phosphatase, a tryptophan (trp) promoter system and hybrid promoters such as the tac promoter. However, other known bacterial inducible promoters are suitable. Promoters for use in bacterial systems also generally contain a Shine-Dalgarno sequence operably linked to the DNA encoding the polypeptide of interest.

Examples of suitable promoters for an algal host are light harvesting protein promoters obtained from photosynthetic organisms, *Chlorella* virus methyltransferase promoters, CaMV 35 S promoter, PL promoter from bacteriophage λ, nopaline synthase promoter from the Ti plasmid of *A. tumefaciens*, and bacterial trp promoter.

Vectors for use with insect cells or insects may utilize a baculovirus transcriptional promoter including, e.g., but not limited to the viral DNAs of *Autographa californica* MNPV, *Bombyx mori* NPV, *Trichoplusia ni* MNPV, *Rachiplusia ou* MNPV or *Galleria mellonella* MNPV, wherein the baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene; or a baculovirus late gene promoter.

Additional Nucleic Acid Sequences of Interest

The recombinant vector may also contain one or more additional nucleic acid sequences of interest. These additional nucleic acid sequences may generally be any sequences suitable for use in a recombinant vector. Such nucleic acid sequences include, without limitation, any of the nucleic acid sequences, and modified forms thereof, described above. The additional nucleic acid sequences may also be operably linked to any of the above described promoters. The one or more additional nucleic acid sequences may each be operably linked to separate promoters. Alternatively, the additional nucleic acid sequences may be operably linked to a single promoter (i.e. a single operon).

The additional nucleic acid sequences include, without limitation, those encoding seed storage proteins, fatty acid pathway enzymes, tocopherol biosynthetic enzymes, amino acid biosynthetic enzymes, and starch branching enzymes. Preferred seed storage proteins include zeins, 7S proteins, brazil nut protein, phenylalanine-free proteins, albumin, β-conglycinin, 11S proteins, alpha-hordothionin, arcelin seed storage proteins, lectins, and glutenin. Preferred fatty acid pathway enzymes include thioesterases and desaturases.

Preferred tocopherol biosynthetic enzymes include tyrA, slr1736, ATPT2, dxs, dxr, GGPPS, HPPD, GMT, MT1, AANT1, slr1737, and an antisense construct for homogentisic acid dioxygenase. Preferred additional nucleic acid sequences encode MEP pathway proteins including ygbB, ygbP, ychB, yfgA, yfgB, dxs and dxr. More preferred nucleic acid sequences include yfgA and yfgB, and still other preferred nucleic acid sequences include ygbB, ychB and ygbP. Preferred amino acid biosynthetic enzymes include anthranilate synthase, tryptophan decarboxylase, threonine decarboxylase, threonine deaminase, and aspartate kinase. Preferred starch branching enzymes include those set forth in U.S. Pat. Nos. 6,232,122 and 6,147,279, and WO 97/22703.

Alternatively, the additional nucleic acid sequence may be designed to down-regulate a specific nucleic acid sequence. This is typically accomplished by operably linking the additional nucleic acid sequence, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs.

Selectable and Screenable Markers

A vector or construct may also include a selectable marker. Selectable markers can also be used to select for plants or plant cells that contain the exogenous genetic material. Examples of such include, but are not limited to: a neo gene, which codes for kanamycin resistance and can be selected for using kanamycin, RptII, G418, hpt etc.; a bar gene, which codes for bialaphos resistance; a mutant EPSP synthase gene, aadA, which encodes glyphosate resistance; a nitrilase gene, which confers resistance to bromoxynil; a mutant acetolactate synthase gene (ALS), which confers imidazolinone or sulphonylurea resistance, ALS, and a methotrexate resistant DHFR gene. The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

A vector or construct can also include a screenable marker. Screenable markers are useful to monitor expression. Exemplary screenable markers include: a β-glucuronidase or uidA gene (GUS), which encodes an enzyme for which various chromogenic substrates are known; an R-locus gene, which encodes a product that regulates the production of anthocyanin pigments (red color) in plant tissues; a β-lactamase gene, which encodes an enzyme for which various chromogenic substrates are known (e.g., PADAC, a chromogenic cephalosporin); a luciferase gene; a xylE gene, which encodes a catechol dioxygenase that can convert chromogenic catechols; an α-amylase gene; a tyrosinase gene, which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins which include a leader sequence such as that found in the expression unit of extension or tobacco PR-S). Other possible selectable and/or screenable marker genes will be apparent to those of skill in the art.

Other Elements in the Recombinant Vector

Various cis-acting untranslated 5' and 3' regulatory sequences may be included in the recombinant nucleic acid vector to produce desirable regulatory features. A vector or construct may also include regulatory elements. Examples of such include the Adh intron 1, the sucrose synthase intron 1 and the TMV omega element. These and other regulatory elements may be included when appropriate, and may be provided by the DNA sequence encoding the gene of interest or a convenient transcription termination region derived from a different gene source.

A 3' non-translated region typically provides a transcriptional termination signal, and a polyadenylation signal that functions in plants to cause the addition of adenylate nucleotides to the 3' end of the mRNA. Such 3' non-translated regions can be obtained from the 3' regions of the nopaline synthase (nos) coding sequence, a soybean 7Sα' storage protein coding sequence, the arcelin-5 coding sequence, the albumin coding sequence, and the pea ssRUBISCO E9 coding sequence. Particularly preferred 3' nucleic acid sequences include Arcelin-5 3', nos 3', E9 3', adr12 3', 7Sα' 3', 11S 3', USP 3', and albumin 3'.

Translational enhancers may also be incorporated as part of the recombinant vector, such as one or more 5' non-translated leader sequences that serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'. Such sequences can be derived from the promoter selected to express the gene or can be specifically modified to increase translation of the mRNA. Such regions can also be obtained from viral RNAs, from suitable eukaryotic genes, or from a synthetic gene sequence. For a review of optimizing expression of transgenes, see Koziel et al., *Plant Mol. Biol.* 32:393–405 (1996).

The recombinant vector can further comprise a nucleic acid sequence encoding a transit peptide. This peptide may be useful for directing a protein to the extracellular space, a plastid, or to some other compartment inside or outside of the cell. (see, e.g., EP 0218571; U.S. Pat. Nos.: 4,940,835, 5,610,041, 5,618,988, and 6,107,060). The nucleic acid sequence in the recombinant vector may comprise introns. The introns may be heterologous with respect to the structural nucleic acid sequence. Preferred introns include the rice actin intron and the corn HSP70 intron.

A protein or fragment thereof encoding nucleic acid molecule of the invention may also be operably linked to a suitable leader sequence. A leader sequence is a nontranslated region of a mRNA that is important for translation by the host. The leader sequence is operably linked to the 5' terminus of the nucleic acid sequence encoding the protein or fragment thereof. A polyadenylation sequence may also be operably linked to the 3' terminus of the nucleic acid sequence of the invention. The polyadenylation sequence is a sequence that when transcribed is recognized by the host to add polyadenosine residues to transcribed mRNA.

A protein or fragment thereof encoding nucleic acid molecule of the invention may also be linked to a propeptide coding region. A propeptide is an amino acid sequence found at the amino terminus of a proprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme.

The recombinant vectors can further comprise one or more sequences that encode one or more factors that are advantageous in the expression of the protein or peptide, for example, an activator (e.g., a trans-acting factor), a chaperone and a processing protease. An activator is a protein that activates transcription of a nucleic acid sequence encoding a polypeptide, a chaperone is a protein that assists another protein in folding properly, and a processing protease is a protease that cleaves a propeptide to generate a mature biochemically active polypeptide. The nucleic acids encoding one or more of these factors are preferably not operably linked to the nucleic acid encoding the protein or fragment thereof.

D. Transgenic Organisms, and Methods for Producing Same

One or more of the nucleic acid molecules or recombinant vectors of the invention may be used in plant transformation or transfection. For example, exogenous genetic material may be transferred into a plant cell and the plant cell regenerated into a whole, fertile or sterile plant. In a preferred embodiment, the exogenous genetic material includes a nucleic acid molecule of the present invention, preferably a nucleic acid molecule encoding a GCPE protein. In another preferred embodiment, the nucleic acid molecule has a sequence selected from the group consisting of SEQ ID NOs: 1 through 3, 5 through 47, complements thereof and fragments of these sequences. Other preferred exogenous genetic material are nucleic acid molecules that encode a protein or fragment thereof having an amino acid sequence selected from the group consisting of SEQ ID NOs: 4, and 48 through 50 or fragments thereof.

The invention is also directed to transgenic plants and transformed host cells that comprise, in a 5' to 3' orientation, a promoter operably linked to a heterologous nucleic acid sequence of interest. Additional nucleic acid sequences may be introduced into the plant or host cell, such as 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above in parts A through C of the Detailed Description. Another embodiment of the invention is directed to a method of producing such transgenic plants which generally comprises the steps of selecting a suitable plant, transforming the plant with a recombinant vector, and obtaining the transformed host cell.

A transformed host cell may generally be any cell which is compatible with the present invention. A transformed host plant or cell can be or derived from a plant, or from a cell or organism such as a mammalian cell, mammal, fish cell, fish, bird cell, bird, algae cell, algae, fungal cell, fungus, or bacterial cell. Preferred host and transformants include: fungal cells such as *Aspergillus,* yeasts, mammals, particularly bovine and porcine, insects, bacteria, and algae. Methods to transform such cells or organisms are known in the art. See, e.g., EP 238023; Becker and Guarente, in: Abelson and Simon (eds.), *Guide to Yeast Genetics and Molecular Biology, Methods Enzymol* 194: 182–187, Academic Press, Inc., New York; Bennett and LaSure (eds.), *More Gene Manipulations in Fungi,* Academic Press, CA, 1991; Hinnen et al., *PNAS* 75:1920, 1978; Ito et al., *J. Bacteriology* 153:163, 1983; Malardier et al., *Gene* 78:147–156, 1989; Yelton et al., *PNAS* 81:1470–1474, 1984.

Transfer of a nucleic acid that encodes a protein can result in expression or overexpression of that protein in a transformed cell, transgenic organism or transgenic plant. One or more of the proteins or fragments thereof encoded by nucleic acid molecules of the invention may be overexpressed in a transformed cell, transgenic organism or transgenic plant. Such expression or overexpression may be the result of transient or stable transfer of the exogenous genetic material.

In a preferred embodiment, expression or overexpression of a GCPE protein in a host provides in that host, relative to an untransformed host with a similar genetic background, an increased level of: (1) tocotrienols; (2) tocopherols; (3) -tocopherols; (4) -tocopherols; (5) isopentenyl diphosphate (IPP); (6) DMAPP; (7) a GCPE protein in a plastid; (8) isoprenoids; (9) carotenoids; (10) an isoprenoid-related compound selected from the group consisting of IPP, DMAPP, and a GCPE protein; or (11) an isoprenoid compound selected from the group consisting of tocotrienols, tocopherols, terpenes, gibberellins, carotenoids, xanthophylls, -tocopherols, -tocopherols, IPP, DMAPP, and a GCPE protein.

The expressed protein may be detected using methods known in the art that are specific for the particular protein or fragment. These detection methods may include the use of specific antibodies, formation of an enzyme product, or disappearance of an enzyme substrate. For example, if the protein has enzymatic activity, an enzyme assay may be used. Alternatively, if polyclonal or monoclonal antibodies specific to the protein are available, immunoassays may be employed using the antibodies to the protein. The techniques of enzyme assay and immunoassay are well known to those skilled in the art.

The resulting protein may be recovered by methods known in the arts. For example, the protein may be recovered from the nutrient medium by procedures including, but not limited to, centrifugation, filtration, extraction, spray-drying, evaporation, or precipitation. The recovered protein may then be further purified by a variety of chromatographic procedures, e.g., ion exchange chromatography, gel filtration chromatography, affinity chromatography, or the like. Reverse-phase high performance liquid chromatography (RP-HPLC), optionally employing hydrophobic RP-HPLC media, e.g., silica gel, further purify the protein. Combinations of methods and means can also be employed to provide a substantially purified recombinant polypeptide or protein.

In another preferred embodiment, overexpression of the GCPE protein in a transgenic plant may provide tolerance to a variety of stresses, e.g., oxidative stress tolerance such as to oxygen or ozone, UV tolerance, heat tolerance, drought tolerance, cold tolerance, or fungal/microbial pathogen tolerance.

As used herein in a preferred aspect, a tolerance or resistance to stress is determined by the ability of a plant, when challenged by a stress such as cold, to produce a plant having a higher yield than one without such tolerance or resistance to stress. In a particularly preferred aspect of the present invention, the tolerance or resistance to stress is measured relative to a plant with a similar genetic background to the tolerant or resistance plant except that the plant expresses or overexpresses a GCPE protein.

Host Cells and Organisms

Preferred host plants and cells can be or be derived from alfalfa, apple, *Arabidopsis,* banana, barley, *Brassica, Brassica campestris, Brassica napus,* broccoli, cabbage, canola, castor bean, chrysanthemum, citrus, coconut, coffee, cotton, crambe, cranberry, cucumber, Cuphea, dendrobium, dioscorea, eucalyptus, fescue, fir, garlic, gladiolus, grape, hordeum, lentils, lettuce, liliacea, linseed, maize, millet, muskmelon, mustard, oat, oil palm, oilseed rape, onion, an ornamental plant, papaya, pea, peanut, pepper, perennial ryegrass, *Phaseolus,* pine, poplar, potato, rapeseed (including Canola and High Erucic Acid varieties), rice, rye, safflower, sesame, sorghum, soybean, strawberry, sugarbeet, sugarcane, sunflower, tea, tomato, triticale, turf grasses, and wheat.

In a more preferred embodiment, the host plants and cells are, or are derived from, *Brassica campestris, Brassica*

*napus,* canola, castor bean, coconut, cotton, crambe, linseed, maize, mustard, oil palm, peanut, rapeseed (including Canola and High Erucic Acid varieties), rice, safflower, sesame, soybean, sunflower, and wheat, and in a particularly preferred embodiment from coconut, crambe, maize, oil palm, peanut, rapeseed (including Canola and High Erucic Acid varieties), safflower, sesame, soybean, and sunflower.

In another preferred embodiment, the plant or cell is or derived from canola. In another preferred embodiment, the plant or cell is or derived from *Brassica napus.* In a particularly preferred embodiment, the plant or cell is or derived from soybean. The soybean cell or plant is preferably a cell or plant of an elite soybean line.

Other preferred plants and plant host cells for use in the methods of the present invention include, but are not limited to Acacia, alfalfa, aneth, apple, apricot, artichoke, arugula, asparagus, avocado, banana, barley, beet, blackberry, blueberry, broccoli, brussel sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, nectarine, oat, oil palm, oilseed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines.

The fungal host cell may, for example, be a yeast cell, a fungi, or a filamentous fungal cell. In one embodiment, the fungal host cell is a yeast cell, and in a preferred embodiment, the yeast host cell is a cell of the species of *Candida, Kluyveromyces, Saccharomyces, Schizosaccharomyces, Pichia* and *Yarrowia.* In another embodiment, the fungal host cell is a filamentous fungal cell, and in a preferred embodiment, the filamentous fungal host cell is a cell of the species of *Acremonium, Aspergillus, Fusarium, Humicola, Myceliophthora, Mucor, Neurospora, Penicillium, Thielavia, Tolypocladium* and *Trichoderma.*

Suitable host bacteria include archaebacteria and eubacteria, especially eubacteria and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus.* Suitable *E. coli* hosts include *E. coli* W3110 (ATCC 27325), *E. coli* 294 (ATCC 31446), *E. coli* B and *E. coli* X1776 (ATCC 31537) (American Type Culture Collection, Manassas, Va.). Mutant cells of any of the above-mentioned bacteria may also be employed. These hosts may be used with bacterial expression vectors such as *E. coli* cloning and expression vector Bluescript™ (Stratagene, La Jolla, Calif.); pIN vectors (Van Heeke and Schuster 1989), and pGEX vectors (Promega, Madison Wis.), which may be used to express foreign polypeptides as fusion proteins with glutathione S-transferase (GST).

Preferred insect host cells are derived from Lepidopteran insects such as *Spodoptera frugiperda* or *Trichoplusia ni.* The preferred *Spodoptera frugiperda* cell line is the cell line Sf9 (ATCC CRL 1711). Other insect cell systems, such as the silkworm *B. mori* can also be used. These host cells are preferably used in combination with Baculovirus expression vectors (BEVs), which are recombinant insect viruses in which the coding sequence for a chosen foreign gene has been inserted behind a baculovirus promoter in place of the viral gene, e.g., polyhedrin (U.S. Pat. No. 4,745,051).

Methods for Introducing Nucleic Acid Molecules into Organisms

Technology for introduction of nucleic acids into cells is well known to those of skill in the art. Common methods include chemical methods, microinjection, electroporation (U.S. Pat. No. 5,384,253), particle acceleration, viral vectors, and receptor-mediated mechanisms. Fungal cells may be transformed by a process involving protoplast formation, transformation of the protoplasts and regeneration of the cell wall. The various techniques for transforming mammalian cells are also well known.

Algal cells may be transformed by a variety of known techniques, including but not limit to, microprojectile bombardment, protoplast fusion, electroporation, microinjection, and vigorous agitation in the presence of glass beads. Suitable procedures for transformation of green algal host cells are described in EP 108580. A suitable method of transforming cells of diatom *Phaeodactylum tricornutum* species is described in WO 97/39106. Chlorophyll C-containing algae may be transformed using the procedures described in U.S. Pat. No. 5,661,017.

Methods for introducing nucleic acids into plants are also well known. Suitable methods include bacterial infection (e.g., *Agrobacterium*), binary bacterial artificial chromosome vectors, direct delivery of nucleic acids (e.g., via PEG-mediated transformation), desiccation/inhibition-mediated nucleic acid uptake, electroporation, agitation with silicon carbide fibers, and acceleration of nucleic acid coated particles, etc. (reviewed in Potrykus et al., *Ann. Rev. Plant Physiol. Plant Mol. Biol.* 42:205, 1991). For example, electroporation has been used to transform maize protoplasts.

Alternatively, nucleic acids can be directly introduced into pollen by directly injecting a plant's reproductive organs. In another transformation technique, nucleic acids may also be injected into immature embryos. Plastids of higher plants can be stably transformed via particle gun delivery of DNA containing a selectable marker and targeting of the DNA to the plastid genome through homologous recombination (U.S. Pat. Nos. 5,451,513 and 5,545,818).

Methods for transforming dicots, primarily by use of *Agrobacterium tumefaciens* and obtaining transgenic plants, have been published for cotton, soybean, *Brassica,* peanut, papaya, pea and *Arabidopsis thaliana.* E.g., U.S. Pat. Nos. 5,004,863, 5,159,135, 5,416,011 5,463,174, 5,518,908, and 5,569,834. The latter method for transforming *Arabidopsis thaliana* is commonly called "dipping" or vacuum infiltration or germplasm transformation. Transformation of monocotyledons using electroporation, particle bombardment and Agrobacterium has also been reported. Transformation and plant regeneration have been achieved in asparagus, barley, maize, oat, orchard grass, rice, rye, sugarcane, tall fescue, and wheat.

Transformation of plant protoplasts can be achieved using methods based on calcium phosphate precipitation, polyethylene glycol treatment, electroporation and combinations of these treatments. Application of these systems to different plant strains depends upon the ability to regenerate that particular plant strain from protoplasts. Illustrative methods for the regeneration of cereals from protoplasts are described in Abdullah et al., *Biotechnology* 4:1087 (1986); Fujimura et al., *Plant Tissue Culture Letters* 2:74 (1985); Toriyama et al., *Theor. Appl. Genet.* 205:34 (1986); and Yamada et al., *Plant Cell Rep.* 4:85 (1986).

To transform plant strains that cannot be successfully regenerated from protoplasts, other ways to introduce DNA into intact cells or tissues can be utilized. For example, cereals may be regenerated from immature embryos or explants. In addition, "particle gun" or high-velocity microprojectile technology can be utilized. Using the latter technology, DNA is carried through the cell wall and into the cytoplasm on the surface of small metal particles. The metal particles penetrate through several layers of cells and thus allow the transformation of cells within tissue explants. A particular advantage of microprojectile bombardment, in addition to it being an effective means of reproducibly transforming monocots, is that neither the isolation of protoplasts (Christou et al., *Plant Physiol.* 87:671–674, 1988), nor the susceptibility to *Agrobacterium* infection is required. See also Yang and Christou (eds.), *Particle Bombardment Technology for Gene Transfer*, Oxford Press, Oxford, England (1994).

An illustrative embodiment of a method for delivering DNA into maize cells by acceleration is a biolistics α-particle delivery system, which can be used to propel tungsten particles coated with DNA through a screen, such as a stainless steel or Nytex screen, onto a filter surface covered with corn cells cultured in suspension. Alternatively, immature embryos or other target cells may be arranged on solid culture medium. The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.).

Through the use of techniques set forth herein, one may obtain about 1000 or more loci of cells transiently expressing a marker gene. The number of cells in a focus which express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Important physical parameters to adjust include physical parameters such as gap distance, flight distance, tissue distance and helium pressure. In addition, biological factors, such as the nature of transforming DNA (e.g., linearized DNA or intact supercoiled plasmids) and the manipulation of cells before and immediately after bombardment, may affect transformation optimization. It is believed that pre-bombardment manipulations are especially important for successful transformation of immature embryos. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation.

*Agrobacterium*-mediated transfer is a widely applicable system for introducing genes into plant cells because the DNA can be introduced into whole plant tissues, thereby bypassing the need for regeneration of an intact plant from a protoplast. Further, the integration of the Ti-DNA is a relatively precise process resulting in few rearrangements. The region of DNA to be transferred is defined by the border sequences and intervening DNA is usually inserted into the plant genome as described (Spielmann et al., 1986).

Modem *Agrobacterium* transformation vectors are capable of replication in *E. coli* as well as *Agrobacterium*, allowing for convenient manipulations. Moreover, technological advances in vectors for *Agrobacterium*-mediated gene transfer have improved the arrangement of genes and restriction sites in the vectors to facilitate construction of vectors capable of expressing various polypeptide coding genes. Available vectors have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i. e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

Transgenic Plants

Regeneration, development, and cultivation of plants from single plant protoplast transformants or various transformed explants is taught in the art, e.g., by Weissbach and Weissbach (eds.), *Methods for Plant Molecular Biology*, Academic Press, Inc., San Diego, Calif. (1988); and Horsch et al., *Science* 227:1229–1231 (1985). There are a variety of methods for the regeneration of plants from plant tissue. The particular method of regeneration will depend on the starting plant tissue and the particular plant species to be regenerated.

Transformants are generally cultured in the presence of a selective media that selects for the successfully transformed cells and induces the regeneration of plant shoots. Such shoots are typically obtained within two to four months. Shoots are then transferred to an appropriate root-inducing medium containing the selective agent and an antibiotic to prevent bacterial growth. Many of the shoots will develop roots, which are then transplanted to soil or other media to allow the continued development of roots. The method, as outlined, will generally vary depending on the particular plant employed.

Preferably, the regenerated transgenic plants are self-pollinated to provide homozygous transgenic plants. Alternatively, pollen obtained from the regenerated transgenic plants may be crossed with seed-grown or non-transgenic plants, preferably plants of agronomically important lines. Conversely, pollen from seed-grown or non-transgenic plants may be used to pollinate the regenerated transgenic plants. A transgenic plant of the invention containing a desired polypeptide is cultivated using methods well-known to one skilled in the art.

A transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

The progeny from these plants are evaluated, among other things, for gene expression. The gene expression may be detected by several common methods such as western blotting, northern blotting, immunoprecipitation, and ELISA. Assays for gene expression based on the transient expression of cloned nucleic acid constructs have been developed by introducing the nucleic acid molecules into plant cells by polyethylene glycol treatment, electroporation, or particle bombardment. Transient expression systems may be used to functionally dissect gene constructs (see generally, Maliga et al., *Methods in Plant Molecular Biology, A Laboratory Course Manual,* Cold Spring Harbor Press, Cold Spring Harbor, N.Y., 1995).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule, for cosuppression of an endogenous protein, or for postranscriptional gene silencing of an endogenous transcript. In addition, the activity of a protein in a plant cell may be reduced or depressed by growing a transgenic plant cell containing a nucleic acid molecule whose non-transcribed strand encodes a protein or fragment thereof.

Cosuppression is the reduction in expression levels, usually at the level of RNA, of a particular endogenous gene or gene family by the expression of a homologous sense construct that is capable of transcribing mRNA of the same strandedness as the transcript of the endogenous gene. Cosuppression may result from stable transformation with a single copy nucleic acid molecule that is homologous to a nucleic acid sequence found with the cell or with multiple copies of a nucleic acid molecule that is homologous to a nucleic acid sequence found with the cell. Genes, even though different, linked to homologous promoters may result in the cosuppression of the linked genes.

Posttranscriptional gene silencing (PTGS) can result in virus immunity or gene silencing in plants. PTGS is induced by dsRNA and is mediated by an RNA-dependent RNA polymerase, present in the cytoplasm, that requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNA-RNAse molecules hybridize to the endogene mRNA and cleave the single-stranded RNA adjacent to the hybrid. The cleaved single-stranded RNAs are further degraded by other host RNases because one will lack a capped 5' end and the other will lack a poly(A) tail. See Waterhouse et al., *PNAS* 95: 13959–13964 (1998).

Antisense approaches are a way of preventing or reducing gene function by targeting the genetic material. The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes.

Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression. An antisense vector can be constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

Feed, Meal, Protein and Oil Preparations

Plants or agents of the present invention can be utilized in methods, for example without limitation, to obtain a seed that expresses a gcpE nucleic acid molecule in that seed, to obtain a seed enhanced in a product of a gcpE gene, to obtain meal enhanced in a product of a gcpE gene, to obtain feedstock enhanced in a product of a gcpE gene, and to obtain oil enhanced in a product of a gcpE gene.

The present invention also provides for parts of the plants, particularly reproductive or storage parts, of the present invention. Plant parts, without limitation, include seed, endosperm, mesocarp, ovule and pollen. In a particularly preferred embodiment of the present invention, the plant part is a seed. In one embodiment the seed is a constituent of animal feed. In another embodiment, the plant part is a fruit, more preferably a fruit with enhanced shelf life. In another preferred embodiment, the fruit has increased levels of a tocopherol.

Plants utilized in such methods may be processed. A plant or plant part may be separated or isolated from other plant parts. A preferred plant part for this purpose is a seed. It is understood that even after separation or isolation from other plant parts, the isolated or separated plant part may be contaminated with other plant parts. In a preferred aspect, the separated plant part is greater than about 50% (w/w) of the separated material, more preferably, greater than about 75% (w/w) of the separated material, and even more preferably greater than about 90% (w/w) of the separated material. Plants or plant parts of the present invention generated by such methods may be processed into products using known techniques.

Preferred products are meal, feedstock and oil. Methods to produce feed, meal, protein and oil preparations are known in the art. See, e.g. U.S. Pat. Nos. 4,957,748, 5,100, 679, 5,219,596, 5,936,069, 6,005,076, 6,146,669, and 6,156, 227. In a preferred embodiment, the protein preparation is a high protein preparation. Such a high protein preparation preferably has a protein content of greater than about 5% w/v, more preferably about 10% w/v, and even more preferably about 15% w/v.

In a preferred embodiment, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than about 1, 5, 10 or 50 liters. The present invention provides for oil produced from plants of the present invention or generated by a method of the present invention. Such oil may be a minor or major component of any resultant product. Moreover, such oil may be blended with other oils.

In a preferred embodiment, the oil produced from plants of the present invention or generated by a method of the present invention constitutes greater than about 0.5%, 1%, 5%, 10%, 25%, 50%, 75% or 90% by volume or weight of the oil component of any product. In another embodiment, the oil preparation may be blended and can constitute greater than about 10%, 25%, 35%, 50% or 75% of the blend by volume. Oil produced from a plant of the present invention can be admixed with one or more organic solvents or petroleum distillates.

Seed Containers

Seeds of the plants may be placed in a container. As used herein, a container is any object capable of holding such seeds. A container preferably contains greater than about 500, 1,000, 5,000, or 25,000 seeds where at least about 10% 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

E. Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 4, 48, 49 and 50, or an amino acid sequence encoded by a nucleic acid sequence selected from the group consisting of SEQ ID NOs: 1 through 3 and 5 through 47. Such antibodies may be used to quantitatively or qualitatively detect the protein or peptide molecules of the invention.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials that describe specific conditions and procedures for the construction, manipulation and isolation of antibodies (see, e.g., Harlow and Lane, in: *Antibodies: A Laboratory Manual*, Cold Spring Harbor Press, Cold Spring Harbor, N.Y., 1988).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Antibodies have been expressed in plants. Cytoplasmic expression of a scFv (single-chain Fv antibody) has been reported to delay infection by artichoke mottled crinkle virus. Transgenic plants that express antibodies directed against endogenous proteins may exhibit a physiological effect. For example, expressed anti-abscisic antibodies have been reported to result in a general perturbation of seed development. See, e.g., Hiatt et al., *Nature* 342:76–78 (1989); Conrad and Fielder, *Plant Mol. Biol.* 26:1023–1030 (1994); Philips et al., *EMBO J.* 16:4489–4496 (1997); Marion-Poll, *Trends in Plant Science* 2:447–448 (1997).

Antibodies that are catalytic may also be expressed in plants (abzymes). The principle behind abzymes is that because antibodies may be raised against many molecules, this recognition ability can be directed toward generating antibodies that bind transition states to force a chemical reaction forward. Persidas, *Nature Biotechnology* 15:1313–1315 (1997); Baca et al., *Ann. Rev. Biophys. Biomol. Struct.* 26:461–493 (1997). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559, 538; 5,576,174; 5,500,358; 5,318,897; 5,298,409; 5,258, 289; and 5,194,585. It is understood that any of the antibodies of the invention may be expressed in plants and that such expression can result in a physiological effect. It is also understood that any of the expressed antibodies may be catalytic.

F. Markers

Another subset of the nucleic acid molecules of the invention includes nucleic acid molecules that are markers. The markers can be used in a number of ways in the field of molecular genetics. Such markers include nucleic acid molecules SEQ ID NOs: 1 through 3 and 5 through 47 or complements thereof or fragments of either that can act as markers and other nucleic acid molecules of the present invention that can act as markers.

Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution. A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" (VNTR) polymorphisms. VNTRs have been used in identity analysis (EP 370719; U.S. Pat. Nos. 5,075,217 and 5,175,082; WO 91/14003).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed. Alternatively, marker nucleic acid molecules comprising a nucleotide sequence of a polynucleotide located within 25 cM of the polymorphism(s) and more preferably within 15 cM of the polymorphism(s) and most preferably within 5 cM of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" (RFLPs) (UK Patent Application 2135774; WO 90/13668; WO 90/11369).

Polymorphisms can also be identified by Single Strand Conformation Polymorphism (SSCP) analysis, random amplified polymorphic DNA (RAPD), and cleaveable amplified polymorphic sequences (CAPS). See, e.g., Lee et al., Anal. Biochem. 205:289–293 (1992); Sarkar et al., Genomics 13:441–443 (1992); Williams et al., Nucl. Acids Res. 18:6531–6535 (1990); and Lyamichev et al., Science 260:778–783 (1993). It is understood that one or more of the nucleic acids of the invention, may be utilized as markers or probes to detect polymorphisms by SSCP, RAPD or CAPS analysis.

Polymorphisms may also be found using a DNA fingerprinting technique called amplified fragment length polymorphism (AFLP), which is based on the selective PCR amplification of restriction fragments from a total digest of genomic DNA to profile that DNA. Vos et al., Nucleic Acids Res. 23:4407–4414 (1995). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes, enzymatic and chemical mismatch assays, allele-specific PCR, ligase chain reaction, single-strand conformation polymorphism analysis, single base primer extension (U.S. Pat. Nos. 6,004,744 and 5,888,819), solid-phase ELISA-based oligonucleotide ligation assays, dideoxy fingerprinting, oligonucleotide fluorescence-quenching assays, 5'-nuclease allele-specific hybridization TaqMan™ assay, template-directed dye-terminator incorporation (TDI) assay (Chen and Kwok, Nucl. Acids Res. 25:347–353, 1997), allele-specific molecular beacon assay (Tyagi et al., Nature Biotech. 16: 49–53, 1998), PinPoint assay (Haff and Smirnov, Genome Res. 7: 378–388, 1997), dCAPS analysis (Neff et al., *Plant J.* 14:387–392, 1998), pyrosequencing (Ronaghi et al., *Analytical Biochemistry* 267:65–71, 1999; WO 98/13523; WO 98/28440; and www.pyrosequencing.com), using mass spectrometry, e.g. the Masscode™ system (WO 99/05319; WO 98/26095; WO 98/12355; WO 97/33000; WO 97/27331; www.rapigene.com; and U.S. Pat. No. 5,965,363), invasive cleavage of oligonucleotide probes, and using high density oligonucleotide arrays (Hacia et al., *Nature Genetics* 22:164–167; www.affymetrix.com).

Polymorphisms may also be detected using allele-specific oligonucleotides (ASO), which, can be for example, used in combination with hybridization based technology including Southern, northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide, and temperature. These factors are important both during the hybridization itself and during subsequent washes performed to remove target polynucleotide that is not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m = 81.5 + 16.6 \times (\log 10[Na+]) + 0.41 \times (\% \text{ G+C}) - 675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele. While certain methods for detecting polymorphisms are described herein, other detection methodologies may be utilized.

The present invention includes and provides a method for detecting a polymorphism in a plant whose presence is predictive of a mutation affecting a level or pattern of a protein comprising: (A) incubating under conditions permitting nucleic acid hybridization: (i) a marker nucleic acid molecule having a nucleic acid sequence that hybridizes to a sequence selected from the group consisting of SEQ ID NOs: 1 through 3, 5 through 47, and complements thereof, and (ii) a complementary nucleic acid molecule obtained from a sample, wherein nucleic acid hybridization between the marker nucleic acid molecule and the complementary nucleic acid molecule permits the detection of a polymorphism; (B) permitting hybridization between the marker nucleic acid molecule and the complementary nucleic acid molecule; and (C) detecting the presence of the polymorphism, wherein the detection of the polymorphism is predictive of the mutation.

The present invention includes and provides a method of determining a degree of association between a polymorphism and a plant trait comprising: (A) hybridizing a nucleic acid molecule specific for the polymorphism to genetic material of a plant, wherein the nucleic acid molecule has a sequence selected from the group consisting of SEQ ID NOs: 1 through 3, 5 through 47, complements thereof, and fragments of these sequences; and (B) calculating the degree of association between the polymorphism and the plant trait.

The present invention includes and provides a method of isolating a nucleic acid that encodes a protein or fragment thereof comprising: (A) incubating under conditions permitting nucleic acid hybridization: (i) a first nucleic acid molecule comprising a sequence selected from the group consisting of SEQ ID NOs: 1 through 3, 5 through 47, complements thereof, and fragments of these sequences; and (ii) a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

G. Plant Breeding

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g., Fehr, *Principles of Cultivar Development*, Vol. 1 (1987).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar because the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, e.g., U.S. Pat. No. 5,811,636.

Requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185–199 (1989), and the interval mapping model, based on maximum likelihood methods described by Lander and Botstein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, 1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, supra, and further described by Arús and Moreno-González, Plant Breeding, (Hayward et al., eds.) Chapman & Hall, London, pp. 314–331 (1993).

In a preferred embodiment of the present invention the nucleic acid marker exhibits a LOD score of greater than about 2.0, more preferably about 2.5, even more preferably greater than about 3.0 or 4.0 with the trait or phenotype of interest. In a preferred embodiment, the trait of interest is altered tocopherol levels or compositions.

Additional models can be used. Many modifications and alternative approaches to interval mapping have been reported, including the use non-parametric methods. Kruglyak and Lander, *Genetics* 139:1421–1428 (1995). Multiple regression methods or models can be also be used, in which the trait is regressed on a large number of markers. Weber and Wricke, *Advances in Plant Breeding*, Blackwell, Berlin (1994). Procedures may combine interval mapping with regression analysis, whereby the phenotype is regressed onto a single putative QTL at a given marker interval and at the same time onto a number of markers that serve as 'cofactors.' Generally, the use of cofactors reduces the bias and sampling error of the estimated QTL positions, thereby improving the precision and efficiency of QTL mapping. Zeng, *Genetics* 136:1457–1468 (1994). These models can be extended to multi-environment experiments to analyze genotype-environment interactions. Jansen et al., *Theo. Appl. Genet.* 91:33–37 (1995).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed. Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, 1938). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i. e., about <10% recombination), dominant and co-dominant markers evaluated in RIL populations provide more information per individual than either marker type in backcross populations. However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles.

Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *PNAS* 88:9828–9832 (1991). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

H. Determining the Level of Expression Response

In an aspect of the present invention, one or more of the nucleic molecules of the present invention are used to determine the level (i.e., the concentration of mRNA in a sample, etc.) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants.

A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more other techniques for the detection of nucleic acids is that it allows an investigator to determine the precise spatial population. In situ hybridization may be used to measure the steady-state level of RNA accumulation. A number of protocols have been devised for in situ hybridization, each with tissue preparation, hybridization and washing conditions.

In situ hybridization also allows for the localization of proteins within a tissue or cell. It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species. It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages. See, e.g., Barres et al., *Neuron* 5:527–544 (1990); Cassab and Varner, *J. Cell. Biol.* 105:2581–2588 (1987); Harris and Chrispeels, *Plant Physiol.* 56:292–299 (1975); Reid and Pont-Lezica, *Tissue Printing: Tools for the Study of Anatomy, Histochemistry and Gene Expression*, Academic Press, New York, N.Y. (1992); Reid et al., *Plant Physiol.* 93:160–165 (1990); Spruce et al., *Phytochemistry* 26:2901–2903 (1987); Ye et al., *Plant J.* 1:175–183 (1991); Yomo and Taylor, *Planta* 112:35–43 (1973).

A microarray-based method for high-throughput monitoring of gene expression may also be utilized to measure Expression Response. This 'chip'-based approach involves microarrays of nucleic acid molecules as gene-specific hybridization targets to quantitatively measure expression of the corresponding mRNA. Hybridization to a microarray can be used to efficiently analyze the presence and/or amount of a number of nucleotide sequences simultaneously.

Several microarray methods have been described. One method compares the sequences to be analyzed by hybridization to a set of oligonucleotides representing all possible subsequences. A second method hybridizes the sample to an array of oligonucleotide or CDNA molecules. An array consisting of oligonucleotides complementary to subsequences of a target sequence can be used to determine the identity of a target sequence, measure its amount, and detect single nucleotide differences between the target and a reference sequence. Nucleic acid molecule microarrays may also be screened with protein molecules or fragments thereof to determine nucleic acid molecules that specifically bind protein molecules or fragments thereof.

The microarray approach may be used with polypeptide targets (U.S. Pat. Nos. 5,445,934; 5,143,854; 5,079,600; and 4,923,901). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides.

In a preferred embodiment of the present invention microarrays may be prepared that comprise nucleic acid molecules where preferably at least about 10%, preferably at least about 25%, more preferably at least about 50% and even more preferably at least about 75%, 80%, 85%, 90% or 95% of the nucleic acid molecules located on that array are selected from the group of nucleic acid molecules that hybridize under low, moderate or high stringency conditions to one or more nucleic acid molecules having a nucleic acid sequence selected from the group of SEQ ID NO: 1 through 3, 5 through 47, and complements thereof.

In another preferred embodiment of the present invention microarrays may be prepared that comprise nucleic acid molecules where preferably at least about 10%, preferably at least about 25%, more preferably at least about 50% and even more preferably at least about 75%, 80%, 85%, 90% or 95% of the nucleic acid molecules located on that array are selected from the group of nucleic acid molecules having a nucleic acid sequence selected from the group of SEQ ID NO: 1 through 3, 5 through 47, complements thereof, and fragments of these sequences.

In a preferred embodiment of the present invention microarrays may be prepared that comprise nucleic acid molecules where such nucleic acid molecules encode at least one, preferably at least two, more preferably at least three, even more preferably at least four, five or six proteins or fragments thereof selected from the group consisting of gcpE, ygbB, ygbP, ychB, dxs and dxr.

The present invention includes and provides a method for determining a level or pattern of a protein in a plant cell or plant tissue comprising (A) incubating under conditions permitting nucleic acid hybridization: (i) a marker nucleic acid molecule having a nucleic acid sequence that hybridizes to a sequence selected from the group consisting of SEQ ID NOs: 1 through 3, 5 through 47, and complements thereof, and (ii) a complementary nucleic acid molecule obtained from the plant cell or plant tissue, wherein nucleic acid hybridization between the marker nucleic acid molecule and the complementary nucleic acid molecule permits the detection of an mRNA for the protein; (B) permitting hybridization between the marker nucleic acid molecule; and (C) detecting the level or pattern of the complementary nucleic acid, wherein the detection of the complementary nucleic acid is predictive of the level or pattern of the protein in the plant.

The present invention also includes and provides a method for determining a level or pattern of a protein in a plant cell or plant tissue comprising (A) assaying the concentration of the protein in a first sample obtained from the plant cell or plant tissue; (B) assaying the concentration of the protein in a second sample obtained from a reference plant cell or a reference plant tissue with a known level or pattern of the protein; and (C) comparing the assayed concentration of the protein in the first sample to the assayed concentration of the protein in the second sample.

I. Screening Uses

The present invention provides methods and agents that can be used to screen for and isolate genes associated with the MEP pathway. Because the MEP pathway is an essential pathway, disruption of any essential gene in the MEP pathway will result in the death of the cell or organism. While not being limited to any particular biological process, the present invention provides a method and the agents associated with such a method where mutations that result in loss of function of a MEP pathway gene do not result in cell or organism death by providing a second pathway capable of synthesizing IPP and DMAPP. The present invention provides cells and organisms having a second pathway capable of synthesizing IPP and DMAPP.

In a preferred aspect, a cell or organism comprising: (a) a first DNA sequence encoding an enzyme having catalytic activity of mevalonate kinase; (b) a second DNA sequence encoding an enzyme having catalytic activity of 5-phosphomevalonate kinase; (c) a third DNA sequence encoding an enzyme having catalytic activity of 5-diphosphomevalonate-decarboxylase; and (d) a fourth DNA sequence encoding an enzyme having catalytic activity of isopentenyl diphosphate isomerase; wherein at least two of said first, second, third, or fourth DNA sequences have a foreign DNA sequence.

In a preferred aspect, the second pathway capable of synthesizing IPP and DMAPP has at least one, more preferably at least two, even more preferably at least three or four enzymes selected from the group consisting of: mevalonate kinase, 5-phosphomevalonate kinase, 5-diphosphomevalonate decarboxylase and isopentenyl diphosphate isomerase. In a more preferred embodiment, at least two, even more preferably at least three or four of the enzymes selected from the group consisting of: mevalonate kinase, 5-phosphomevalonate kinase, 5-diphosphomevalonate decarboxylase and isopentenyl diphosphate isomerase are encoded by a foreign DNA sequence. Any foreign DNA encoding such enzymes may be utilized such as human 5-phosphomevalonate kinase (Genbank Accession No. H09914).

Any cell or organism that possesses the MEP pathway may be used in this aspect of the invention. By providing a second pathway capable of synthesizing IPP and DMAPP, such cells can be utilized in methods to examine the function of a gene, determine whether a gene is associated with the MEP pathway, and identify a gene associated with the MEP pathway.

The present invention includes and provides a cell comprising: (a) a first DNA sequence encoding an enzyme having catalytic activity of mevalonate kinase; (b) a second DNA sequence encoding an enzyme having catalytic activity of 5-phosphomevalonate kinase; (c) a third DNA sequence encoding an enzyme having catalytic activity of 5-diphosphomevalonate-decarboxylase and (d) a fourth DNA sequence encoding an enzyme having catalytic activity of isopentenyl diphosphate isomerase; wherein at least two of the first, second, third or fourth DNA sequence have a foreign DNA sequence.

The present invention includes and provides a method for examining the function of a gene associated with the MEP pathway, comprising: (a) rendering inoperative the gene in a first cell capable of converting mevalonic acid to isopentenyl diphosphate and dimethylallyl diphosphate; (b) rendering inoperative the gene in a second cell incapable of converting mevalonic acid to isopentenyl diphosphate and dimethylallyl diphosphate; and (c) determining the viability of the first cell and the second cell.

The present invention includes and provides a method for determining whether a gene is associated with the MEP pathway, comprising: (a) rendering inoperative the gene in a first cell capable of converting mevalonic acid to isopentenyl diphosphate and dimethylallyl diphosphate; (b) rendering inoperative the gene in a second cell incapable of converting mevalonic acid to isopentenyl diphosphate and dimethylallyl diphosphate; and (c) determining the viability of the first cell and the second cell.

The present invention includes and provides a method for identifying a gene associated with the MEP pathway, comprising: (a) rendering inoperative the gene in a first cell capable of converting mevalonic acid to isopentenyl diphosphate and dimethylallyl diphosphate; (b) rendering inoperative the gene in a second cell incapable of converting mevalonic acid to isopentenyl diphosphate and dimethylallyl diphosphate; and (c) determining the viability of the first cell and the second cell.

Application of the teachings of the present invention to a specific problem or environment is within the capabilities of one having ordinary skill in the art in light of the teachings contained herein. Examples of the products and processes of the present invention appear in the following examples, which are provided by way of illustration, and are not intended to be limiting of the present invention.

EXAMPLE 1

Isolation and Mutagenesis of the Coding Sequences of the MVA+ Transcription Unit Yeast Diphosphomevalonate Decarboxylase (yPMD, ORF YNR043w, ERG19)

The coding sequence of yPMD is amplified by PCR using genomic DNA using *Saccharomyces cerevisiae* strain FY1679 as template. The reaction mixture of the PCR is prepared in a final volume of 25 µl containing 1 µg of template, 0.5 µM of primers CINCO (SEQ ID NO: 51) and SEIS (SEQ ID NO: 52), 100 µM of each deoxynucleoside triphosphate (dNTPs) and Pfu reaction buffer (20 mM of Tris-HCl adjusted to pH 8.8, 2 mM of $MgSO_4$, 10 mM of KCl, 10 mM of $(NH_4)_2SO_4$, 0.1% of Triton X-100, 100 µg/ml of BSA). The sample is covered with mineral oil, incubated at 96° C. for 3 minutes and cooled to 80° C. Pfu DNA polymerase (1 unit, Stratagene) is added and the reaction mixture is incubated for 30 cycles consisting of 1 minute at 94° C. and 4 minutes 30 sec at 72° C., followed by a final step of 10 minutes at 72° C. The PCR product (1879 bp) is cloned in the Sma I restriction site of plasmid pBluescript SK+.

Nde I and Eco RI restriction sites are introduced, respectively, at the 5' and 3' end of the yPMD coding sequence by PCR, using plasmid DNA as template. The reaction mixture of the PCR is prepared in a final volume of 50 1 containing 200 ng of template, 1 µM of primers MPD-Nde5' (SEQ ID NO: 53) and MPD-Eco3' (SEQ ID NO: 54), 100 µm of dNTs, Pfu reaction buffer and 1.25 units of Pfu DNA polymerase. The sample is denatured for 2 minutes at 94° C. and incubated for 10 cycles consisting of 1 minute at 94° C., 1 minute at 61° C. and 2 minutes 30 sec at 72° C. The PCR product (1207 bp) is cloned in the Sma I restriction site of plasmid pBluescript SK+. Sequencing is performed to ensure that no additional mutation had been introduced during amplification.

Human 5-Phosphomevalonate Kinase (hPMK)

A Hpa I restriction site is introduced at both ends of the coding sequence of the human 5-phosphomevalonate kinase by PCR, using the cDNA clone ym0505.rl from Soares infant brain 1NIB as template. The clone ym0505.rl (I.M.A.G.E. 46897; GenBank accession number H09914) is obtained from Research Genetics, Inc (Huntsville, Ala.). The reaction mixture of the PCR is prepared in a final volume of 50 µl containing 200 ng of template, 1 µM of primers hPMK1 (SEQ ID NO: 55) and hPMK4 (SEQ ID NO: 56), 100 µM of dNTPs, Pfu reaction buffer and 1.25 units of Pfu DNA polymerase. The sample is denatured for 2 minutes at 94° C. and incubated for 10 cycles consisting of 30 sec at 94° C., 40 sec at 65° C. and 1 minute 45 sec at 72° C. The PCR product (601 bp) is cloned in the Sma I restriction site of plasmid pBluescript SK+ and sequenced.

Yeast Mevalonate Kinase (yMVK, ORF YMR208w, ERG12)

The coding sequence of yMVK is amplified by PCR using genomic DNA from *Saccharomyces cerevisiae* strain FY1679 as template. The reaction mixture of the PCR is prepared in a final volume of 25 µl containing 1 g of template, 0.5 µM of primers UNO (SEQ ID NO: 57) and DOS (SEQ ID NO: 58), 100 µM of dNTPs and Pfu reaction buffer. The sample is covered with mineral oil, incubated at 96° C. for 3 minutes and cooled to 80° C. One unit of Pfu DNA polymerase is added and the reaction mixture is incubated for 30 cycles consisting of 1 minute at 94° C. and 4 minutes 30 sec at 72° C., followed by a final step of 10 minutes at 72° C. The PCR product (1744 bp) is cloned in the Sma I restriction site of plasmid pBluescript SK+.

A Hpa I restriction site is introduced at both ends of the yPMK coding sequence by PCR, using plasmid DNA as template. The reaction mixture of the PCR is prepared in a final volume of 50 µl containing 200 ng of template, 1 µM of primers MK-Hpa5' (SEQ ID NO: 59) and MK-Hpa3' (SEQ ID NO: 60), 100 µM of dNTPs, Pfu reaction buffer and 1.25 units of Pfu DNA polymerase. The sample is denatured for 2 minutes at 94° C. and incubated for 10 cycles consisting of 45 sec at 94° C., 45 sec at 57° C. and 2 minutes 50 sec at 72° C. The PCR product (1351 bp) is cloned in the Sma I restriction site of plasmid pBluescript SK+ and sequenced.

Isopentenyl Diphosphate Isomerase from *Escherichia coli* (ecIDI)

The coding sequence of the isopentenyl diphosphate isomerase from *E. coli* is amplified by PCR, using genomic DNA from strain W3110 as template. In this PCR, a Xho I restriction site is introduced at both ends of the coding sequence. The reaction mixture of the PCR is prepared in a final volume of 50 µl containing 200 ng of template, 0.5 µM of primers idi5X (SEQ ID NO: 61) and idi3X (SEQ ID NO: 62), 100 µM of dNTPs and Pfu reaction buffer. The sample is covered with mineral oil, incubated at 96° C. for 3 minutes and cooled to 80° C. Pfu DNA polymerase (1.5 units) is added and the reaction mixture is incubated for 5 cycles consisting of 30 sec at 94° C., 40 sec at 55° C. and 1 minute 45 sec at 72° C. and 25 cycles consisting of 30 sec at 94° C. and 2 minutes 15 sec at 72° C. The PCR product (569 bp) is cloned in the Sma I restriction site of plasmid pBluescript SK+.

EXAMPLE 2

Assembly of the MVA+ Transcription Unit

The transcription unit is assembled in a derivative of the expression vector pBAD-GFPuv (Clonetech, Palo Alto, Calif.; GenBank accession number U62637). This is a high copy number plasmid that belongs to the pMB1/ColE1 incompatibility group. The final transcription unit is composed of four ORFs coding for yPMD, hPMK, yMVK and ecIDI. The coding sequences are preceded by ribosomal binding sites that consist of a Shine-Dalgarno sequence followed by an AT-rich translation spacer of eight bases (optimal distance to the ATG start codon; Makrides, *Microbiol. Rev.* 60:512+ (1996)). The whole construct is under control of the $P_{BAD}$ promoter, which can be induced in the presence of L-(+)-arabinose and repressed in the presence of D-(+)-glucose and absence of L-(+)-arabinose. Lobell and Schleif, *Science* 250:528–532 (1990); Guzman et al., *J. Bacteriol.* 177:4121–4130 (1995).

As a preliminary step, the Nde I restriction site located between pBR322ori and the araC coding region of pBAD-GFPuv (position 4926–4931) is eliminated by site-directed mutagenesis as described (Kunkel et al., *Meth. Enzymology* 154:367–382, 1987), using the oligonucleotide pBAD-mut1 (SEQ ID NO: 63) as mutagenic primer. The mutation is confirmed by restriction analysis and sequencing. The plasmid obtained is named pAB-M0. The GFP coding sequence of pAB-M0 is substituted by the yPMD coding sequence. This sequence was cloned between Nde I and Eco RI restriction sites, taking advantage of the modifications introduced at the ends of the yPMD sequence. The yPMD sequence is the first of the transcription unit.

To clone the other coding sequences, a polylinker is first introduced between EcoRI and Sal I restriction sites. The polylinker is generated by annealing the oligonucleotides pBAD-Link1 (SEQ ID NO: 64) and pBAD-Link2 (SEQ ID NO: 65). It contains the restriction sites PMe I and Sna BI, flanked by cohesive ends of Eco RI and Sal I sites. Sites Pme I, Sna BI and Sal I are preceded by the Shine-Dalgarno consensus sequence "TAAGGAGG". The modified inserts coding for hPMK and yMVK are digested with Hpa I and blunt ligated, respectively, into Pme I and Sna BI restriction sites. The modified insert coding for ecIDI is digested with Xho I and ligated into Sal I restriction site. Insert orientation is confirmed after every step by PCR and sequencing.

The plasmid containing yPMD, hPMK and yMVK is named pAB-M2. The plasmid containing, in addition, ecIDI is named pAB-m3.

EXAMPLE 3

Stable Integration of the MVA$^+$ Transcription Unit into the E. coli Chromosome Transfer of the MVA$^+$ transcription unit to the chromosome from E. coli is achieved with a genetic system based in two elements: the E. coli strain TE2680 (Elliott, J. Bacteriol. 174:245–253, 1992) and a pRS550-derived plasmid (Simons et al., Gene 53:85–96, 1987). Strain TE2680 is a recD (tet') mutant host that allows efficient recombination of a linear (restriction enzyme-cleaved) DNA with homologous sequences present in the chromosome. The new sequence is incorporated as a single copy and is perpetuated through cell division.

The sequence of interest, the MVA$^+$ transcription unit in this case, can be cloned in pRS550 vector, between a functional kanamycin resistance (Kan$^R$) gene and a promoterless version of the lac operon. A similar cassette is present in the recipient host (strain TE2680). interrupting the trp operon. This strain is auxotrophic for tryptophan. In this case, however, a non-functional kanamycin resistance (Kan$^S$) gene and the deleted version of the lac operon are flanking a functional chloramphenicol resistance (Cam$^R$) gene. A double crossover affecting the Kan gene and the deleted version of the lac operon substitutes the sequence of interest for the Cam$^R$ gene in the chromosome. As a consequence of the crossover, the recipient strain, originally Kan$^S$ and Cam$^R$, becomes Kan$^R$ and Cam$^S$.

The MVA$^+$ transcription unit is amplified by PCR using the pAB-M3 plasmid as template and oligonucleotides pBAD-D2 (SEQ ID NO: 66) and pBAD-U3 (SEQ ID NO: 67) as primers. The reaction mixture of the PCR is prepared in a final volume of 50 µl containing 200 ng of template, 1 µM of primers, 200 µM of dNTPs, Pfu reaction buffer and 1.75 units of Pfu DNA polymerase. The sample is denatured for 2 minutes at 94° C. and incubated for 10 cycles consisting of 40 sec at 94° C., 50 sec at 59° C. and 8 minutes 15 sec at 72° C. The amplified sequence (4126 bp) contains the complete promoter, including the regulatory sequences that respond to arabinose and glucose, and the four ORFs that allow conversion of MVA to IPP and DMAPP, but lacks the transcription termination signals that are originally present in the expression cassette.

A polylinker is introduced in the vector pRS550, to allow cloning of the PCR product containing the MVA$^+$ transcription unit. The polylinker is generated by annealing the oligonucleotides pRS-L1 (SEQ ID NO: 68) and pRS-L2 (SEQ ID NO: 69). It contains the restriction sites Pme I, Sma I/SrfI and Not I, flanked by cohesive ends of Bam HI and Eco RI sites. Plasmid pRS2110 is generated by cloning the polylinker between Bam HI and Eco RI restriction sites of vector pRS550. The MVA$^+$ transcription is cloned in the Pme I restriction site of vector pRS2110, with the same orientation than the promoterless lac operon, thus restoring transcription of the lac operon. The plasmid obtained is named pRS-MVA$^+$.

Plasmid pRS-MVA$^+$ are digested with Sal I and Sca I restriction enzymes. This digestion rendered a 3196 bp fragment containing the ampicillin resistance gene and a 13406 bp fragment containing the Kan gene, the MVA$^+$ transcription unit and the deleted version of the lac operon. Strain EcAB3-1 is obtained by transformation of strain TE2680 with the linear plasmid DNA. The presence of the MVA$^+$ transcription unit in the chromosome of this strain is confirmed by PCR. The activity of this transcription unit is confirmed by the appearance of blue colonies in plates containing 5-bromo-4-chloro-3-indolyl β-D-galactopyranoside (Xgal). Strain EcAB3-1 is resistant to kanamycin (25 µg/ml) and tetracycline (6 µg/ml) and sensitive to chloramphenicol (17 µg/ml) and ampicillin (50 µg/ml). The MVA$^+$ transcription unit is transduced to E. coli strain MG1655 using phage P1. The strain obtained is named EcAB4-1.

EXAMPLE 4

Identification and Features of the gcpE Gene from E. coli and a Putative Homolog from Arabidopsis thaliana To identify genes potentially involved in the MEP pathway, a bioinformatic approach is adopted. Because bacterial genes with related functions are often organized in operons, uncharacterized open reading frames (ORFs) that are beside known genes of the MEP pathway are examined. An ORF of 1195 bp with unknown function is found just upstream of a DXS coding sequence of Streptomyces coelicolor (cosmid 6A5, Accession Number AL049485). This ORF is homologous to an essential gene of Escherichia coli named gcpE (Baker et al., FEMS Microbiol. Lett. 94:175–180, 1992 (accession number X64451)). An homolog of this gene, named aarC, is identified in Providencia stuartii and described as an essential gene involved in density-dependent regulation of the 2'-N-acetyltransferase (Rather et al., J. Bacteriol. 179:2267–2273, 1997). However, no precise function was assigned to the aarC gene.

The gcpE gene is broadly distributed in evolution. The occurrence of this gene in completely sequenced genomes strictly correlates with the occurrence of the gene encoding 1-deoxy-D-xylulose 5-phosphate reductoisomerase (dxr), which catalyses the first committed step of the MEP pathway. Fourteen out of 26 sequenced genomes contain both dxr and gcpE. Twelve of these sequenced genomes do not contain dxr nor gcpE. The gcpE gene is also highly conserved in plants. GcpE homologs are found as EST entries in Arabidopsis thaliana (gb T46582, SEQ ID NO: 5), Glycine max (gb AW152929, SEQ ID NO: 6), Lycopersicon esculentum (gb AW040413, SEQ ID NO: 7), Mesembryanthemum crystallinum (gb A1822799, SEQ ID NO: 8), Oryza sativa (gb AA753160, SEQ ID NO: 9), Zea mays (gb AW126434, SEQ ID NO: 10), Pinus taeda (gb AW042702, SEQ ID NO: 11) and Physcomitrella patens (gb AW497432, SEQ ID NO: 12).

A cDNA clone from Arabidopsis coding for a gcpE homolog (EST clone 135H1T7, accession number T46582) is obtained from the Arabidopsis Biological Resource Center (ABRC). This clone encodes a full length protein. The EDNA contains an ORF of 2223 bp that encodes a protein of 740 amino acid residues (SEQ ID NO: 1). The Arabidopsis gcpE gene corresponding to this cDNA is located in chromosome V (genomic P1 clone MUP24, accession number AB005246). This gene contains 20 exons that extend along 4 kb of genomic sequence.

Alignment of the *E. coli* and *Arabidopsis* gcpE proteins shows high similarity but also striking differences. The first 75 amino acid residues of the *Arabidopsis* sequence constitute a region that is not present in the bacterial counterpart. A transit peptide for plastids is predicted at this region with the ChloroP V1.0 program accessible at the Center for Biological Sequences, University of Denmark web site and described by Emanuelsson, et al. (*Protein Science* 8:978–984, (1999)). According to this program, the processing site of the transit peptide would be located between Arg38 and Ser39 (CS-score 2.392). In vivo import experiments to chloroplasts demonstrated that the N-terminal region of the *Arabidopsis* protein is a functional transit peptide for plastids.

The putative mature gcpF protein from *Arabidopsis* is significantly larger than the *E. coli* counterpart (78 versus 41 kDa). Although the two proteins align and show high similarity at the N- and C-terminal regions, the *Arabidopsis* isoform possesses several additional amino acid sequences between these two regions, particularly a domain of 268 amino acid residues (30 kDa) which is only present in the *Arabidopsis* protein (SEQ ID NO: 1).

EXAMPLE 5

Deletion of the gcpE Coding Sequence in the *E. coli* Genome

To confirm whether gcpE from *E. coli* is indeed involved in the MEP pathway, gcpE is deleted in strain EcAB3-1. As mentioned above, mutants of the MEP pathway can be rescued in this strain, in the presence of MVA. Deletion of the gcpE gene is accomplished by homologous recombination using construct GC5CAT3 as the donor cassette. In this construct, the CAT gene is surrounded by the gcpE flanking regions. Substitution of the CAT gene for the gcpE coding sequence in the genome can be selected by chloramphenicol resistance.

Four PCR reactions are necessary to prepare the GC5CAT3 construct. First, a genomic region of 3231 bp, encompassing the gcpE ORF (1116 bp), together with flanking regions, is amplified by PCR, using genomic DNA from strain MC4100 as template. The reaction mixture of the PCR is prepared in a final volume of 50 l containing 250 ng of template, 0.4 M of primers 1PE (SEQ ID NO: 70) and 4PE (SEQ ID NO: 73), 200 M of dNTPs, 1 mM of MgSO$_4$, Pfx reaction buffer and 1.25 units of PLATINUM Pfx DNA polymerase (Life Technologies Inc., Rockville, Md.). The sample is denatured for 2 minutes at 94 C and incubated for 30 cycles consisting of 40 seconds at 94 C, 50 seconds at 67 C and 3 minutes 30 seconds at 68 C.

The regions flanking the gcpE coding sequence are amplified by PCR using the PCR product of primers 1PE and 4PE as template. Primers 1PE (SEQ ID NO: 70) and 22PE (SEQ ID NO: 71) are used to amplify the 5' flanking region. In this PCR, primer 22PE generates a Sma I restriction site. Primers 3PE (SEQ ID NO: 72) and 4PE (SEQ ID NO: 73) are used to amplify the 3' flanking region. In this PCR, primer 3 PE generates a Pme I restriction site. The reaction mixtures of these PCRs are prepared in final volumes of 50 l containing 150 ng of template, 4 M of primers, 200 M of dNTPs, Pfx reaction buffer and 1.25 units of PLATINUM Pfx DNA polymerase. The samples are denatured for 2 minutes at 94 C and incubated for 10 cycles consisting of 40 seconds at 94 C and 2 minutes at 68 C. The PCR product corresponding to the 3' flanking region (1061 bp) is cloned in the Sma I restriction site of plasmid pBluescript SK+. The plasmid obtained is named GC3. Subsequently, the PCR product corresponding to the 5' flanking region (1102 bp) is cloned in the Pme I restriction site of plasmid GC3. The relative orientation of the 3' and 5' flanking regions is the same than that in the *E. coli* genome. The plasmid with the two gcpE flanking regions is named GC53.

The CAT gene is amplified by PCR using the plasmid pCAT19 (Fuqua, 1992) as template and oligonucleotide CAT1 (SEQ ID NO: 74) and CAT4 (SEQ ID NO: 75) as primers. The reaction mixture of the PCR is prepared in a final volume of 50 l containing 100 ng of template, 1 M of primers, 100 M of dNTPs, Pfx reaction buffer and 1.25 units of PLATINUM Pfx DNA polymerase. The sample is denatured for 2 minutes at 94 C and incubated for 20 cycles consisting of 40 seconds at 94 C, 50 seconds at 53 C and 1 minute at 68 C. The PCR product (960 bp) is cloned in the Sma I restriction site of plasmid GC53. The construct obtained is named GC5CAT3. In this construct, the CAT gene has the same orientation than the gcpE gene previously deleted.

Plasmid containing GC5CAT3 construct is digested with HindIII, Xba I and Xho I restriction enzymes to release the recombination cassette. This cassette is amplified by PCR using oligonucleotides 1PE (SEQ ID NO: 70) and 4PE (SEQ ID NO: 73) as primers. The PCR product is used to transform electrocompetent cells of strain EcAB3-1. These cells are plated on 2×TY medium containing 1.5% agar (w/v), 17 g/ml chloramphenicol, 6 g/ml tetracycline, 25 g/ml kanamycin, 0.2% (w/v) L-(+)-arabinose and 1 mM MVA.

The presence of the CAT gene in place of the gcpE coding sequence in the genome of transformants is confirmed by PCR using oligonucleotides 0PE and 5PE as primers. The identity of the PCR product is verified by restriction analysis. Oligonucleotides 0PE (SEQ ID NO: 76) and 5PE (SEQ ID NO: 77) are complementary to genomic sequences located outside of the region included in the recombination construct. Analysis of transformants confirms both the absence of the original gcpE gene and the presence of the CAT gene. The novel strain is named EcAB3-3.

Strain EcAB3-3 can grow only in the presence of MVA. A control strain carrying a disruption of dxs gene (EcAB3-2) is also auxotrophic for MVA.

EXAMPLE 6

Identification of GCPE Function

Example 5 describes the generation of *E. coli* strain with a deletion of the gcpE coding sequence (strain EcAB3-3). In addition to the gcpE deletion the strain also carries a MVA$^+$ transcription unit as described in Examples 1, 2 and 3 which makes it auxotrophic for mevalonic acid or mevalonate (MVA). This strain is used to find out which intermediate accumulates due to the disruption of the gcpE gene. The gcpE deletion disrupts the MEP pathway blocking the formation of IPP and DMAPP, creating the need for exogenous MVA to synthesize IPP and DMAPP.

A culture of the *E. coli* strain with a disrupted gcpE gene is made in the presence of MVA. After growth, the cells are harvested by centrifugation, washed with culture medium containing no MVA and resuspended for 16 hours in a culture medium containing [$^3$H]ME (Methylerythritol). Thin layer chromatography separation of the water/ethanol (30:70) extract of the cells affords a radioactive band co-eluting with methylerythritol cyclodiphosphate (isopropanol/water/ethyl acetate, 60:30:10, $R_f$=0.56). Carrier material is obtained for the latter compound from *Corynebacterium ammoniagenes* treated with benzylviologen. Additional data is collected, suggesting that the radioactive compound might correspond to methylerythritol cyclodiphosphate. On HF hydrolysis, it releases free methylerythritol. Like methylerythritol cyclodiphosphate, it is not affected by alkaline phosphatase, which normally cleaves acyclic diphosphates. This compound is not accumulated by the mva+/dxr–*E. coli* strain with an intact gcpE gene. In the latter experiment [$^3$H]ME is incorporated into ubiquinone and menaquinone, which are not labeled in the gcpE disrupted strain.

Further conformation of function for gcpE will require cell-free assays using radiolabeled methylerythritol cyclodiphosphate as described below.

EXAMPLE 7

GCPE Enzyme Assays
Enzymatic Preparation of [$^{14}$C]methylerythritol 2,4-cyclodiphosphate The substrate methylerythritol cyclodiphosphate cannot be readily chemically synthesized. Attempts to accumulate the tritiated compound from [$^3$H]ME by the mva$^+$/dxr$^-$/gcpE$^-$ mutant described above result in very low yields. Enzymatic synthesis of [$^{14}$C]methylerythritol cyclodiphosphate is thus required. This can be achieved using all the known enzymes of the MEP pathway, viz., dxs, dxr, ygbP, ychB, and ygbB.

Enzymatic syntheses of [$^{14}$C]-deoxy-D-xylulose-5-phosphate (DXP) and MEP from [$^{14}$C]pyruvate isotopomers and D-glyceraldehyde-3-phosphate (GAP) are performed using *E. coli* strains overexpressing dxs and dxr genes. In order to prepare the subsequent [$^{14}$C]methylerythritol cyclodiphosphate from the [$^{14}$C]MEP the following scheme is used.

Three *E. coli* strains are generated with each one overexpressing one of the three remaining genes in the MEP pathway, viz., ygbP (pQE31-ygbP, pREP4), ychB (pQE30-ychB, pREP4) and ygbB (pQE30-ygbB, pREP4). Each strain is grown on LB medium containing ampicillin and kanamycin at 37° C. overnight. Each culture (2 ml) is used to inoculate the same medium (50 mL), which are then grown for 3 hours until a 0.5 OD (600 nm) is reached, then induced using IPTG (final concentration 0. 1 mM) for 4.5 hours. After centrifugation, the cells of each culture are resuspended in 100 mM Tris-HCl (3 mL, pH 8) and disrupted by sonication (3×30 s with 1 min cooling) at 0° C. After centrifugation, the supernatant is stirred for 1 hour at 0° C. in the presence of a 50% Ni-NTA slurry (1 mL, Qiagen Inc., Valencia, Calif.).

The lysate-Ni-NTA mixture is loaded onto a column and the flow-through is collected. The column is washed twice with 100 mM Tris-HCl (4 mL, pH8) containing 50 mM imidazole. The proteins are eluted with 100 mM Tris-HCl (2 mL, pH 8) containing 200 mM imidazole. Additional 100 mM Tris-HCl (1.5 mL, pH 8) is added to each protein, and the resulting solution is dialyzed against 100 mM Tris-HCl (pH 8) containing 20% glycerol. On a 12% SDS-PAGE gel, the 6×His-tagged MEP cytidylyl transferase (ygbP), CDP-ME kinase (ychB) and 2-C-methyl-D-erythritol 2,4-cyclodiphosphate synthase (ygbB) are separated from other cellular components.

Using these pure proteins, [$^{14}$C]2-C-methyl-D-erythritol 2,4-cyclodiphosphate is prepared in a one-pot procedure. In a typical incubation, [$^{14}$C]MEP (10 µL, 2.27×10$^6$ cpm, 15.8 µCi/µmol) is incubated with the purified MEP cytidylyl transferase (100 µL, 0.4 mg/mL), 6×His-tagged CDP-ME kinase (200 µL, 0.15 mg/mL) and 2-C-methyl-D-erythritol 2,4-cyclodiphosphate synthase (200 µL, 0.6 mg/mL) solutions in 100 mM Tris-HCl (1 mL, pH 8) containing 5 mM CTP, 1 mM ATP, 5 mM MnCl$_2$ and 5 mM MgCl$_2$. The incubation is performed at 37° C. for 10 hours.

An aliquot (3 µL) is analyzed on a silica gel plate eluted with isopropanol/water/ethyl acetate (6:3:1). Radioactivity is monitored with a PhosphoImager. A single radioactive compound is detected. It coelutes with unlabeled 2-C-methyl-D-erythritol 2,4-cyclodiphosphate. No radioactivity is found comigrating with ME-CDP. An aliquot is incubated in the presence of alkaline phosphatase and no [$^{14}$C] methyerythritol is detected, indicating that no [$^{14}$C]MEP remained in the incubation mixture.

GCPE Enzyme Test

When purified His-tagged GCPE is assayed with the [$^{14}$C] 2-C-methyl-D-erythritol 2,4-cyclodiphosphate as prepared above there is no reaction product detected. One reason for lack of activity could be that GCPE needs other proteins to form a complex with diverting 2-C-methyl-D-erythritol 2,4-cyclodiphosphate into the two branches of the MEP pathway. Because of the genetic link of yfgB and yfgA with gcpE (all three are on the same operon of the *E. coli* genome), it is possible that these proteins could be part of this hypothetical enzyme complex. Thus, an expression plasmid containing the genomic region covering yfgB, yfgA and gcpE is constructed and stably transformed into *E. coli* creating the strain BL21(DE3)pLys[PET-T7-gcpE-yfgA-yfgB]. This strain and the BL21(DE3)pLys[PET-T7] and BL21(DE3) pLys[PET-T7-yfgA-yfgB] or [MVA$^+$,gcpE$^-$PQE30-AT-gcpE] strains are grown and induced with 1PTG using standard conditions.

In a typical experiment, the *E. coli* strain BL21(DE3)pLys [PET-T7-gcpE-yfgA-yfgB] is grown at 30° C. in LB medium (50 mL) containing chloramphenicol (34 µg/mL) and ampicillin (100 mg/mL) until reaching a 0.65 OD (600 nm). Induction is then performed with IPTG (0.5 mM) for 6 hours. The cells are harvested by centrifugation (7000 g, 10 min) resuspended in buffer (4 mL, 50 mM Tris Hcl pH=8, 1 mM PMSF, 1 mM DTT, 5 mM MgCl$_2$) and broken at 0° C. by sonication (2×30 s, with 1 min cooling). The cell debris is removed by centrifugation (16000 g, 10 min).

The resulting crude cell-free material (130 µL) is completed with buffer (20 µL) and used for the enzyme assays at 37° C. for 7 hours and 20 hours with the [$^{14}$C]2-C-methyl-D-erythritol 2,4-cyclodiphosphate solution (50 µL) obtained as described above. Controls consist in the same mixture, but the enzyme preparation is replaced by buffer. After incubation, an aliquot (9 µl) of each assay is analyzed on a silica plate eluted with isopropanol/water/ethyl acetate (6:3:1). Radioactivity is monitored with a PhosphoImager.

For unknown reasons, only the assay with *E. coli* BL21 (DE3)pLys[PET-T7-gcpE-yfgA-yfgB] extract is successful. In all assays performed with enzyme preparations from other strains, the entire radioactivity comigrated with unlabeled 2-C-methyl-D-erythritol 2,4-cyclodiphosphate, indicating that no reaction occurred. The TLC migration profile is the same as that observed for the control without enzyme.

In the case of all assays performed with the cell system prepared from the BL21(DE3)pLys[PET-T7-gcpE-yfgA-yfgB] strain, there is decrease of the substrate concentration and the accumulation of a new compound. According to its TLC behavior ($R_f$=0.85, isopropanol/water/ethyl acetate, 60:30:10), this compound corresponds to a non-phosphorylated derivative. Such a dephosphorylation is most likely, as the test is performed with a crude cell-free system containing probably phosphatases, and as no phosphatase inhibitor was added to the incubation buffer. Dephosphorylation of the reaction product might favor displacement of the reaction, the full consumption of the substrate and finally accumulation of a single major product.

The same compound is obtained when only $MgCl_2$ was present in the assay, suggesting that the cofactors tested are not necessary. It is possible that the fact the product is dephosphorylated in situ helped to its accumulation. The dephosphorylated new compound ($R_f$=0.56, $CHCl_3$/$CH_3OH$, 8:2) is characterized by a $R_f$ between those of methylerythritol ($R_f$=0.22) and isopentenol ($R_f$=0.56). TLC comparison with unlabeled synthetic carriers indicates that compounds 1 to 9 (shown in FIG. 1) do not correspond to the non-phosphorylated new compound.

To fully characterize the dephosphorylated product, a larger-scale incubation (10x) is performed and the residue is acetylated (pyridine/$Ac_2O$, 10 ml) overnight. After the removal of the reagents, the residue is resuspended in $CHCl_3$ (12 ml) and the resulting precipitate is removed by filtration. The filtrate is concentrated to dryness (836000 cpm, 1.1 g) and purified on a silica column (8 g) eluted with hexane/ethyl acetate (3:1) and fractions of 5 ml are collected. An aliquot (4 µl) of each fraction is spotted on TLC plates (hexane/ethyl acetate, 3:1) and the radioactivity monitored by PhosphoImager. The radioactive fractions of same $R_f$ are pooled together.

Three radioactive products can be detected: Fraction A (200 mg) contains the acetate of the dephosphorylated new compound ($R_f$=0.4), fraction B (20 mg) contains the 2-C-methyl-D-erythritol triacetate ($R_f$=0.2), and fraction C (100 mg) contains another new compound ($R_f$=0.25) which is not yet identified. Fraction A is further purified on a silica column (9 g) eluted first with $CH_2Cl_2$ in order to remove almost all impurities and then with ethyl acetate in order to recover the radioactive product. As previously described, an aliquot (4 µl) of each 2 ml fraction is checked for radioactivity and the radioactive fractions are pooled together, concentrated to dryness and almost pure acetate of the dephosphorylated new compound (1 mg) is obtained.

Figure 2:
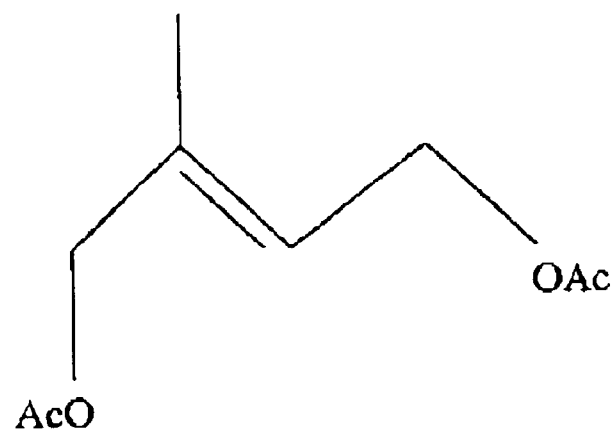
FIG. 2 sets forth the diacetate of 2-methylbut-2-ene-1,4-diol.
Figure 3:
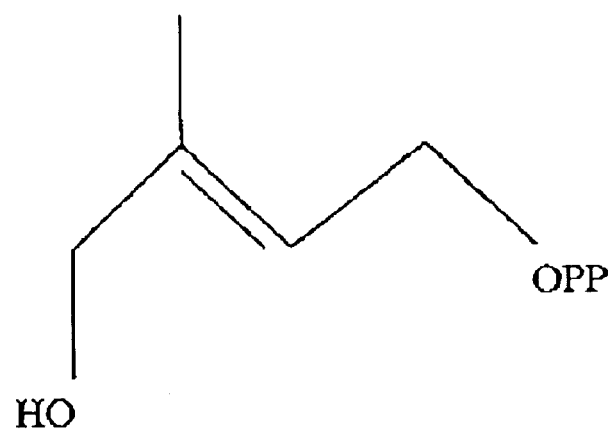
FIG. 3 sets forth (E)-1-(4-hydroxy-3-methylbut-2-enyl) diphosphate.

This compound is analyzed by $^1$H-NMR and from the resulting spectrum it is concluded that the acetate of the putative dephosphorylated GCPE product could be diacetate of (E)-2-methylbut-2-ene-1,4-diol. The spectrum is compared with a reference synthetic diacetate of (E)-2-methylbut-2-ene-1,4-diol synthesized by $LiAlH_4$ reduction of methylfumaric acid as previously described for the reduction of 3-methylfuran-2(5H)-one or citraconic anhydride (Duvold et al., *Tetrahedron Letters* 38: 6181–6184, 1997). All signals of the enzymatic product match the corresponding signals in the synthetic standard. Furthermore the coelution of the enzymatic radioactive product and the synthetic diacetate of (E)-2-methylbut-2-ene-1,4-diol is observed ($CH_2Cl_2$, Rf=0.25). Therefore, one product of the incubation is identified as diacetate of (E)-2-methylbut-2-ene-1,4-diol (FIG. 2). This positive identification suggests that the product of GCPE reaction with 2-C-methyl-D-erythritol 2,4-cyclodiphosphate is (E)-1-(4-hydroxy-3-methylbut-2-enyl) diphosphate (FIG. 3).

EXAMPLE 8

Characterization of *Arabidopsis* GCPE

Upon identification of the *Escherichia coli* gcpE gene as involved in the trunk line of the MEP pathway for isoprenoid biosynthesis, the available databases are searched for plant homologs. As described in Example 4, clone 135H1 (Genbank accession number T46582) is identified as containing an *Arabidopsis thaliana* cDNA encoding a protein with homology to the product of the bacterial gcpE gene. As shown in FIG. 4, however, the putative *Arabidopsis* GCPS protein (SEQ ID NO: 79), contains several domain that are absent from the *E. coil* protein (SEQ ID NO: 78). Identical residues are in black boxes and conservative changes in grey boxes. Gaps are indicated with dots. The predicted cleavage site for the plastidial targeting peptide (according to the ChloroP program, accessible at the Center for Biological Sequences, University of Denmark web site and described by Emanuelsson, et al. (*Protein Science* 8:978–984, (1999)) is indicated with an arrow (see FIG. 4).

To determine whether the *Arabidopsis* protein encoded by clone 135H1 is indeed a GCPE protein, a complementation assay is carried out using the *E. coli* strain EcAB3-3. In this strain, which is engineered to synthesize IPP and DMAPP from mevalonic acid (MVA), the chromosomal gcpE gene is disrupted by insertion of the CAT marker conferring chloramphenicol resistance. Because the disruption of gcpE is lethal, mutant EcAB3-3 cells require MVA for growth (see Example 5).

For the complementation assay, plasmid pQE-AGH is created by subcloning a BglII-SphI fragment (coding sequence SEQ ID NO: 80 and deduced amino acid sequence SEQ ID NO: 81) from clone 135H1 into the BamHI-SphI sites of the pQE30 expression vector (coding sequence SEQ ID NO: 82 and deduced amino acid sequence SEQ ID NO: 83) (Qiagen) (FIG. 5). The resulting construct encodes a His-tagged protein (coding sequence SEQ ID NO: 84 and deduced amino acid sequence SEQ ID NO: 85) lacking the N-terminal sequence predicted to be a plastidial targeting peptide with the ChloroP program (FIG. 5). Expression from plasmid pQE-AGH is under the control of the IPTG-inducible T5 promoter. FIG. 5 depicts the coding sequences in uppercase, and the deduced amino acid sequences are shown below the respective coding sequences. The predicted cleavage site for the plastidial targeting peptide is indicated with an arrow.

EcAB3-3 cells are transformed with plasmid pQE-AGH and plated on LB plates containing 100 mg/l kanamycin (to select for the MVA operon), 34 mg/l chloramphenicol (to select for the gcpE gene disruption), 100 mg/l ampicillin (to select for transformants containing pQE-AGH), 0.04% arabinose (to induce expression of the MVA operon genes), and 0.5 mM MVA (to be used for IPP and DMAPP biosynthesis). The resulting strain, EcAB3-3(pQE-AGH), is able to grow in absence of MVA at 30° C. and 37° C., confirming that MVA auxotrophy can be overcome by the presence of plasmid pQE-AGH. These results demonstrate that the cloned *Arabidopsis* cDNA encodes a protein with the same activity as the *E. coli* GCPE protein.

In order to study whether the truncated *Arabidosis* GCPE protein cloned in plasmid pQE-AGH is active in converting ME-cPP to the next intermediate of the MEP pathway, the protein is expressed at high levels in *E. coli*. Strains XL1Blue or M15 (Qiagen Inc., Valencia, Calif.) are used for expression under several experimental conditions: growth at 23° C., 30° C., or 37° C. and induction with 1 or 0.4 mM IPTG, with unsuccessful results. When strain EcAB3-3 (pQE-AGH) is used, however, expression of the cloned protein is detected.

An overnight culture of EcAB3-3(pQE-AGH) cells grown in LB medium supplemented with kanamycin, chloramphenicol, ampicillin, arabinose and with or without MVA at the concentrations described above is diluted 1:50 in fresh medium and incubated at 37° C. until reaching an $OD_{600}$ of ca. 0.3. Although cells grew better when MVA is added to the medium, the presence of plasmid pQE-AGH is sufficient to allow growth in the absence of any exogenous source for isoprenoid synthesis. Expression of the truncated *Arabidopsis* GCPE protein is induced by adding IPTG to a final concentration of 0.4 mM.

After incubation at 30° C. for 4 hours, cells are collected by centrifugation and resuspended in a 1/50 volume of homogeneization buffer (Tris-HCl 20 mM pH 8.0, 1 mM β-mercatoethanol, 1 mg/ml lysozyme, 80 mg/l PMSF, and 1 tablet/20 ml of Complete Mini, EDTA-free Protease Inhibitor Cocktail Tablets (Roche Molecular Biosystems, Indianapolis, Ind.)). Following incubation at room temperature for 20 minutes, cells are sonicated 5 times for 30 seconds at 30W. The insoluble fraction is pelleted by centrifugation at 5000×g for 30 minutes and the supernatant (soluble fraction) is collected. Electrophoresis on SDS-PAGE of an aliquot of this soluble fraction shows that a protein of the expected size (ca. 78 kD) is expressed in cells grown with or without MVA.

Purification of the His-tagged protein from the soluble extract is carried out using HiTrap columns (Pharmacia, Uppsala, Sweden). Flux through the column is kept constant at 2.5 ml/min during all the steps. After applying the sample to a column and washing unbound proteins with 20 ml of washing buffer (20 mM Tris-HCl pH 8.0, 10 mM imidazole, 500 mM NaCl), elution is performed with 50 ml of a gradient solution containing from 10 mM to 500 mM imidazole and 2.5 ml fractions are collected afterwards. The truncated *Arabidopsis* GCPE protein elutes at 100 mM imidazole and is virtually pure.

EXAMPLE 9

Preparation of plant Expression Vectors with GCPE

Rice, soybean and *E. coli* gcpE genes are chosen for plant expression. An *E. coli* gene (SEQ ID NO: 3) is cleaved by NcoI/EcoRI restriction digest, gel purified, and ligated into NcoI/EcoRI-digested and gel purified pMON26541 resulting in the formation of a shuttle vector. These ligations fuse the bacterial gcpE gene to CTP1, which is the chloroplast target peptide of the small subunit of the ribulose bisphosphate carboxylase from *Arabidopsis,* and place it under e35S promoter control.

To place the gcpE gene under napin promoter control, the shuttle vector is digested with EcoRI, ends are filled in using the Klenow fragment, and the gel purified vector is digested with Bgl II. The smaller fragment encoding the gcpE gene fused to CTP1 is gel purified. pCGN3224 is digested with PstI, ends are filled in with Klenow fragment and subsequently the vector is digested with Bgl II and gel purified. The purified vector and the purified CTP1::gcpE fusion are then ligated into digested and gel purified pGCN3223.

To transfer the *E. coli* gcpE gene into an *Arabidopsis* binary vector, pGCN3223 is digested with HindIII and Sac I and the gel purified fragment carrying the e35S promoter fused to CTP1 and gcpE is ligated into HindIII/SacI-digested and gel purified pMON26543, resulting in a vector containing gcpE under e35S promoter control. The pNapin binary expression vector is obtained by ligating the gel purified NotI fragment harboring the pNapin::CTP1::gcpE::napin 3' expression cassette into NotI digested pMON36176.

Seed-specific expression vectors for a rice gcpE (SEQ ID NO: 2) and a soybean gcpE (SEQ ID NO: 6) sequence are constructed using a pBin19 (Bevan, *Nucleic Acids Research* 12: 8711–8720, 1984) derivative. The plasmid contains the *Vicia faba* seed-specific promoter from the Legumin B4 gene (Bäiumlein et al., *Nucleic Acids Research* 14: 2707–2719, 1996), the sequence encoding the transit peptide of the Nicotiana tabacum transketolase (TkTp) (R. Badur, Ph.D. thesis, Georg August University of Göttingen, Germany, 1998) and the transcriptional termination sequence from the octopin synthase gene (Gielen et al., *EMBO J.* 3:835–846, 1984). A rice gcpE (SEQ ID NO: 2) sequence is cloned in sense orientation as a Bam HI fragment into the Bam HI site of the pBin-LePTkTp9 vector, resulting in a recombinant rice gcpE expression vector. A recombinant soybean gcpE (SEQ ID NO: 6) expression vector is similarly created.

EXAMPLE 10

Transformation of Plants

*Agrobacterium* transformed with the vectors of Example 9, and with pQE-AGH (which contains the *Arabidopsis* gcpE gene), are prepared as follows. 100 µl of an overnight culture is spread on an agar LB plate with antibiotics. The plate is placed upside down in a 30° C. chamber overnight. The plates are removed after colonies have grown (24–48 hours). A small scale culture is started by placing 10 ml of liquid LB media in a 50 ml tube. 10 µl Kanamycin (50 µg/µL), 10 µl Spectinomycin (75–100 µg/µL), and 10 µl Chloramphenicol (25 µg/µL) are added. *Agrobacterium* is added from a plate, and the tube is shaken and placed in a 30° C. shaker overnight.

Following overnight growth of the 10 ml culture, the culture is removed to a 500 ml flask. 200 ml of liquid LB is placed in a flask, 200 µl Kanamycin (50 µg/µL), 200 µl Spectinomycin (75–100 µg/µL), and 200 µl of Chloramphenicol (25 µg/µL) are added, and the entire 10 ml overnight culture is then added. The 500 ml flask is placed in a 30° C. shaker and grown overnight. The entire 200 ml culture is placed in a centrifuge tube and centrifuged for 25 minutes at 3,750 rpm and 19° C. After centrifugation, the liquid is poured off and the pellet is resuspended in 25 ml of 5% Sucrose (0.05% Silwet) solution.

900 µl of the sucrose solution and 100 µl of the 25 ml bacterial culture are placed in a cuvette, and the cuvette is shaken with a covering of parafilm. A blank OD reading is taken with 1 ml of sucrose solution, and then readings of all the bacterial solutions are taken. The OD (at a wavelength of 600) of each culture is recorded. The following calculations are then performed: $C_1V_1=C_2V_2$; $C_1V_1=(0.8)(200$ ml$)$; $C_1V_1=160$; $V_1=160/C_1$; and $V_1=X$ ml/10 to determine $OD_{600}=0.8$ of an *Agrobacterium* culture.

Plants are soaked for at least 30 minutes in water prior to dipping. The bacterial solution is poured into a shallow plastic container, and above ground parts of the plant (bolts, rosettes) are dipped into the solution for 3–5 seconds with gentle agitation. Dipped plants are placed on their side in a diaper lined black tray, and covered by a dome overnight (16–24 hours) to maintain a high humidity. The cover is removed and normal plant growth conditions are resumed for 4 weeks.

Following the transformation and high humidity treatment, plants are maintained at 22° C., 60% RH, and a 16 hour photoperiod for 4 weeks. 5–7 days after transformation, plants are coned. Fertilization with a weak 20-20-20 fertilizer is done weekly. After 4 weeks of growth, plants are placed in the greenhouse and all watering is stopped to encourage plant dry down for seed harvest. Plants are ready for seed harvest after 1–1.5 weeks of dry down. Seeds are harvested by cutting the base of the plant below the cones, holding the plant over a seed sieve and a white piece of paper, running bolts through the cone hole, and collecting clean seeds through sieving.

Seeds are sterilized by connecting a vacuum desiccator hose to a vacuum in a fume hood/flow bench. 100 ml of bleach is placed in a 250 ml beaker, and 3 ml of concentrated HCl is added to the bleach. The beaker is placed in the desiccator, and seeds in seed tubes in a tube holder are placed in the desiccator. A cover is placed on the desiccator, and the vacuum is operated. The desiccator is left overnight but no longer than 16 hours.

Once sterilized, seeds are plated on selection media (prepared by adding 10 g (2 g/L) Phyta-Gel, 10.75 g (2.15 g/L) MS Basal Salts (M-5524 from Sigma), 50 g (10 g/L) sucrose, and 6 ml (1.2 ml/L) Kanamycin solution (950 mg/ml), 5 ml (1 ml/L) Cefotaxime Solution (250 mg/ml), and 5 ml (1 ml/L) Carbenecillin Solution (250 mg/ml) to a total volume of 5 liters at a pH of 5.7). Seed tubes are tapped lightly over a plate in order to distribute the seeds sparsely. The plates are wrapped in parafilm and placed in a 4° C. refrigerator for 1–2 days of cold treatment. After this cold treatment the plates are placed in a 28° C. chamber for germination.

Selected plantlets are green and have secondary leaves developing. The selected plantlets are moved to soil after secondary leaves have developed. The plantlets are potted in soil and covered with a dome for 5 days to maintain high humidity. The plantlets are moved to a greenhouse after the bottom siliques begin to turn yellow.

Seeds from the selected plantlets are grown in 2.5 inch pots with soil (½ Metro-200; ½ PGX Mix). The soil is mounded and the pot is covered with mesh screen. The screen is fastened to the pot with a rubber band. Seeds are sown and covered with a germination dome. The seedlings are grown in a 12 hour photoperiod in 70% relative humidity at 22° C. Water is supplied every other day as needed and Peter's 20-20-20 fertilizer is applied from below, bi-weekly.

EXAMPLE 11

Production of Seeds from Transgenic Plants

Transgenic seed plants from Example 10 representing 20 independent transformation events are grown and seeds harvested to produce $T_2$ seeds. The $T_2$ seeds are grown and tested for tocopherol levels. Tocopherol levels are determined by adding 10 to 15 mg of Arabidopsis seed into a 2 mL microtube. A mass of 1 g of 0.5 mm microbeads (Biospecifics Technologies Corp., Lynbrook, N.Y.) and 500 µl 1% pyrogallol (Sigma Chem, St. Louis, Mo.) in ethanol containing 5 µg/mL tocol, are added to the tube. The sample is shaken twice for 45 seconds in a FastPrep (Bio 101/ Savant) at a speed of 6.5. The extract is filtered (Gelman PTFE acrodisc 0.2 µm, 13 mm syringe filters, Pall Gelman Laboratory Inc, Ann Arbor, Mich.) into an autosampler tube. HPLC is performed on a Zorbax silica HPLC column, 4.6 mm×250 mm (5 µm) with a fluorescent detection using a Hewlett Packard HPLC (Agilent Technologies, Palo Alto Calif.). Sample excitation is performed at 290 nm, and emission is monitored at 336 nm. Tocopherols are separated with a hexane methyl-t-butyl ether gradient using an injection volume of 20 µl, a flow rate of 1.5 ml/min, and a run time of 12 min (40° C.). Tocopherol concentration and composition is calculated based on standard curves for α, β, δ, and γ-tocopherol using Chemstation software (Agilent Technologies, Palo Alto Calif.).

EXAMPLE 12

Transgenic Plants with GCPE and Other Tocopherol Biosynthesis Genes

Canola, Brassica napus and soybean plants are transformed with a variety of DNA constructs using a particle bombardment approach essentially as set forth in Christou (1996) or using Agrobacterium mediated transformation. Two sets of DNA constructs are produced.

The first set of constructs are "single gene constructs" in which the gcpE gene is inserted into a plant DNA construct under the control of an arcelin 5, 7S alpha or napin promoter (Kridl et al., Seed Sci. Res. 1:209–219, 1991). The products of the gcpE gene can be targeted to the plastid by an encoded plastid target peptide such as CTP1 (Keegstra, Cell, 56(2): 247–253, 1989; Nawrath, et al., PNAS 91:12760–12764, 1994).

A second set of DNA constructs is generated and referred to as the "multiple gene constructs". The multiple gene constructs contain multiple genes each under the control of a napin promoter and the products of each of the genes are targeted to the plastid by an encoded plastid target peptide, such as a natural plastid target peptide present in the trans gene, or an encoded plastid target peptide such as CTP1.

The multiple gene construct contains the gcpE gene and one or more genes for other MEP pathway proteins, including, but not limited to: a ygbB gene; a ygbP gene; a ychB gene; a yfgA gene; a yfgB gene; a bifunctional prephenate dehydrogenase such as the E. herbicola or E. coli tyrA gene (Xia etval., J. Gen. Microbiol., 138:1309–1316, 1992), a phytylprenyltransferase such as the slr1736 gene (in Cyanobase, a web accessible database maintained by Kazusa DNA Research Institute. Kisarazu, JAPAN) or the ATPT2 gene (Smith et al., Plant J., 11:83–92, 1997), a deoxyxylulose synthase such as the E. coli dxs gene (Lois et al., PNAS, 95(5):2105–2110, 1998), a deoxyxylulose reductoisomerase such as the dxr gene (Takahashi et al., PNAS, 95(17):9879–9884, 1998), an Arabidopsis thaliana HPPD gene (Norris et al., Plant Physiol., 117:1317–1323, 1998), an Arabidopsis thaliana GGPPS gene (Bartley and Scolnik, Plant Physiol., 104:1469–1470, 1994), a transporter such as the AANT1 gene (Saint Guily, et al., Plant Physiol., 100(2): 3069–1071, 1992), a GMT gene (WO 00/32757, WO 00/10380), an MT1 gene, a tocopherol cyclase such as the slr1737 gene (in Cyanobase) or its Arabidopsis ortholog, an isopentenyl diphosphate isomerase (IDI) gene, and an antisense construct for homogentisic acid dioxygenase (Saro et al., J. DNA Res., 7(1):31–63, 2000).

Each construct is transformed into at least one canola, Brassica napus and soybean plant. Plants expressing each of these genes are selected to participate in additional crosses. The tocopherol composition and level in each plant is also analyzed using the method set forth in Example 11.

The tocopherol composition and level in each plant generated by the crosses (including all intermediate crosses) is also analyzed using the method set forth in Example 11. Progeny of the transformants from these constructs will be crossed with each other to stack the additional genes to reach the desired level of tocopherol.

Crosses are carried out for each species to generate transgenic plants having one or more of the following combination of introduced genes: gcpE, ygbB, ygbP, ychB; yfgA; yfgB; tyrA, slr1736, ATPT2, dxs, dxr, GGPPS, HPPD, GMT, AANT1, slr1737, IDI and an antisense construct for homogentisic acid dioxygenase.

The above description, sequences, drawings and examples are only illustrative of preferred embodiments that achieve the objects, features and advantages of the present invention. It is not intended that the present invention be limited to the illustrative embodiments. Any modification of the present invention which comes within the spirit and scope of the following claims should be considered part of the present invention.

What is claimed is:

1. A substantially purified nucleic acid molecule comprising a DNA molecule that encodes a protein comprising the amino acid sequence consisting of SEQ ID NO:50, operably linked to a DNA molecule that encodes a chloroplast transit peptide.

2. The substantially purified nucleic acid molecule of claim 1, wherein said nucleic acid molecule further comprises a promoter operably linked to the DNA molecule that encodes the chloroplast transit peptide.

3. A transformed host cell comprising the nucleic acid molecule of claim 2.

4. A transgenic plant comprising the nucleic acid molecule of claim 2.

5. Seed from the transgenic plant of claim 4, wherein the seed comprises the nucleic acid molecule of claim 4.

6. A method of producing a transgenic plant having a seed with an altered isoprenoid compound level comprising: (A) transforming a plant with a nucleic acid molecule to produce the transgenic plant, wherein the nucleic acid molecule encodes a protein with the amino acid sequence consisting of SEQ ID NO: 50; and (B) growing the transgenic plant.

\* \* \* \* \*